United States Patent
Accili et al.

(10) Patent No.: US 10,732,173 B2
(45) Date of Patent: Aug. 4, 2020

(54) USE OF ALDEHYDE DEHYDROGENASE AS BIOMARKER FOR BETA-CELL DYSFUNCTION AND LOSS

(71) Applicant: THE TRUSTEES OF COLUMBIA UNIVERSITY IN THE CITY OF NEW YORK, New York, NY (US)

(72) Inventors: Domenico Accili, New York, NY (US); Ja Young Kim-Muller, Brighton, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 316 days.

(21) Appl. No.: 15/760,469

(22) PCT Filed: Sep. 15, 2016

(86) PCT No.: PCT/US2016/052013
§ 371 (c)(1),
(2) Date: Mar. 15, 2018

(87) PCT Pub. No.: WO2017/049010
PCT Pub. Date: Mar. 23, 2017

(65) Prior Publication Data
US 2019/0265229 A1 Aug. 29, 2019

Related U.S. Application Data

(60) Provisional application No. 62/380,955, filed on Aug. 29, 2016, provisional application No. 62/219,073, filed on Sep. 15, 2015.

(51) Int. Cl.
*G01N 33/50* (2006.01)
*C12N 5/071* (2010.01)

(52) U.S. Cl.
CPC ......... *G01N 33/507* (2013.01); *C12N 5/0676* (2013.01); *G01N 33/5005* (2013.01);
(Continued)

(58) Field of Classification Search
CPC ...................................................... G01N 33/50
(Continued)

(56) References Cited

U.S. PATENT DOCUMENTS 7,381,523 B2    6/2008  Efendic
2006/0241869 A1* 10/2006 Schadt ................. C12Q 1/6883
                                                     702/19

(Continued)

FOREIGN PATENT DOCUMENTS

WO    2006007400 A2    1/2006
WO    2013039898 A1    3/2013
WO    2014085485 A1    6/2014

OTHER PUBLICATIONS

Lukowiak, B. et al, Journal of Histochemistry & Cytochemistry 2001, 49, 519-521.*

(Continued)

*Primary Examiner* — Arlen Soderquist
(74) *Attorney, Agent, or Firm* — Beusse Wolter Sanks & Maire; Timothy H. Van Dyke

(57) ABSTRACT

Methods are provided for obtaining a sample of β cells from an isolated donor pancreas or isolated pancreatic islets and analyzing the sample using flow cytometry to determine the percentage of β cells in the sample that express detectable levels of ALDH1 A3. If the percentage of ALDH1 A3-expressing β cells in the sample is about 3% or lower, then it is possible to determine that the pancreas or islets are healthy enough for implantation into a subject, and implanting the pancreas or islets. If the percentage of ALDH1 A3-expressing cells is above about 5%, then it is determined that the (Continued)

pancreas or islets are not suitable for implantation into the subject and discarding the pancreas or islets. Isolated non-insulin-producing or low-insulin-producing pancreatic beta cells are also provided.

29 Claims, 18 Drawing Sheets

(52) U.S. Cl.
CPC .... *C12N 2501/998* (2013.01); *C12N 2510/00* (2013.01); *G01N 2333/90203* (2013.01); *G01N 2800/042* (2013.01); *G01N 2800/52* (2013.01)

(58) Field of Classification Search
USPC .......................................................... 436/63
See application file for complete search history.

(56) References Cited

U.S. PATENT DOCUMENTS

| | | | | |
|---|---|---|---|---|
| 2007/0038386 | A1* | 2/2007 | Schadt | C12Q 1/6883 702/20 |
| 2012/0252045 | A1 | 10/2012 | Pepper | |
| 2012/0276572 | A1* | 11/2012 | Shekdar | C12Q 1/6897 435/29 |
| 2013/0287772 | A1* | 10/2013 | Halbert | C12Q 1/6883 424/134.1 |
| 2014/0017207 | A1* | 1/2014 | Leach | C12N 5/0676 424/93.7 |
| 2014/0148350 | A1* | 5/2014 | Spetzler | G01N 33/574 506/9 |
| 2014/0329704 | A1* | 11/2014 | Melton | C12Q 1/6881 506/9 |
| 2014/0349396 | A1* | 11/2014 | West | C12N 5/0658 435/366 |
| 2017/0204375 | A1* | 7/2017 | Accili | A61K 38/28 |

OTHER PUBLICATIONS

Rovira, M. et al, Proceeding of the National Academy of Sciences 2010, 107, 75-81.*
Mercader, J. M. et al, PLOS Genetics 2012, 8, paper e1003046, 14 pages.*
Li, J. et al, Diabetologia 2014, 57, 754-764.*
Kim-Muller, J. Y. et al, Nature Communications 2016, 7, paper 12631, 11 pages.*
Al-Masri et al., Effect of forkhead box O1 (FOXO1) on beta cell development in the human fetal pancreas, Diabetologia, 2010, pp. 699-711, vol. 53.
Guo et al., Inactivation of specific beta cell transcription factors in type 2 diabetes, J Clin Invest, 2013, pp. 3305-3316, vol. 123.
Kitamura et al., Regulation of pancreatic juxtaductal endocrine cell formation by FOXO1, Molecular and cellular biology, 2009, pp. 4417-4430, vol. 29.
Kitamura et al., FOXO1 protects against pancreatic beta cell failure through NeuroD and MafA induction, Cell metabolism, 2005, pp. 153-163, vol. 2.
Marcato et al., Aldehyde dehydrogenase: its role as a cancer stem cell marker comes down to the specific isoform, Cell cycle, 2011, pp. 1378-1384, vol. 10.

Shimamura et al., Raldh3 expression in diabetic islets reciprocally regulates secretion of insulin and glucagon from pancreatic islets, Biochem Biophys Res Commun, 2010, pp. 79-84, vol. 401.
Talchai et al., Genetic and biochemical pathways of beta-cell failure in type 2 diabetes, Diabetes Obes Metab, 2009, pp. 38-45, vol. 11.
Talchai et al., Pancreatic beta Cell Dedifferentiation as a Mechanism of Diabetic beta Cell Failure, Cell, 2012, pp. 1223-1234, vol. 150.
Taylor et al., Nkx6.1 is essential for maintaining the functional state of pancreatic beta cells, Cell reports, 2013, pp. 1262-1275, vol. 4.
Kim-Muller et al., Metabolic inflexibility impairs insulin secretion and results in MODY-like diabetes in triple FoxO-deficient mice, Cell Metab, 2014, pp. 593-602, vol. 20.
Talchai & Accili, Legacy Effect of Foxo1 in Pancreatic Endocrine Progenitors on Adult beta-Cell Mass and Function. Diabetes, 2015, pp. 2868-2879, vol. 64.
Ginestier et al., ALDH1 is a marker of normal and malignant human mammary stem cells and a predictor of poor clinical outcome, 2007, Cell stem cell, pp. 555-567, vol. 1.
Fleischman, ALDH marks leukemia stem cell, Blood, 2012, pp. 3376-3377, vol. 119.
Awad et al., High ALDH activity identifies chemotherapy-resistant Ewing's sarcoma stem cells that retain sensitivity to EWS-FLI1 inhibition, PLoS One, 2010, e13943, vol. 5.
Huang et al., Aldehyde dehydrogenase 1 is a marker for normal and malignant human colonic stem cells (SC) and tracks SC overpopulation during colon tumorigenesis, Cancer research, 2009, pp. 3382-3389, vol. 69.
Croker et al., High aldehyde dehydrogenase and expression of cancer stem cell markers selects for breast cancer cells with enhanced malignant and metastatic ability, J Cell Mol Med, 2009, pp. 2236-2252, vol. 13.
Talchai et al., Generation of functional insulin-producing cells in the gut by Foxo1 ablation, Nat Genet, 2012, pp. 406-412, vol. 44.
Wang et al., Pancreatic beta cell dedifferentiation in diabetes and redifferentiation following insulin therapy, Cell Metab, 2014, pp. 872-882, vol. 19.
Tessem et al., Nkx6.1 regulates islet beta-cell proliferation via Nr4a1 and Nr4a3 nuclear receptors, Proc Natl Aced Sci U S A, 2014, pp. 5242-5247, vol. 111.
Marroqui et al., BACH2, a candidate risk gene for type 1 diabetes, regulates apoptosis in pancreatic beta-cells via JNK1 modulation and crosstalk with the candidate gene PTPN2, Diabetes, 2014, pp. 2516-2527, vol. 63.
Tang et al., Ablation of Elovl6 protects pancreatic islets from high-fat diet-induced impairment of insulin secretion, Biochem Biophys Res Commun, 2014, pp. 318-323, vol. 450.
Kamio et al., B-cell-specific transcription factor BACH2 modifies the cytotoxic effects of anticancer drugs, Blood, 2003, pp. 3317-3322, vol. 102.
Yasuda et al., Variants in KCNQ1 are associated with susceptibility to type 2 diabetes mellitus, Nat Genet, 2008, pp. 1092-1097, vol. 40.
Kim-Muller et al., FoxO1 deacetylation decreases fatty acid oxidation in beta-cells and sustains insulin secretion in diabetes, J Biol Chem, 2016, pp. 10162-10172, vol. 291.
Clardy et al., Rapid, high efficiency isolation of pancreatic β-cells Scientific Reports, Scientific Reports, 2015, pp. 13681, vol. 5.
Balber, Concise Review: Aldehyde Dehydrogenase Bright Stem and Progenitor Cell Populations from Normal Tissues: Characteristics, Activities, and Emerging Uses in Regenerative Medicine, STEM Cells, 2011, pp. 570-575, vol. 29.
Zhang et al., ALDH1A3: A Marker of Mesenchymal Phenotype in Gliomas Associated with Cell Invasion, PLoS One, 2015, pp. e0142856, vol. 10.

* cited by examiner

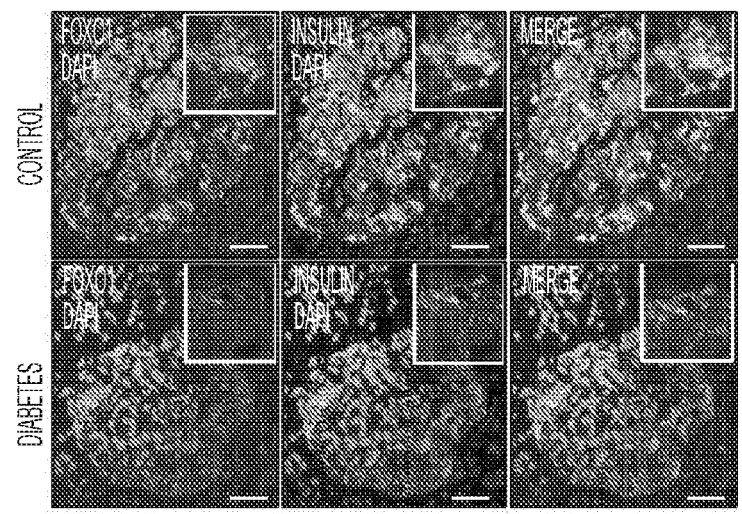
FIG. 3A
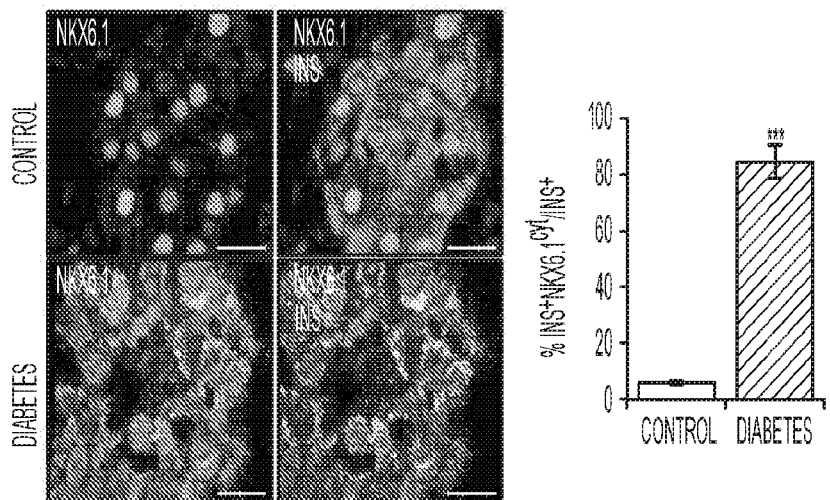
FIG. 3B
FIG. 3C
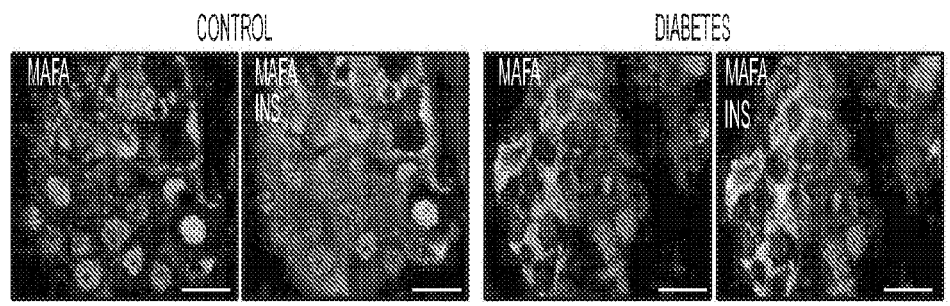
FIG. 3D

USE OF ALDEHYDE DEHYDROGENASE AS BIOMARKER FOR BETA-CELL DYSFUNCTION AND LOSS

CROSS-REFERENCE TO RELATED APPLICATIONS

This application is a 371 national stage application of PCT Application No. PCT/US2016/052013 filed Sep. 15, 2016 which claims the benefit of priority to U.S. Provisional Application No. 62/219,073, filed Sep. 15, 2015, and U.S. Provisional Application No. 62/380,955, filed Aug. 29, 2016, the entire contents of which are hereby incorporated by reference in their entireties as if fully set forth herein, under 35 U.S.C. § 119(e).

STATEMENT OF GOVERNMENT INTEREST

This invention was made with government support under DK064819 awarded by the National Institutes of Health. The government has certain rights in the invention.

BACKGROUND

Type 2 diabetes is associated with (and possibly caused by) defects in pancreatic β-cell mass and function. β cells of diabetics show a blunted and mistimed response to a glucose challenge. Moreover, unlike insulin resistance, which appears to remain relatively constant during the development of diabetes, β-cell function steeply deteriorates with time in a manner that is impervious to, and possibly worsened by, existing treatments. This occurs despite the fact that reversal of hyperglycemia can partly restore β-cell function, even in patients with advanced disease, hence the clinical conundrum of what is to be done to treat β-cell dysfunction. Treatments range from preserving β-cell function by reducing the metabolic demand on the β cells, to increasing β-cell performance and mass to meet the increased metabolic demand. Despite these efforts, it is still unclear whether the two primary components of β-cell failure, impaired insulin secretion and reduced β-cell mass, are mechanistically linked. Thus, understanding the mechanism linking these twin abnormalities can provide clues as to the best therapeutic approach to β-cell failure. Many cellular biological mechanisms and potential drug targets have been identified and postulated to play a role, either central or supportive, in β-cell dysfunction. Recently, in studies of FOXO1-deficient β cells, Applicant reported that β-cell dedifferentiation, rather than apoptosis, is a mechanism of β-cell dysfunction that can lead to new ways to intervene in the treatment of diabetes.

BRIEF DESCRIPTION OF THE DRAWINGS

The present invention is illustrated by way of example, and not by way of limitation, in the figures of the accompanying drawings and in which:

(FIG. 1A) Immunofluorescent histochemistry on pancreatic section using insulin (Ins), combined glucagon (Gcg), somatostatin (Ssn), pancreatic polypeptide (PP) (1010) and SYNAPTOPHYSIN (Syn, 1020). (FIG. 1B) Quantitative analysis of the data in A. (FIG. 1C) Immunofluorescent histochemistry with the 4-hormone cocktail (4H, 1030) and CHROMOGRANIN A (CGA, 1040). Data in panel B are means±SEM. **=P<0.001 by Student's t test. Scale bars=20 μm (n=15 for each group).

(FIG. 2A) Immunofluorescence of ALDH1a3 (2010) with Insulin (2020) (no co-localization) and ALDH1a3 with glucagon (2030). (FIG. 2B-2D) Quantitative analysis of the data shown as means±SEM. *=P=0.05, **=P<0.01 by Student's t test. Scale bars=20 μm (n=5 for each group).

FIG. 3A-3D. Expression of FOXO1 (FIG. 3A), NKX6.1 (FIG. 3B), quantitative analysis of cytoplasmic NKX6.1 (FIG. 3C) and MAFA (FIG. 3D) in pancreatic islets. (FIG. 3A) Immunofluorescence on fresh-frozen pancreatic sections with FOXO1 (3010) and insulin (3020). (FIG. 3B) Immunofluorescence with NKX6.1 (3030) insulin (3040), and DAPI (3050). (FIG. 3C) Quantitative analysis of the data, shown as means±SEM. (FIG. 3D) Immunofluorescence with MAFA (3060), insulin (3070) and DAPI (3080). Enlargements show representative b-cells. ***=P<0.001 by Student's t test. Scale bars=20 μm.

(FIG. 4A) Immunofluorescence of pancreatic islets with FOXO1 (4010), NKX6.1 (4020), and DAPI (4030) (Scale bars=51 m). (FIG. 4B) Immunofluorescence of pancreatic islets with NKX6.1 (4040, and insulin (4050) (Scale bars=10 μm). (FIG. 4C) Proposed model of "dedifferentiating" β cells. (FIG. 4D) ALDH1A3 co-localization with cytoplasmic NKX6.1 (4060) (Scale bars=10 μm) (FIG. 4E) Quantitative analysis of the data expressed as means±SEM. **=P<0.01 by Student's t test (n=5 for each group).

(FIG. 5A) Mislocalization of FOXO1 to glucagon-immunoreactive cells (5010). (FIG. 5B) Quantitative analysis of converted β-cells to β-cells. (FIG. 5C) Mislocalization of FOXO1 (5020) to ARX- and glucagon-immunoreactive cells. (FIG. 5D) Quantitative analysis of converted β-cells to α-cells, as determined by the assay in FIG. 5C. (FIG. 5E) Mislocalization of NKX6.1 (5030) to somatostatin-immunoreactive cells (5040). (FIG. 5F) Quantitative analysis of converted β-cells to α-cells. Insulin immunofluorescence is shown in 5050 (FIG. 5A and FIG. 5C) (Scale bars=10 μm in FIG. 5A, FIG. 5C, and FIG. 5E). In all panels, nuclei are counterstained with DAPI (5060). 5070, 5080, and 5090 in panel indicate FOXO+/GCG+ cells (FIG. 5A) and FOXO1+/GCG+/Arx+ (FIG. 5C). FIG. 5B, FIG. 5D, and FIG. 5F show data as means±SEM. *=P=0.05, =P<0.01, *=P<0.001 by Student's t test (n=5 for each group).

(FIG. 6A) Expression of several ALDHs in transcriptome analyses of β-triple FOXO and progenitor-triple FOXO mice. (FIG. 6B) Expression levels of ALDH1 isoforms in normal pancreatic islets. (FIG. 6C) mRNA and (FIG. 6D) protein levels of ALDH1A1 and ALDH1A3 in isolated islets from different β-cell dysfunction models.

(FIG. 7A) Expressions of ALDH1A3 (7010) and Insulin (7020) in hyperglycemic GirKO and euglycemic WT littermates. (FIG. 7B) Expressions of ALDH1A3 (7030) and Insulin (7040) in obese diabetic db/db and aged triple knockout of Foxo1, 3a, and 4 in mature 1 cells (f-triple FOXO) animals.

(FIG. 8A) mRNA levels of several key genes regulating insulin secretion and hormone expression and (FIG. 8B) glucose stimulated insulin secretion in either Ad-hALDH1A3 or control, Ad-Gfp transduced primary islets.

(FIG. 10A) Western blot of ALDH1A3 in islets isolated from different models of wild-type and diabetic mice. The lower molecular weight band in young (3-month-old) mice is a non-specific band commonly observed with Aldh1a3 immunodetection. All-trans (FIG. 10B) and 9-cis retinoic acid (FIG. 10C) in whole pancreas of control and diabetic mice. Shaded bars: db/db mice and their wild-type controls. Filled bars: Pdx-cre Foxo knockout mice and their wild-type controls (n=5 for each group). One asterisk indicates p<0.05 by one-way ANOVA. Error bars indicate standard error of the mean.

(FIG. 11A) ALDH1A3 immunoreactivity in islets from normal and diabetic GIRKO mice. (FIG. 11B) Co-immunostaining of ALDH1A3 and insulin or glucagon, somatostatin (Sms), and Pp in db/db, GIRKO, and Pdx1-cre-driven Foxo knockout mice. Co-immunostaining of ALDH1A3 with MafA (FIG. 11C), Pdx1 (FIG. 11D), or Nkx6.1 (FIG. 11E). ALDH+/Nkx6.1-cells are indicated by the white arrows. MafA/ALDH1A3 (FIG. 11C) immunohistochemistry was performed on consecutive sections, whereas Pdx1/ALDH1A3 and NKX6.1/ALDH1A3 immunohistochemistry was performed on the same section. Co-immunohistochemistry of ALDH1A3 with progenitor cell markers, L-myc (FIG. 11F) and Neurogenin3 (FIG. 11G). ALDH1A3+/Neurog3+ cells are indicated by the white arrows. Neurog3/ALDH1a3 immunohistochemistry was performed on consecutive sections. To better assess Neurog3/ALDH1A3-positive cells, we provide two representative sections from Foxo knockout mice. Scale bar: 1001 μM in FIG. 11A and FIG. 11C, 50 μM in FIG. 11D-FIG. 11G. In FIG. 11B, left panel: 100 μM, right panel 50 μM.

(FIG. 12A) Effect of Foxo1 over-expression on Aldh1a3 mRNA in Min6 cells. Foxo-DN is a truncated mutant that is una-ble to drive gene expression and competes with endogenous Foxo for DNA binding. Foxo-DBD is a mutant unable to bind the Foxo response element, but can still function as a coregulator of gene expression 28. (FIG. 12B) Western blot analysis of ALDH1A3 levels following lentiviral transduction in MIN6 cells. (FIG. 12C) Gene expression in Min6 cells stably-expressing GFP or ALDH1a3. MIN6 cells stably transfected with ALDH1A3. (FIG. 12D) Insulin secretion expressed as fold-increase from 5 to 20 mM glucose in MIN6 cells expressing either GFP or ALDH1A3 (n=8). (FIG. 12E) Insulin secretion in primary islets from C57Bl/6J mice expressing either GFP or ALDH1A3 adenovirus (n=3). (FIG. 12F) Insulin secretion (expressed as in FIG. 12D) in islets isolated from db/db mice and their wild-type controls following treatment with the ALDH inhibitor DEAB at the doses indicated (n=4). Each experiment was performed with pooled islets from 5 mice per genotype. (FIG. 12G) Area under the curve of oxygen consumption rates measured in Min6 cells stably expressing either GFP or ALDH1A3 (n=4 per group). One asterisk indicates p<0.05 by one-way ANOVA. Error bars indicate standard error of the mean.

FIG. 13A-13N. Isolation and characterization of ALDH+ cells. (FIG. 13A) Enrich-ment procedure to isolate ALDH-expressing islet cells. β cells are labeled red by Rip-cre-activated Tomato. Cells are incubated with ALDEFLUOR™, and selected for tomato and ALDEFLUOR™, yielding ALDH− (low) and ALDH+ (high) cells. (FIG. 13F-FIG. 13N) qPCR analysis of selected transcripts in the different fractions isolated from islet cell preparations. One asterisk indicates p<0.05 by one-way ANOVA.

(FIG. 14A) Data from RNA sequencing of all ALDH transcripts are represented as column Z-scores. Each row represents a different ALDH isoform, and each column an individual sample used for analysis. RFP+ALDH−: JD001 through JD014, and RFP+ALDH+: JD003 through JD015. Aldh1a3 is boxed for refer-ence. (FIG. 14B) Model of the relationship between changes in Foxo levels and gene expression signature of ALDH+ cells.

SUMMARY

Figure 1A:
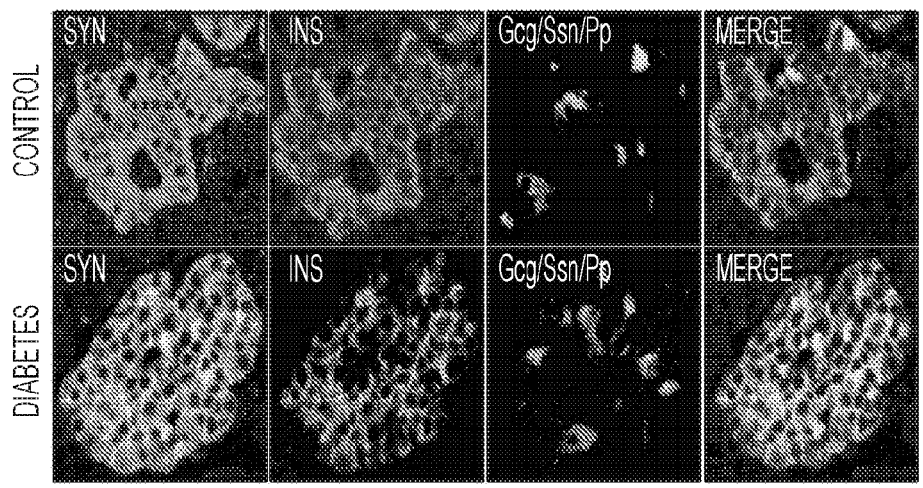
FIG. 1A-1C. Representative Images of Dedifferentiated β cells.

Methods are provided for determining whether ALDH1A3-expressing beta cells are healthy enough for implantation into a subject. First, a sample that comprises beta cells from an isolated donor pancreas or isolated pancreatic islets is obtained. Then the sample is analyzed to determine if the percentage of beta cells in the sample express detectable levels of ALDH1A3, such as by using flow cytometry (e.g., fluorescent assisted cell sorting that uses ALDEFLUOR™). If the percentage of ALDH1A3-expressing beta cells in the sample is about 3% or lower, then it is determined that the pancreas or islets are healthy enough for implantation into a subject, and implanting the pancreas or islets into a subject in need. If the percentage of ALDH1A3-expressing cells is above about 5%, then it is determined that the pancreas or islets are not suitable for implantation into the subject and the pancreas or islets are not implanted.

In other embodiments, methods are provided for obtaining a sample of beta cells from a pancreas or pancreatic islets, and isolating beta cells that express detectable levels of ALDH1A3 using flow cytometry. Methods are also provided for contacting (e.g., in vitro or in vivo) a population of ALDH1A3$^{hi}$ beta cells that have been isolated from a mammalian diabetic pancreas with a plurality of test agents in a high throughput screen for a time and under conditions that permit the test agent to affect ALDH1A3 expression or activity. Then, a test agent is selected if it caused a statistically significant reduction in the level of ALDH1A3 expression or activity compared to pre-contact levels. In certain embodiments, the method further comprises contacting a noninsulin-producing beta-cell population with the selected test agent and determining if the selected test agent caused at least a statistically significant increase in insulin production, insulin secretion or both after contact compared to respective pre-contact levels. If the selected test agent significantly increases insulin production, insulin secretion or both after contact compared to respective pre-contact levels then test agent is selected as a potential therapeutic agent. The noninsulin-producing beta-cell population comprises a whole pancreatic islet or an islet fragment. The noninsulin-producing beta-cell population is isolated from a mammalian diabetic pancreas (e.g., from a human). In some embodiments, the ALDH1A3$^{hi}$ beta cells have no insulin production or impaired insulin production. In other embodiments, the ALDH1A3$^{hi}$ beta cells are isolated (e.g., by flow cytometry) from a human diabetic pancreas. Levels of ALDH1A3 expression may be determined using either fluorescence of ALDH1A3 or a protein r mRNA assay. A reduction of ALDH1A3 in some embodiments correlates with an increase in insulin production or secretion or both. A significant reduction of ALDH1A3 expression or activity is reduction of about 2-, 10-, 25-, 50- or 100-fold compared to precontact levels. In other embodiments, a significant reduction in ALDH1A3 causes a delay in progression of dedifferentiation, cessation of dedifferentiation or a reversal of dedifferentiation of the beta cells.

In some embodiments, isolated noninsulin-producing or low-insulin-producing pancreatic beta cells that express a statistically significantly higher level of ALDH1A3 protein, mRNA encoding ALDH1A3 or ALDH1A3 enzyme activity than normal insulin-producing pancreatic cells are provided. A significantly higher level of ALDH1A3 protein expression or enzyme activity is about 2-, 10-, 25-, 50- or 100-fold higher than in normal insulin-producing pancreatic cells. The isolated pancreatic cells are isolated by FACS based on elevated ALDH1A3 expression. In other embodiments, a significant increase in insulin production and/or secretion is about a 20% increase compared to precontact levels. The significant increase is an increase of at least about 20% compared to precontact levels in some embodiments.

DETAILED DESCRIPTION

Reported herein is the discovery of an isoform of the enzyme aldehyde dehydrogenase (ALDH1A3) as a biomarker of dysfunctional 13 cells. ALDH1A3-expressing islet cells have been isolated and characterized. Their gene expression profiles were compared in normal and diabetic mice. The data indicate that two reciprocal processes unfold in failing β cells: a decrease of mitochondrial function with presumptive activation of RICTOR, likely compensatory in nature, associated with progenitor cell-like features. A narrow set of candidate genes have been identified that may affect the transition from a healthy to a dysfunctional β cell. The significance of this work consists in the discovery of a biomarker of β-cell dysfunction that can also be used to isolate failing cells; and in the identification of a pathogenic mechanism and a narrow set of potential effectors that can be tested for therapeutic relevance.

Insulin-producing β cells become dedifferentiated during diabetes progression. An impaired ability to select substrates for oxidative phosphorylation or metabolic inflexibility initiates progression from β-cell dysfunction to β-cell dedifferentiation. The identification of pathways involved in dedifferentiation may provide clues to its reversal. Here, failing β cells are isolated and functionally characterized from various experimental models of diabetes are presented. An enrichment in the expression of aldehyde dehydrogenase 1 isoform A3 (ALDH+) is reported as β cells become dedifferentiated. Flow-sorted ALDH+ islet cells demonstrate impaired glucose-induced insulin secretion, are depleted of Foxo1 and MafA, and include a Neurogenin3-positive subset. RNA sequencing analysis demonstrates that ALDH+ cells are characterized by: (i) impaired oxidative phosphorylation and mitochondrial complex I, IV, and V; (ii) activated RICTOR; and (iii) progenitor cell markers. Without being bound by theory, it is proposed that impaired mitochondrial function marks the progression from metabolic inflexibility to dedifferentiation in the natural history of β cell failure.

The results described herein show that elevated levels of the ALDH1A3 isoform of the enzyme aldehyde dehydrogenase are a biomarker of dysfunctional pancreatic beta cells. This discovery was made by isolating and characterizing ALDH1A3-expressing islet cells, and comparing their gene expression profiles in normal and diabetic mice. Data provide evidence that two reciprocal processes unfold in failing beta cells: (i) a decrease of mitochondrial function with presumptive activation of RICTOR, likely compensatory in nature, associated with progenitor cell-like features, and (ii) a narrow set of candidate genes that may affect the transition from a healthy to a dysfunctional β cell.

Previous studies from Applicant show that deletion or suppression of Foxo1 caused normal pancreatic β cells to dedifferentiate into noninsulin-producing β cells or islets. It has now been discovered that these dedifferentiated noninsulin-producing β cells express unusually high levels of the enzyme ALDH1A3 (hereafter ALDH1A3$^{hi}$ β-cells), sometimes as much as 100× higher levels than in normal insulin-producing 13 cells (hereafter ALDH1A3$^{low}$ β-cells). By contrast, normal insulin-producing β cells have low levels of ALDH1A3, and do not produce sufficient fluorescence levels to be detectable by FACS. Thus, dysfunctional β cells, for example from a diabetic pancreas, can be detected and hence isolated/separated based on their high ALDH1A3 fluorescence using flow cytometry such as FACS. Certain embodiments are directed to high throughput screening methods wherein isolated ALDH1A3$^{hi}$ mammalian β cells from cadaverous diabetic pancreata, preferably human, are screened against large numbers of test agents to identify those that significantly reduce ALDH1A3 expression or return it to normal levels. In another embodiment, test agents selected because they significantly reduce ALDH1A3 expression or return it to normal levels, are then tested in vitro or in vivo to determine whether they cause noninsulin-producing diabetic β cells to produce and/or secrete insulin, which makes them potential therapeutic agents for treating diabetes.

Another embodiment of the invention is directed to isolated pancreatic or islet β cells that express elevated levels of ALDH1A3$^{hi}$ and no or low impaired levels of insulin, such as would be found in a diabetic pancreas, which cells can be isolated by FACS to provide a source of non-insulin-producing dedifferentiated β cells as well as β cells that are in the process of dedifferentiating and losing the ability to make and secrete insulin.

In another embodiment, the percentage of ALDH1A3-expressing β cells in a sample of pancreas or pancreatic islets is determined using flow cytometry to decide whether a donor pancreas or isolated pancreatic islets are suitable for implantation/transplantation into a human subject. In this method an embodiment comprises: obtaining a sample of β cells from an isolated donor pancreas or pancreatic islets, analyzing the sample using flow cytometry to determine the percentage of β cells in the sample that express detectable levels of ALDH1A3, and if the percentage of ALDH1A3-expressing beta cells is about 3% or less, then determining that the pancreas or islet cells are suitable for implantation into a subject and proceeding with implantation. However, if the percentage of ALDH1A3-expressing cells is above about 5%, then determining that the pancreas or islets are not healthy enough and therefore are not suitable for implantation/transplantation into the subject. For isolated pancreas or islets that are found to have a percentage of ALDH1A3-expressing cells of above about 5%, these can be discarded. It is difficult to determine whether a pancreas or islet sample having a percentage of ALDH1A3-expressing cells above 3% and below 5% would be suitable for implantation. Procedures for isolating and implanting pancreatic islets into a subject in need are known in the art and are further described herein.

1. DEFINITIONS

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Kandel et al., eds., McGraw-Hill/Appleton & Lange: New York (2000). Unless defined otherwise, all technical and scientific terms used herein have the same meaning as commonly understood by one of ordinary skill in the art.

The phrase "high throughput screen" or a "high throughput screening method" as used herein defines a process in which large numbers of test agents, e.g., compounds, are tested rapidly and in parallel for the ability to reduce aldehyde dehydrogenase 1A3 (ALDH1A3) expression or activity in isolated ALDH1A3$^{hi}$ cells. In certain embodiments, "large numbers of agents, e.g., compounds" may be, for example, more than 100 or more than 300 or more than 500 or more than 1,000 compounds. Preferably, the process is an automated process.

"Test agent" or "test compound" includes any chemical or biological factor that is used in the methods of the invention, whether new (i.e., a "new chemical entity" or NCE) or known (e.g., a small molecule drug lead or small molecule already-approved drug), that is administered to or contacted with one or more cells, tissues, or organisms for the purpose of screening it for biological or biochemical activity toward the goal of discovering its use as a potential therapeutic agent to treat or prevent Type 2 diabetes. In an embodiment, test agents are first screened for the ability to reduce ALDH1A3 levels in noninsulin-producing beta cells (ALDH1A3$^{hi}$ cells) such as those isolated from a diabetic pancreas, and are then tested in a biological assay to determine their ability to increase insulin production and secretion in noninsulin-producing cells, such as beta cells isolated from diabetic pancreas or diabetic islets. Test agents that both reduce ALDH1A3 levels and increase insulin production and secretion are potential therapeutic agents.

"Biological factor" as used herein means any compound made by a living system that is administered to one or more cells, tissues, or organisms for the purpose of screening it for biological or biochemical activity toward the goal of discovering its use as a potential therapeutic agent[s] (drug[s]). Examples of biological factors include, but are not limited to, antibodies, hormones, enzymes, enzyme cofactors, peptides, secreted proteins, intracellular proteins, membrane-bound proteins, lipids, phospholipids, carbohydrates, fatty acids, amino acids, nucleic acids (including deoxyribonucleic acids and ribonucleic acids), steroids, and the like. Biological factors also include those compounds made by a living system that have been subsequently altered, modified, or optimized, for example, by way of laboratory techniques.

The "transcriptome" is the set of all RNA molecules, including mRNA, rRNA, tRNA, and other non-coding RNA produced in one or a population of cells. It differs from the exome in that it includes only those RNA molecules found in a specified cell population, and usually includes the amount or concentration of each RNA molecule in addition to the molecular identities.

"β-cell dysfunction" means a reduction or loss of the ability to produce and/or secrete insulin. As described herein this loss is due to dedifferentiation beta-cells that express significantly higher levels of ALDH1A3 (ALDH1A3$^{hi}$) than normal insulin-producing β cells (ALDH1A3$^{low}$).

"β-triple FOXO" means animals that lack expression and/or activity of the three FOXO isoforms (1, 3a and 4) in mature β cells.

As used herein, the terms "animal," "patient," or "subject" include mammals, e.g., humans, dogs, cows, horses, kangaroos, pigs, sheep, goats, cats, mice, rabbits, rats, and transgenic non-human animals. The preferred animal, patient, or subject is a human.

A "subject in need" is a subject that has a disease or disorder characterized by impaired pancreatic function including inappropriately low insulin levels, diabetes types 1 and 2, metabolic syndrome, obesity, glucose intolerance, hyperglycemia, decreased insulin sensitivity, increased fasting glucose, or increased post-prandial glucose. "Inappropriately low insulin levels" means insulin levels that are low enough to contribute to at least one symptom of the disease or disorder. "Impaired pancreatic function" is one in which the pathology is associated with a diminished capacity in a subject for the pancreas to produce and/or secrete insulin compared to a normal healthy subject.

A "growth environment" is an environment in which cells of interest will proliferate, differentiate, or mature in vitro. Features of the environment include the medium in which the cells are cultured, any growth factors or differentiation factors that may be present, and a supporting structure (such as a substrate on a solid surface) if present.

"ALDH1A3$^{low}$ cells" and "ALDH$^{low}$" are used interchangeably to refer to normal β-cells that produce insulin that have normal levels of ALDH1A3 expression. Normal levels of ALDH1A3 in pancreatic beta cells are undetectable by flow cytometry.

"ALDH1A3$^{hi}$ cells", "ALDH+" and ALDH$^{hi}$" are used interchangeably to refer to β cells that have dedifferentiated or are in the process of dedifferentiating into noninsulin-producing or low insulin-producing cells, respectively, that express statistically significantly increased levels of ALDH1A3 relative to normal β cells (ALDH1A3$^{low}$.) ALDH1A3$^{hi}$ cells include β cells from a diabetic animal. In some embodiments a statistically significantly higher level of ALDH1A3$^{hi}$ means a level at least a two-fold higher than normal β cells.

A test agent that "significantly reduces ALDH1A3 expression" in ALDH1A3$^{hi}$ cells is one that reduces ALDH1A3 expression by a statistically significant amount compared to controls. In certain embodiments the statistically significant reduction in ALDH1A3 is 2-, 10-25-, 50- or 100-fold compared to precontact levels.

In certain embodiments, ALDH1A3$^{hi}$ cells are FACS isolated and used in screening assay embodiments to identify test agents that significantly reduce ALDH1A3 expression. Normal insulin-producing β cells do not express detectable levels of ALDH1A3, however, ALDH1A3 expression is elevated in dysfunctional or dedifferentiated β cells. Therefore, the dedifferentiating or dedifferentiated ALDH1A3$^{hi}$ cells can be easily isolated based on their fluorescence as described herein.

"Non-insulin producing cells" in the context of the invention refers to cells, typically β cells, that have impaired insulin production. These cells include cells with low insulin or no insulin production and/or secretion.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

2. OVERVIEW

Type 2 diabetes is associated with progressive β-cell failure, resulting from combined loss of insulin secretory function and β-cell number (Ferrannini, 2010). Prospective studies of subjects at high risk of developing or newly diagnosed with type 2 diabetes underscore that, while insulin resistance remains relatively stable initially, in time, 1-cell function undergoes a steady decline (Defronzo et al., 2013; Levy et al., 1998; Weyer et al., 1999). Yet, despite its progressive course, β-cell failure can be partly and temporarily reversed by dietary or pharmacological interventions (Defronzo et al., 2013; Savage et al., 1979). While the progression of β-cell failure could be ascribed to cell death, its apparent reversibility suggests that cellular loss is not permanent (Marselli et al., 2014; Savage et al., 1979). Interestingly, insulin sensitizers appear to outperform insulin secretagogues in staving off β-cell dysfunction (Kahn et al., 2006; U.K. Prospective Diabetes Study Group, 1998), possibly indicating a mechanistic link between altered insulin secretion and β-cell loss. Cellular pathologies such as apoptosis, autophagy, oxidative stress, and nutrient overload ("toxicity") can affect either β-cell function or mass (Butler et al., 2007; Talchai et al., 2009; Phase 3 Trial of Transplantation of Human Islets in Type 1 Diabetes Complicated by Severe Hypoglycemia; DOI: 10.2337/dc15-1988).

Animal studies demonstrate that pancreatic β cells of mice become dedifferentiated in response to hyperglycemia, reverting to a progenitor-like state (Guo et al., 2013; Purl et al., 2013; Talchai et al., 2012; Taylor et al., 2013; Wang et al., 2014). In addition, β cells dedifferentiate into other endocrine cells, including glucagon-producing "α-like" cells (Talchai et al., 2012), thus providing a potential explanation for the hyperglucagonemia of diabetes (Dunning and Gerich, 2007; Yoon et al., 2003).

Pancreatic β-cell failure in type 2 diabetes is associated with functional abnormalities of insulin secretion and deficits of β-cell mass. The cellular plasticity of the endocrine pancreas remains largely untested in the pathophysiology of human diabetes (Dor and Glaser, 2013). It is known that the murine Foxo1 is expressed in different tissues and is a negative regulator of insulin sensitivity in liver, pancreatic β cells, and adipocytes (Nakae et al., 2002). Impaired insulin signaling to FOXO1 provides a unifying mechanism for the metabolic abnormalities of type 2 diabetes. It is known that loss of β-cell mass can be ascribed to impaired FOXO1 function in different animal models of diabetes (Kim-Muller et al. *Cell Metab*. 2014 20(4):593-602). It has been shown that in the pancreas, FOXO1 promoted the β-cell response to stress, but FOXO1 ablation did not affect the generation of different pancreatic endocrine cell types. (Kitamura, T. et al., 2009. Mol Cell Biol 29 (16): 4417-4430; Kitamura, Y. I. et al., 2005 *Cell Metab* 2 (3): 153-163; Kawamori, D. et al., 2006 *J Biol Chem* 281 (2): 1091-1098.)

The human aldehyde dehydrogenase superfamily comprises 19 known NAD(P+)-dependent enzymes that irreversibly catalyze the oxidation of both endogenously and exogenously produced aldehydes to their respective carboxylic acids. The Aldehyde dehydrogenase 1 family (ALDH1s) consists of the primary ALDHs (−1A1, −1A2, −1A3) that synthesize Retinoic acid (RA) from retinal and are therefore crucial in regulating RA signaling. Some stem cells, such as those associated with hematopoiesis, possess higher ALDH activity than normal cells, a characteristic that can be exploited for the isolation of primitive stem cell populations. Such activity in hematopoietic stem cells mediated RA signaling and thereby serves to regulate self-renewal and differentiation of these cells. Recently, RNA knockdown and antibody staining methods have implicated ALDH1A3, not ALDH1A1 as a major contributor to aldehyde oxidation in breast cancer stem cells.

Increased activity of aldehyde dehydrogenase (ALDH), a detoxifying enzyme responsible for the oxidation of intracellular aldehydes, has been detected in some stem/progenitor cells. For example, high ALDH activity has been found in murine and human hematopoietic and neural stem and progenitor cells (see Armstrong L, et al., (2004) Stem Cells 22: 1142-1151; Hess D A, et al. (2008) Stem Cells 26: 611-620; Hess D A, et al. (2004) Blood 104: 1648-1655; Hess D A, et al. (2006) Blood 107: 2162-2169). Recently, ALDH activity was detected in embryonic and adult mouse pancreas, specifically in adult centroacinar cells and terminal duct cells supposed to harbor endocrine and exocrine progenitor cells in the adult pancreas (Rovira M S, et al. (2010) Proc Natl Acad Sci USA 107: 75-80), and in pancreatic β cells (Yang I, et al., ALDH Is Expressed in G1 Phase Proliferating Beta Cells, PLOS ONE, May 2014, 9: e96204).

It has been discovered that as Foxo levels decline in β cells, ALDH1A3 levels are increased. Accordingly, in conjunction with this, a newly discovered subpopulation of ALDH+ (i.e. ALDH1A3$^{hi}$) islet β cells is reported herein. Based on their impaired insulin secretory properties and transcriptional signature, Applicant has determined that ALDH+ cells pertain to failing β cells. They show conjoined features of the two cardinal processes bookending β-cell failure: mitochondrial dysfunction and progenitor-like features. When β cells are subject to increased demand for insulin production, they increase cellular metabolism and substrate flux through mitochondria. Foxo is activated to maintain normal oxidative function and prevent cellular overwork. The tradeoff of increased Foxo function is increased Foxo degradation, leading to eventual loss of the protein.

The role of ALDH1A3 in β-cell failure will have to be determined through further studies. In oncology, there is no consensus on whether ALDH1A3 is a marker or a pathogenic factor in cancer progression. Applicant's data indicates that ALDH1A3 over-expression does not untowardly affect β-cell function, but these experiments don't capture the complexity of the potential roles of ALDH1A3 in β-cell failure. For example, ALDH1A3 could promote mitochondrial dysfunction—the paramount feature of ALDH+ cells—by activating RAR/RXR signaling via RA production. This can result in increased Pparα function, a feature of metabolically inflexible β cells. This effect may re-quire a specific duration or additional contributors, and would have gone undetected in the experiments carried out so far. Thus, elevated levels of ALDH1A3 are a harbinger, though not necessarily a cause, of β cell failure.

3. SUMMARY OF RESULTS

Using gene expression profiling of animal models of β-cell dysfunction, it was discovered that the progenitor cell marker aldehyde dehydrogenase 1 family member A3 (herein "ALDH1A3") (Marcato et al., 2011) was significantly elevated in dedifferentiated, non-insulin-producing or insulin-impaired β cells identified by the presence of cytoplasmic NKX6.1, showing that dedifferentiation entails regression to a progenitor-like stage. ALDH1A3 was highly up-regulated in several β-cell stress models including obese diabetic (db/db) (where the increase was more than 100-fold), diet induced obese (DIO), aging and triple knockout of FOXO1, 3a, and 4 in mature β-cells (β-triple FOXO) animals, as well as pancreatic progenitors. FOXO triple knockouts are known to be a faithful model of human Maturity Onset Diabetes of Youth (MODY), a genetic form of type 2 diabetes caused by an intrinsic abnormality of the β cell. The dramatic upregulation of ALDH1A3 expression in different models of type 2 diabetes showed that expression of this enzyme mirrored the progression of β-cell failure.

Elevated levels of ALDH1A3 expression are a marker for isolating β cells that are in the process of dedifferentiating or that have dedifferentiated to have impaired insulin production and secretion. Such isolated ALDH1A3$^{hi}$ cells can be used for example in screening assays to identify agents that reduce expression of ALDH1A3. The percentage of ALDH1A3$^{hi}$ cells detectable by flow cytometry in a pancreatic sample is indicative of the health of the pancreas from which the sample was taken. Healthy insulin-producing β cells have low levels of ALDH1A3 that are undetectable using flow cytometry. Therefore, as described above, flow cytometry can also be used to determine the percentage of ALDH1A3$^{hi}$ cells in a pancreatic sample to decide if an isolated pancreas or islets are healthy enough for transplantation into a human. The cutoff of about 3% or less ALDH1A3$^{hi}$ β cells in the total β cell population indicates healthy pancreas/islets, and a value above about 5% indicates unhealthy pancreas/islets that is/are not suitable for transplantation.

In light of recent suggestions that β-cell loss in type 2 diabetes is due to dedifferentiation, certain experiments were conducted in which pancreata from type 2 diabetic and non-diabetic human organ donors were surveyed to identify markers of dedifferentiation, changes in expression of insulin and other pancreatic hormones and protein expression. A near-threefold increase in the number of dedifferentiated human pancreatic islet cells that no longer produce any of the four major pancreatic hormones, yet retain endocrine features was seen in pancreata from Type 2 diabetics. Moreover, transcription factors FOXO1 and NKX6.1 that are known β-cell markers, were either decreased or mislocalized in β cells from diabetics. FOXO1 and NKX6.1 were ectopically located in glucagon+- or somatostatin+-immunoreactive cells of type 2 diabetics, respectively. These data show that insulin-producing β-cells become dedifferentiated and are consistent with the hypothesis that they undergo conversion to glucagon+- or somatostatin+-immunoreactive cells during the course of type 2 diabetes. Importantly, these findings are consistent with the findings from experimental animal models, showing that β cells are not permanently lost in human type 2 diabetics (Guo et al., 2013; Puri et al., 2013; Talchai et al., 2012; Taylor et al., 2013).

Figure 14A:
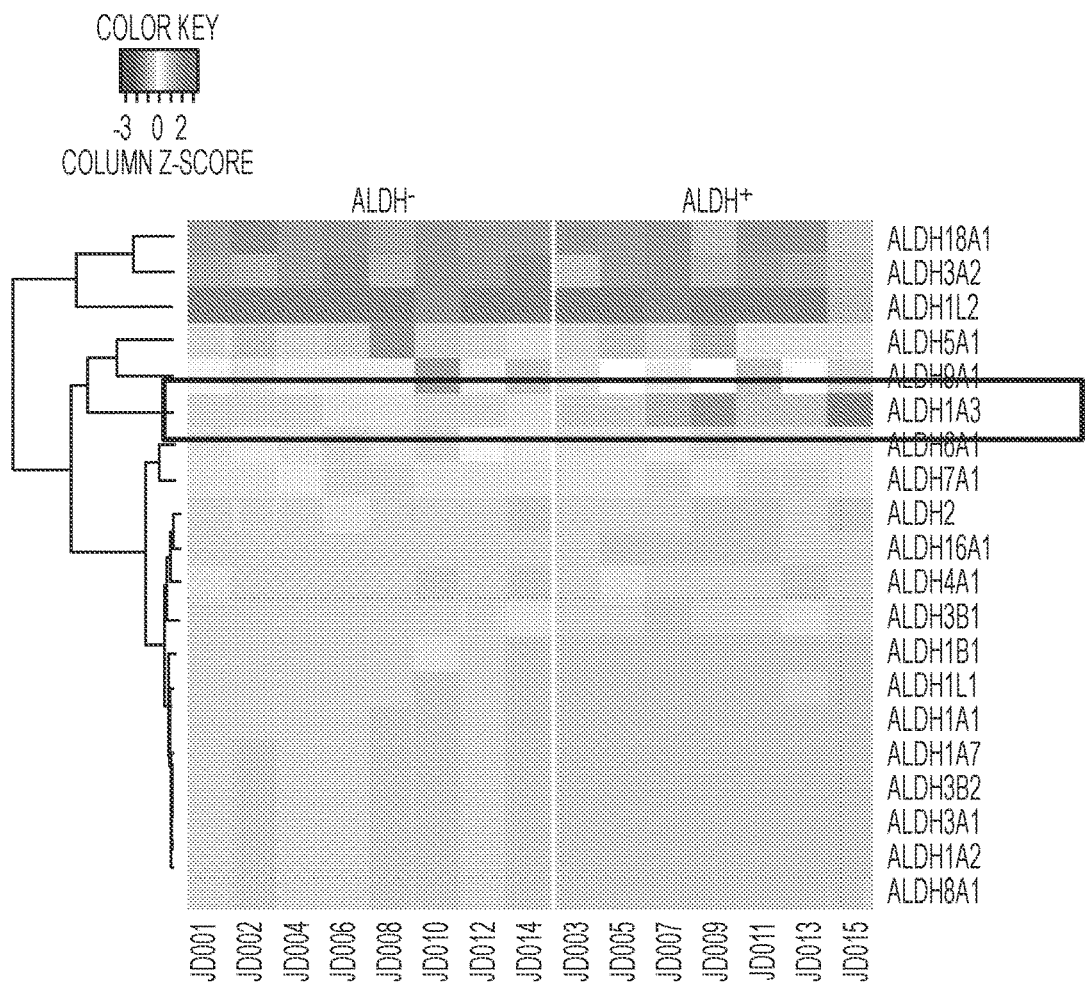
FIG. 14A-14B. Comprehensive analysis of ALDH isoform expression in flow-sorted ALDH+ and ALDH− cells.
Figure 14B:
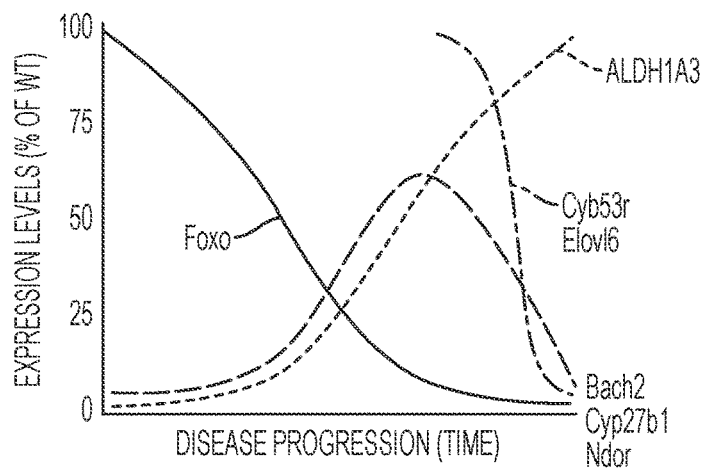

In the progression of the cellular pathology, mitochondrial complex I, IV, and V functions are impaired, leading to reduced ATP production, stalling of protein translation, and reactivation of genes that sustain a cellular progenitor program. When Foxo levels reach their nadir (a situation phenocopied by genetic knockout of Foxo), a further subset of genes becomes altered, including Cyb5r3, Elovi6, and Bach2 (FIG. 14B). Applicant proposes that these genes play a pathogenic role in β-cell dedifferentiation. Further studies to test their involvement in this process are underway, with the expectation that they are key mediators of progression of β-cell failure, and with the ultimate goal of developing therapeutic approaches to ameliorate β-cell dysfunction based on this model.

ALDH+ cells are strikingly enriched in selected lncRNAs: 6 of the 12 top differentially expressed transcripts belong to this category. At least three of these transcripts have previously been linked to human 3 cell dysfunction: Malat1, Meg3, and Kcnq1ot1. Malat1 is encoded in an enhancer cluster associated with 3 cell-specific transcription factors. Meg3 is part of an imprinted locus that confers susceptibility to type 1 diabetes and includes the atypical Notch ligand Dlk1, a negative regulator of adipocyte differentiation, as well as another gene, Rtl1, whose transcripts are also among the top enriched mRNAs in ALDH+ cells (Table 4). Finally, Kcn1qot1 is part of an imprinted locus that includes IGF2 and the Beckwith-Wiedemann locus and has been linked to type 2 diabetes susceptibility. It is not known what the targets are, let alone the functional consequences, of these changes in the lncRNA profile of ALDH+ cells, but we envision them to herald epigenetic changes leading to dedifferentiation.

In sum, the present work advances an understanding of β-cell failure and provides a series of testable targets to explain mechanisms of progression from impaired insulin secretion to cellular dysfunction and dedifferentiation.

The following is a summary of results of experiments described in the Examples of this application:

Pancreata from cadaverous human type 2 diabetes donors show increased β-cell dedifferentiation;

ALDH1A is dramatically increased, i.e., over 100-fold in dedifferentiated insulin-negative human islet endocrine cells;

ALDH1A3 was the most abundant isoform of the ALDH1 family in normal human pancreatic islets, with mean values of ALDH1A3 per islet three-fold higher in type 2 diabetics;

Cytoplasmic localization of NKX6.1 is a marker of dedifferentiating β-cells, and is therefore a marker of progenitor cells, as is ALD2A3;

Cytoplasmic NKX6.1 was observed in nearly 20% of ALDH1A3-positive cells in diabetics, which is a nearly fourfold increase compared to controls;

Aldehyde dehydrogenase 1A3 is increased in dedifferentiated β-cells in FOXO1, 3a and 4 Knockout mice;

Cells with high levels of ALDH1A3 expression showed low levels of insulin expression suggesting that β-cell dedifferentiation is associated with a substantial induction of ALDH1A3;

Acute overexpression of human ALDH1A3 in mice does not affect β-cell function and therefore increased ALDH1A3 was not a cause of β-cell dysfunction;

Elevated ALDH1A3 is a common feature of diabetic β cells;

ALDH1A3 overexpression does not impair insulin secretion; and

ALDH1A3 is a marker, rather than a cause of β cell dysfunction;

4. EMBODIMENTS

Isolation and Functional Characterization of ALDH1A3-Positive Islet Cells

A highly sensitive fluorescent assay using ALDEFLUOR™ can be used to identify cells that have ALDH activity. ALDEFLUOR™ is a non-immunological fluorescent reagent system that has supported over 1000 publications for the detection of aldehyde dehydrogenase-bright (ALDH$^{br}$) cells in over 80 different tissues. The ALDEFLUOR™ assay is provided by STEMCELL TECHNOLOGIES™ (Vancouver, Canada, Catalog #01700) High expression of ALDH has been reported for normal and cancer stem and progenitor cells of various lineages, including hematopoietic, mammary, endothelial, mesenchymal and neural cells. Only cells with an intact cellular membrane can retain the ALDEFLUOR™ reaction product, making this system selective for viable ALDH$^{br}$ cells. ALDEFLUOR™ is a non-toxic and easy-to-use kit that requires no antibody staining, and is compatible with standard cell sorters and analyzers. In certain experiments described in the Examples ALDEFLUOR™ was used to isolate ALDH1A3-high (ALDH$^{hi}$) cells from mouse islets in FOXO knockout mice. Importantly for embodiments of the invention that use ALDH1A3 as a marker of nonfunctioning β cells, ALDH1A3 expression in human pancreata was restricted to β-cells, and was not seen in other endocrine cell types. ALDH1A3 is the major isoform expressed in normal mouse pancreatic islets (FIG. 6(B)). Notably, ALDH1A3 but not ALDH1A1 was consistently increased in several β-cell stress models, including aging, diet-induced obese (DIO) animals, as well as db/db mice, a widely used model of obesity and diabetes with severe β-cell dysfunction, In some experiments red fluorescent protein (RFP) was used to label and isolate normal, insulin-producing β cells by cre-mediated recombination. Non-insulin-producing FOXO knockout Islet cells were incubated with ALDEFLUOR™ and selected for RFP (red) or ALDEFLUOR™ (green) fluorescence, yielding both RFP+-ALDH$^{low}$ normal β cells and ALDEFLUOR+-ALDH$^{hi}$ cells that are in the process of dedifferentiating into noninsulin-producing β cells or are dedifferentiated and have lost the ability to make and secrete insulin. ALDH$^{hi}$ and ALDH$^{low}$ cells were characterized by gene expression analysis and insulin secretion.

ALDH$^{hi}$ cells were found to be: (i) enriched in ALDH1A3; (ii) depleted of insulin and other markers of fully differentiated β cells; (iii) enriched in progenitor cell markers; and, (iv) depleted of Foxo (as ALDH1A3 levels rise when Foxo expression declines). Moreover, glucose-stimulated insulin release experiments conducted in ALDH$^{low}$ vs. ALDH$^{hi}$ cells, showed that only the former were glucose responsive. RNAseq analyses of non-β cells was conducted. Comparing ALDH$^{hi}$ with ALDH$^{hi}$ cells (including non-βcells) independent of Foxo genotype, revealed that the main differences lay in five pathways as shown below.

| Pathway analysis of ALDH$^{hi}$ cells | |
|---|---|
| Oxidative Phosphorylation | $5.28^{-25}$ |
| Mitochondrial Dysfunction | $9.68^{-22}$ |
| EIF2 Signaling | $1.48^{-13}$ |
| mTOR signaling | $2.13^{-11}$ |
| Regulation of eIF4 and p70S6K signaling | $1.32^{-09}$ |

Information and studies involving the FOXO knockout mice is set forth in Kim-Muller et al., Cell Metab, 2014 20(4):593-602, which is incorporated herein in its entirety.

Figure 11A:
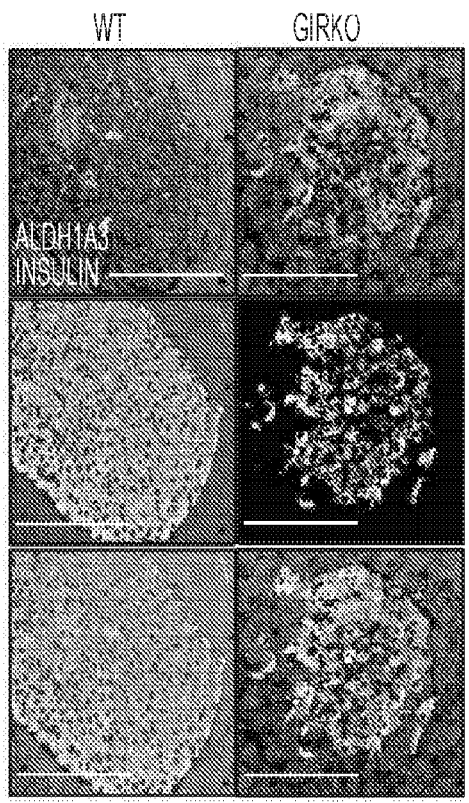
FIG. 11A-11G. Localization of ALDH1A3 In mouse Islets.
Figure 11B:
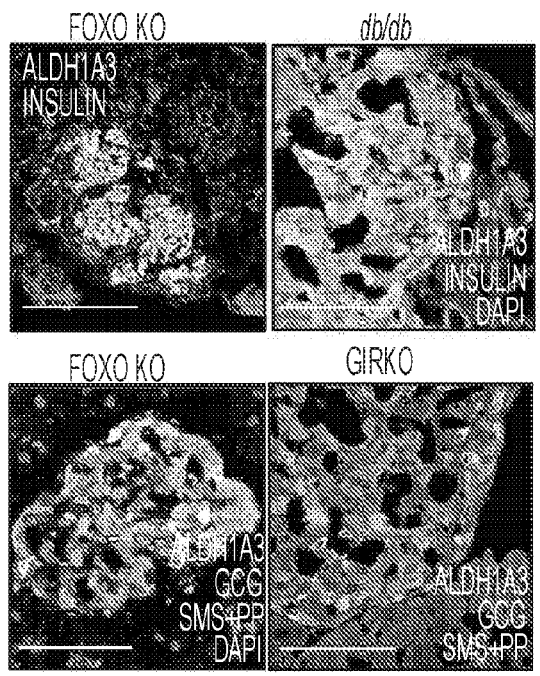

Elevated ALDH1A3 is a common feature of diabetic beta cells that have no or impaired insulin production and secretion. ALDH1A3 was localized in islets using immunohistochemistry. ALDH1A3$^{hi}$ cells were rare in normal islets (FIG. 11A). A classic model of diabetes secondary to extreme obesity was studied. db/db mice, as well as mice that develop diabetes as a consequence of extreme peripheral insulin resistance, brought about by targeted knockout of Insulin Receptor in muscle, fat, and brain (GIRKO) were studied. Of note, the latter mice are lean and have no intrinsic beta ell abnormalities, but develop diabetes as a result of their inability to compensate for insulin resistance. In both models, the number of ALDH1A3$^{hi}$ cells rose considerably (FIG. 11A-B). There was heterogeneity of immunohistochemical signal intensity among ALDH1A3-expressing cells. They were empirically defined for the purpose of immunohistochemical identification as ALDH1A3$^{low}$ and ALDH1A3$^{hi}$ cells. Further, ALDH1A3 immunoreactivity showed a reciprocal pattern with insulin immunoreactivity such that ALDH1A3$^{hi}$ cells were insulin-negative, while ALDH1A3$^{low}$ cells retained some insulin immunoreactivity (FIG. 11A-B). Strongly insulin-immunoreactive cells that were also ALDH1A3-positive were not detected, nor were any other endocrine cell types that co-localized with ALDH1A3 in mouse islets detected. ALDH1A3 overexpression did not impair insulin secretion. Other experiments showed that acute gain-of-function of ALDH1A3 didn't compromise beta cell function, suggesting that ALDH1A3 is a marker, rather than a cause of beta cell dysfunction.

Comparing Wild-Type Diabetic Pancreatic and Foxo Knockout ALDH$^{hi}$ Cells

ALDH1A3$^{hi}$ cells are a heterogeneous population of β cells at different stages of failure to make and secrete insulin in both beta cells of diabetic pancreata and Foxo KO. It was discovered that Foxo1 levels are low—but not absent—in wild-type ALDH1A3$^{hi}$ cells from human diabetic donor islets.

The dramatic elevation of ALDH1A3 in both wild-type diabetic β cells and Foxo1 knock outs shows that ALDH1A3 can be used as a marker for progression of β-cell dedifferentiation leading to impaired insulin production and β-cell dysfunction in diabetes, and as a means of identifying and isolating such cells. This result is extremely useful in that it enables one to easily select ALDH1A3$^{hi}$ β cells that are losing (dedifferentiating) or have lost the ability to make insulin (dedifferentiated) using a known and highly sensitive FACS method based on Aldefluor™. These dysfunctional ALDH1A3$^{hi}$ β cells are then subjected to high throughput screens against large numbers of test compounds to identify those agents that significantly reduce ALDH expression. Test agents that reduce ALDH in ALDH1A3$^{hi}$ β cells that have lost the ability to make and secrete insulin are expected to include agents that also cause the cells to differentiate back into insulin-producing β cells.

In an embodiment, genetically engineered cells that produce elevated ALDH1A3 can be generated, such as from stem cell lines, and implemented in embodiments of the invention to identify potential therapeutic agents as described herein. For teachings of specific methods for generating islet cells, U.S. Pat. No. 7,033,831 & U.S. Pat. No. 8,859,286 (issued to Viacyte) for creating pancreatic progenitor cells from somatic cells and U.S. Pat. No. 9,085,756 (issued to Asterias Biotherapeutics) for producing islet cell progenitors from human embryonic stem cells are incorporated herein by reference.

Drug Screening Assays

As used herein, "high throughput screening" refers to a method that allows a researcher to quickly conduct chemical, genetic or pharmacological tests, the results of which provide starting points for drug design and for understanding the interaction or role of a particular biochemical process in biology. High-throughput screening methods known in the art are used to screen thousands of new or known test agents to identify potential therapeutic drugs in vitro for their ability to induce noninsulin-producing β cells from a diabetic pancreas to produce and/or secrete insulin, which greatly accelerates drug development and renders it safer and cheaper than having to test all agents in biological assays. In certain embodiments, the high-throughput screening is accomplished in vitro. In an embodiment, the method is used to screen a library of compounds. In this context, the library of compounds may be composed of a plurality of chemical substances that may be assembled of multiple sources as is described below.

In the context of the present invention the term "screen" relates to a method in which a standardized molecular assay or a composition of several molecular assays is applied to a plurality of compounds to determine their properties of interest such as the particular ability to significantly reduce ALDH1A3 expression, as herein defined, in noninsulin-producing ALDH1A3$^{hi}$ β cells. A biological assay is also used in some embodiments to identify test agents that significantly increase insulin production and/or secretion in diabetic β cells. In some embodiments of the invention the screen is carried out on FACS-isolated ALDH1A3$^{hi}$ β cells. In other embodiments, the biological assay it is carried out on a diabetic or noninsulin-producing β-cell population, including islets or fragments thereof from a diabetic pancreas.

A screen may be carried out in solution, e.g., in flasks, reaction tubes, cuvettes, microtiter plates and the like, for example in a microarray format, or in a living animal excluding human or in a living pancreatic islets or isolated β cells. The screen may preferably be carried out with little compound consumption and/or small volumes. High throughput robotic screening on extremely few cells, sometimes even on a single cell, is preferred, therefore the use of a microtiter format is a typical implementation. On such a microtiter plate, small amounts such as only a few microliters may be sufficient for the screen.

In an embodiment, a high-throughput screening of the test agents identifies and selects those test agents that significantly reduce ALDH1A3 expression or activity in ALDH1A3$^{hi}$ β cells isolated from a diabetic pancreas, preferably detected by monitoring ALDH1A3 fluorescence using FACS. Identification and isolation of ALDH1A3$^{hi}$ cells in an embodiment is carried out by flow cytometry analysis, preferably with ALDEFLUOR™ as is described in the Examples. By "significantly reduces" ALDH1A3 expression or activity in a fluorescent assay is meant a statistically significant reduction that can be detected by fluorometer. In an embodiment the reduction is at least about 20% fluorescence. In another embodiment ALDH1A3 protein is assayed instead of fluorescence. In this embodiment "significantly reduces" ALDH1A3 protein expression in a protein assay is meant a statistically significant reduction in the level of protein detected in the assay.

In another embodiment, selected test agents that significantly reduce, as defined herein, ALDH1A3 are further tested in a biological assay in which diabetic beta cells (including for example whole diabetic islets or fragments of diabetic islets or isolated noninsulin-producing beta cells) in vitro are contacted with the selected test agent to see if it causes noninsulin-producing β cells to significantly increase expression and/or secretion of insulin. By "significantly increase" expression and/or secretion of insulin in a protein assay is meant a statistically significant increase of insulin protein detected in the assay. In an embodiment the increase is at least about 20%. It will be understood that the threshold for "significantly reduced" levels of ALDH1A3 and "significantly increased" insulin expression and/or secretion in embodiments of the invention may vary considerably depending on the experimental setup and may be adjusted depending on the experimental conditions.

If the test agent significantly increases insulin expression and/or secretion, it is a potential therapeutic agent eligible for further testing in vivo. The number of diabetic 1 cells needed for a biological assay to identify test agents that can significantly increase insulin production and or secretion varies in a range of from about 25, 50, 100, 200, 500, 1000 or 10,000 noninsulin-producing β cells. In even more specific example, a threshold diabetic beta-cell population is a whole or partially intact islet isolated from a mammalian pancreas, typically isolated from a diabetic human pancreas. In certain embodiments, one or more of the steps of the method are performed in the recited order.

In certain embodiments, the method further comprises testing the efficacy of a test agent that either significantly reduces ALDH1A3 in vitro or that increases insulin production and/or secretion in vivo, in an animal model such as db/db mouse or other diabetic animal.

In a preferred embodiment, the high-throughput screening is carried out in an automated format, particularly in a high-throughput format. In the context of the present invention, the term "automated format" refers to a method that is fully or partly controlled and/or carried out by one or more technical devices, preferably pipetting robots. In this context, the term "high-throughput format" relates to a screen/assay system for the rapid testing of a plurality of compounds within in a short time, thus, the screening/assaying time per tested compound is minimized. The initial screen of test agents is preferably carried out in multi-well plates in which the isolated ALDH1A3$^{hi}$ β cells are cultured, more preferably in E-well plates, 12-well plates, 24-well plates, 96-well plates or 384-well plates, even more preferably in 96-well plates or 384-well plates.

Biological assays for detecting insulin production and/or secretion for β cells or islets are known in the art and can be adapted for use in accord with embodiments disclosed herein. Test agents that have been shown to reduce ALDH1A3 levels according to embodiments disclosed herein can be further tested in a biological assay for their effects on insulin expression/secretion in diabetic β cells, for example in diabetic islets in vitro. See, for example, the following exemplary papers teaching insulin assay systems which are incorporated herein by reference. Walpita et al., A human islet cell culture system for high-throughput screening, *J Biomol Screen*. 2012 April; 17(4):509-18; D. Li et al., Imaging dynamic insulin release using a fluorescent zinc indicator for monitoring induced exocytotic release (ZIMIR), *Proc Natl Acad Sci USA*. 2011 Dec. 27; 108(52): 21063-8; and Rockann E. Mosser and Maureen Gannon, An assay for small scale screening of candidate β cell proliferative factors using intact islets, *BioTechniques*, Vol. 55, No. 6, December 2013, pp. 310-312.

Library

Test agents for use in screening encompass numerous chemical classes, though typically they are organic molecules, preferably small organic compounds having a molecular weight of more than 100 and less than about 2,500 daltons (Da), preferably less than about 500 Da. Some test agents comprise functional groups that permit them to structurally interaction with proteins, particularly hydrogen bonding, and typically include at least an amine, carbonyl, hydroxyl or carboxyl group, preferably at least two of the functional chemical groups. Such agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof. Libraries of high-purity small organic ligands and peptides that have well-documented pharmacological activities are available from numerous sources. One example is an NCI diversity set which contains 1,866 drug-like compounds (small, intermediate hydrophobicity). Another is an Institute of Chemistry and Cell Biology (ICCB; maintained by Harvard Medical School) set of known bioactives (467 compounds) which includes many extended, flexible compounds. Some other examples of the ICCB libraries are: Chem Bridge DiverSet E (16,320 compounds); Bionet 1 (4,800 compounds); CEREP (4,800 compounds); Maybridge 1 (8,800 compounds); Maybridge 2 (704 compounds); Maybridge HitFinder (14,379 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Set1 (5,056 compounds). Other NCI Collections are: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); SpecPlus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts: NCI Marine Extracts (352 wells); Organic fractions-NCI Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells). Compound libraries are also available from commercial suppliers, such as ActiMol, Albany Molecular, Bachem, Sigma-Aldrich, TimTec, and others.

The library may be fully randomized, with no sequence preferences or constants at any position. The library may be biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

The phrase "small organic" or "small inorganic" molecule includes any chemical or other moiety, other than polysaccharides, polypeptides, and nucleic acids, that can act to affect biological processes. Small molecules can include any number of therapeutic agents presently known and used, or can be synthesized in a library of such molecules for the purpose of screening for biological function(s). Small molecules are distinguished from macromolecules by size. The small molecules of this invention usually have a molecular weight less than about 5,000 daltons (Da), preferably less than about 2,500 Da, more preferably less than 1,000 Da, most preferably less than about 500 Da.

As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, mono-saccharides, di-saccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds. Collections of small molecules, and small molecules identified according to the invention, are characterized by techniques such as accelerator mass spectrometry (AMS; see Turteltaub et al., Curr Pharm Des 2000 6:991-1007, Bioanalytical applications of accelerator mass spectrometry for pharmaceutical research; and Enjalbal et al., Mass Spectrum Rev 2000 19:139-61, Mass spectrometry in combinatorial chemistry.)

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

"Compound" and "agent" are used interchangeably herein to describe any composition of matter including a chemical entity or a biological factor that is administered, approved or under testing as potential therapeutic agent or is a known therapeutic agent. Thus the term encompasses chemical entities and biological factors as defined, infra.

Any library of chemical compounds/agents available or generated by a person skilled in the art can be applied to methods of the invention to screen the provided compounds agents from the library for their ability to significantly reduce ALDH1A3 production in ALDH1A3$^{hi}$ β cells in isolated diabetic pancreas. Preferably, one or more compounds/agents are identified from a group of compounds, preferably from a compound library. As used herein the term "identifying a compound" may be understood as interchangeable with "detection of a compound" or "finding a compound." The term "identifying" herein may be understood as a relative term meaning that the test compound/agent has the desired biological activity of reducing ALDH1A3 levels in ALDH1A3$^{hi}$ β-cells isolated from a diabetic pancreas; or of increasing insulin production and/or secretion in noninsulin-producing β cells in a biologic assay. Test agents that increase inulin are potential therapeutic agents that warrant further in vivo testing.

Implantation/Transplantation of β Cells

Techniques for isolating and implanting pancreatic cells into a subject in need is known in the art. For example, Purified Human Pancreatic Islets (PHPI) Master Production Batch Record—*A Standard Operating Procedure of the NIH Clinical Islet Transplantation Consortium*; NIH-sponsored Clinical Islet Transplantation Consortium Phase 3 Trial: Manufacture of a Complex Cellular Product at Eight Processing Facilities Running title: NIH-CIT Phase 3 Trial-Islet Manufacturing Camillo Ricordil, et al. Further, a multicenter, single-arm, phase 3 study of the investigational product purified human pancreatic islets (PHPI) was conducted at eight centers in North America. Enrolled were 48 adults with T1D for >5 years, absent stimulated C-peptide, and documented Impaired awareness of hypoglycemia (IAH) and severe hypoglycemic events (SHEs) despite expert care. Each received immunosuppression and one or more transplants of PHPI, manufactured on site under good manufacturing practice conditions using a common batch record and standardized lot release criteria and test methods. The primary end point was the achievement of HbA1c<7.0% (53 mmol/mol) at day 365 and freedom from SHEs from day 28 to day 365 after the first transplant. The results showed that the primary end point was successfully met by 87.5% of subjects at 1 year, and by 71% at 2 years. The median HbA1c level was 5.6% (38 mmol/mol) at both 1 and 2 years. Hypoglycemia awareness was restored, with highly significant improvements in Clarke and HYPO scores (P>0.0001). No study-related deaths or disabilities occurred. Five of the enrollees (10.4%) experienced bleeds requiring transfusions (corresponding to 5 of 75 procedures), and two enrollees (4.1%) had infections attributed to immunosuppression. Glomerular filtration rate decreased significantly on immunosuppression, and donor-specific antibodies developed in two patients. Thus it was concluded that transplanted PHPI provided glycemic control, restoration of hypoglycemia awareness, and protection from SHEs in subjects with intractable IAH and SHEs. Phase 3 Trial of Transplantation of Human Islets in Type 1 Diabetes Complicated by Severe Hypoglycemia; DOI: 10.2337/dc15-1988. Other information known in the art for isolating and implanting/transplanting islet cells includes the following:

NIH-sponsored Clinical Islet Transplantation Consortium Phase 3 Trial: Manufacture of a Complex Cellular Product at Eight Processing Facilities, Ricordi, C et al. Diabetes. 2016 Jul. 27. pii: db160234. [Epub ahead of print].

Clinical Islet Transplantation Study, information provided on the protocols and SOPs providedat the isletstudy.org website address.

*Purified Human Pancreatic Islets (PHPI) Master Production Batch Record—A Standard Operating Procedure of the NIH Clinical Islet Transplantation Consortium*, CellIR4 2014; 2 (2): e891.

Hering et al., Phase 3 Trial of Transplantation of Human Islets in Type 1 Diabetes complicated by Severe Hyopglycemia, *Diabetes Care,* 2016 July; 39(7):1230-40.

5. EXAMPLES

It is proposed that dedifferentiating β cells undergo progressive loss of FOXO1 function, leading to altered localization (function) of other hormones that maintain 3-cell fate. This leads to dedifferentiation and in a subset of cells, conversion to other cell types. The pathogenesis of β-cell failure in type 2 diabetes is complex, as it integrates both qualitative (i.e., secretory) as well as quantitative (i.e., cell number) defects in insulin production, possibly spawning an inappropriate glucagon response (Dunning and Gerich, 2007; Polonsky, 2012).

The present findings provide correlative evidence for a role of FOXO1 in β-cell failure (Accili and Arden, 2004). FOXOs integrate insulin/hormone-dependent pathways with glucose/nutrient-dependent pathways in the pathogenesis of β-cell "stress" (Kitamura et al., 2005), thus providing a unifying mechanism explaining β-cell failure and offering a potential explanation for the benefits of glucose-lowering agents as well as insulin sensitizers on β-cell function (Defronzo et al., 2013).

The hypothesis that dedifferentiated cells lie quiescent and can be re-differentiated to produce insulin can explain why restoration of β-cell function is possible for years after the onset of hyperglycemia (Greenwood et al., 1976; Savage et al., 1979; Wajchenberg, 2007). However, it should be noted that the rapid onset of β-cell recovery is likely to also entail an amelioration of insulin secretion by residual β cells (Nauck et al., 1993). Applicant envisions dedifferentiation as a mechanism to protect β cells from apoptosis by stealth, preserving them for re-differentiation under more favorable metabolic conditions. This is consistent with a recent publication demonstrating that, in rodents, β-cell dedifferentiation can be reversed (Wang et al., 2014).

Example 1. Methods and Materials

Subjects

Pancreata were obtained from thirty diabetic organ donors. A summary of baseline characteristics of organ donors is reported in Table 1. Thirteen had a history of type 2 diabetes, one of drug-induced diabetes, and one of diabetes of unclear type. The fifteen controls were organ donors without a history of diabetes, with normal plasma glucose during their stay in the intensive care unit. Their features are reported in Table 2. The institutional review boards at Columbia University and at the University of Pisa have approved all procedures.

TABLE 1

Baseline Characteristics of Organ Donors

| Variable | Control | Diabetes | P |
|---|---|---|---|
| Number | 15 | 15 | NS |
| Gender (M/F) | 9/6 | 7/8 | NS |
| Age | 56 ± 18 | 66 ± 17 | NS |
| BMI (kg/m$^2$) | 26 ± 6 | 29 ± 6 | NS |
| Duration or diabetes | N/A | 12 ± 8 | N/A |

We present data as means ± SD.
We analyzed differences using Student's test.

TABLE 2

Summary of the features of dedifferentiated endocrine cells in type 2 diabetes

| Marker | β-cell | Dedifferentiated cell | Converted cell | α-cell |
|---|---|---|---|---|
| Insulin | ✓ | – | – | – |
| Glucagon | – | – | ✓ | ✓ |
| FOXO1 | ✓ | Cytoplasmic | Cytoplasmic | – |
| NKX6.1 | Nuclear | Cytoplasmic | Cytoplasmic | – |
| ARX | ✓ | – | + | + |
| ALDH1A3 | – | + | + | +/– |
| Syn, CgA | + | + | + | + |

Immunohistochemical and Morphometric Analyses

Tissue was fixed and processed for immunohistochemistry as previously described (Kitamura et al., 2009; Marchetti et al., 2007). The survey was focused on the head and neck region of the pancreas (Wang et al., 2013). Histochemical reactions in controls and diabetics were performed at the same time, using the same lot of antibodies at dilutions that Applicant tested to maximize sensitivity and minimize non-specific staining. Specifically, Applicant tested insulin antibodies at dilutions varying from 1:10,000 to 1:2,000 to identify the lowest possible dilution that allowed specific detection in β-cells. Applicant controlled each reaction by omitting the primary or secondary antibodies to determine the specificity of the signal. A list of antibodies is in the Methods section.

Frozen sections were obtained from samples collected at Columbia/Presbyterian Hospital to perform transcription factors analysis. Applicant applied antigen retrieval at pH 9.0 (Nacalai USA) to facilitate antigen retrieval and nuclear transcription factors detection. Applicant used Alexa-conjugated donkey secondary antibodies (Jackson Immunoresearch Laboratories and Molecular Probes) as described (Kitamura et al., 2009). Applicant used confocal microscopy and Laser Scanning Microscope Software (Zeiss LSM 510 and 710) to survey co-localization and capture images. Applicant performed the quantification in a blinded fashion using the CytoNuclear FL function of the HALO software to analyze individual cells in whole-slide fluorescent images. This tool scans images on multiple wavelengths corresponding to each fluorophor, locating cells and measuring the intensity of immunofluorescence against a preset standard. Each marker is measured in distinct cellular compartments, i.e. nucleus and cytoplasm. The analysis scores numbers of positive cells for each marker and calculates the number of cells showing co-localization of different markers. To perform quantitative analyses, Applicant scored at least three sections per donor and 5 islets per section.

Islet Isolation

Applicant purified islets by collagenase digestion followed by density gradient purification (Marselli et al., 2014). After isolation, Applicant cultured islets in a $CO_2$ incubator at 37° C. for 2-3 days, using M199 medium (EuroClone), containing 5.5 mmol/l glucose, supplemented with 10% (vol/vol) bovine serum, penicillin (100 U/mL), streptomycin (100 μg/mL), gentamicin (50 μg/mL), and amphotericin B (0.25 μg/mL) (Sigma-Aldrich).

RNA Extraction

Total RNA was extracted from batches of 100-120 hand-picked islets using the PicoPure RNA Isolation Kit (Arcturus, Mountain View, Calif.), adapted to cell pellets. Islets were rinsed with 1 ml of PBS, centrifuged them at 3,000×g for 5 minutes, resuspended them in 0.1 ml of extraction buffer, and incubated them at 42° C. for 30 min. Thereafter, samples were centrifuged at 3,000×g for 2 minutes and processed the supernatant for RNA isolation. Applicant removed genomic DNA by incubation with DNase I (QIAGEN, Germantown, Md.), and eluted the RNA in 30 μl of elution buffer. Applicant assessed RNA quantity and purity by absorbance at 260 and 280 nm, using the NanoDrop 2000C spectrophotometer and by testing samples on Nano LabChip of the Agilent 2100 Bioanalyzer (Agilent Technologies, Inc., Santa Clara, Calif.). The respective means±standard deviation of these parameters were: 51.1±21.8 ng/μl for the amount of RNA, 2.1±0.0 for the A260:A280 ratio, and 8.1±0.5 for the RIN value.

Reverse Transcription and qPCR

Quantitative analysis of FOXO1, MAFA and NKX6.1 transcripts was performed by real-time PCR, as described (Bugliani et al., 2013). Applicant synthesized cDNA templates from 200 ng of RNA using High-Capacity cDNA Reverse Transcription Kit (Applied Biosystems, Foster City, Calif.). TaqMan Fast Advanced Master Mix (Applied Biosystems) was used to perform real-time PCR, using 10 ng cDNA and 1 μl of TaqMan Gene Expression Assay (Applied Biosystems) in each well. Assays used were Hs01054576_m1 for FOXO1, Hs01651425_s1 for MAFA and Hs00232355_m1 for NKX6.1. Applicant used Importin 8 (IP08) as a reference transcript, and evaluated expression using the Hs00183533_m1 assay. Applicant performed PCR in the fast mode using the ViiATM 7 system (Applied Biosystems). For each sample, triplicate amplifications were performed and used average measurements for data analysis. Fold-differences in expression were determined by the 2-ΔΔCT method.

Statistical Methods

Two-tailed Student's t-test was used for data analysis and the customary threshold of $P<0.05$ to declare a statistically significant difference. Applicant presented quantitative data as means±SEM.

Animals

Genotyping was performed as described (Kitamura et al., 2009; Tsuchiya et al., 2012). Mice were maintained on a mixed 129J-C57BL/6 background. As controls, owing to the complexity of genotyping the 6 mutant alleles (five Foxo alleles and Rip-cre), Applicant used different combinations of FOXO1, 3 and 4 floxed mice without Rip-cre transgene or Rip-cre mice without FOXO floxed alleles (Xuan et al., 2002). These mice were indistinguishable from mixed 129J-C57BL/6 mice in all metabolic tests. All mice were fed normal chow and maintained on a 12-hour light-dark cycle (lights on at 7 AM). All experiments were performed in 12- to 20-week-old male mice, unless specified otherwise in figure legends. The Columbia University Institutional Animal Care and Utilization Committee approved all experiments.

Antibodies

The following primary antibodies were used: Synaptophysin (LsBio, LSC174787), NKX6.1 (DSHB, F55A12), Chromogranin A (Millipore, MAB5268), Glucagon (DAKO, A056501-2)(LsBio, LS-B4738)(TaKaRa, M182), Somatostatin (DAKO, A0566), Pancreatic Polypeptide (DAKO, A0619)(Millipore, AB939), Insulin (Santa Cruz-sc-9168) (DAKO, A056401-2), MAFA (Abcam, ab26405), FOXO1 (LsBio, LS-B4151), Arx (Millipore, MABN102), ALDH1A3 (Novus Biological, NBP2-15339).

Example 2

Figure 1B:
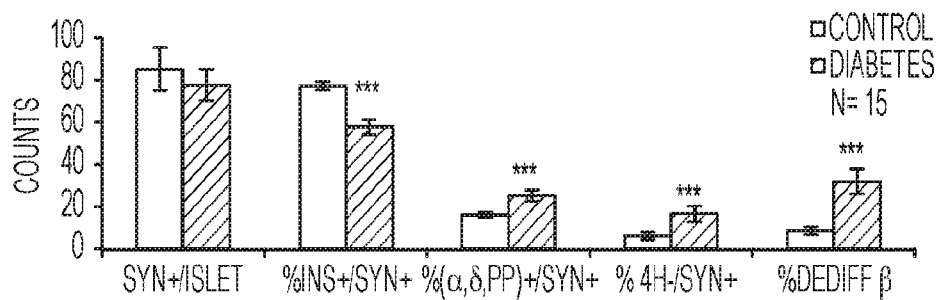
Figure 1C:
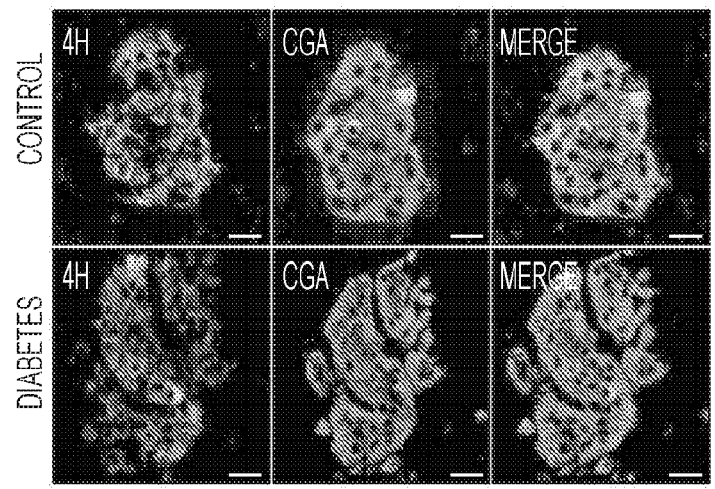

Pancreata from Cadaverous Human Type 2 Diabetes Donors Show Increased β-Cell Dedifferentiation Dedifferentiation in human pancreata from organ donors with and without diabetes was assessed. The head and neck of the pancreas were surveyed (Wang et al., 2013). Insulin-producing hormone-positive cells were scored using antibodies to insulin, glucagon (Gcg), somatostatin (Ssn), or pancreatic polypeptide (PP), and general endocrine cells were identified using antibodies to synaptophysin (Syn) (Talchai et al., 2012). In a subset of patients (n=5 for each group), the ratios of β-cells and α-cells were reexamined. A 32% decrease (from 77 to 53%) of insulin-positive cells was measured in diabetic human donors ($P<1\times10-6$), and a 68% increase of glucagon-positive cells (from 22% to 37%) ($P=0.009$) was seen, leading to a rise of the α/β cell ratio from 33% to 63% ($P=0.0002$) (FIG. 1A-C). In the complete cohort (n= 15 for each group), there were no differences in the number of Syn-positive cells per islet between the two groups (P=ns), indicating that there is no loss of β-cells with general endocrine features in type 2 diabetes (FIG. 1A, FIG. 1B). The percentage of Syn-positive/insulin-positive cells in diabetics decreased by 26% (57 vs. 77%) ($P<0.001$) (FIG. 1B). In contrast, the percentage Syn-positive and Gcg/Ssn/Pp-positive cells rose by 36% (16 vs. 25%) ($P<0.001$), and the percentage of all surveyed cells testing positive for Syn and negative for these four hormones decreased by 61% (6.5 vs. 16.8%) ($P<0.001$). When normalized by the number of β cells, the percentage of insulin-negative/Syn-positive cells actually rose by about 350% in diabetics, from 8.7 to 31% ($P<0.001$) (FIG. 1A, FIG. 1B).

Similar results were seen using Chromogranin A as a general endocrine marker (FIG. 1C). Notably there were large islet-to-islet variations within the same donor, with seemingly healthy islets lacking dedifferentiated cells mingled with islets that were characterized by extensive loss of hormone-positive cells. Islets with near-complete dedifferentiation, however, were unique to type 2 diabetics (Guo et al., 2013; Rahier et al., 2008). No statistically significant correlation between the dedifferentiation score (defined as the ratio of Syn-positive and hormone-negative cells to Syn-positive cells) and donors' age, body mass index, or duration of diabetes was seen. There was a weak trend for the association between dedifferentiation score and age among diabetics.

Example 3

The Progenitor Cell Marker Aldehyde Dehydrogenase 1A3 (ALDH1A3) is Dramatically Increased in Dedifferentiated Insulin-Negative Human Islet Endocrine Cells A key feature of β-cell dedifferentiation in animal models is regression to a progenitor-like stage (Talchai et al., 2012; Taylor et al., 2013; Wang et al., 2014). As described above, analyses of gene expression datasets in diabetic mice indicated that progenitor cell marker, aldehyde dehydrogenase 1A3 (ALDH1A3) (Marcato et al., 2011), is enriched in dedifferentiated islet endocrine cells. Thus, ALDH1A3 immunoreactivity was used to interrogate human pancreata to identify dedifferentiated β cells.

Figure 6B:
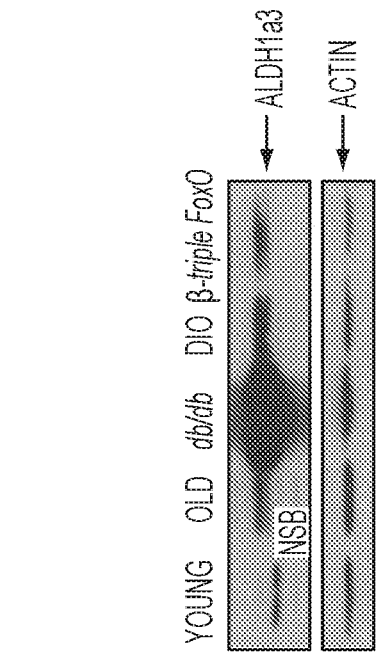
FIG. 6A-6D. ALDH1A3 is over-expressed in stressed β cells and αααα cells.
Figure 6A:
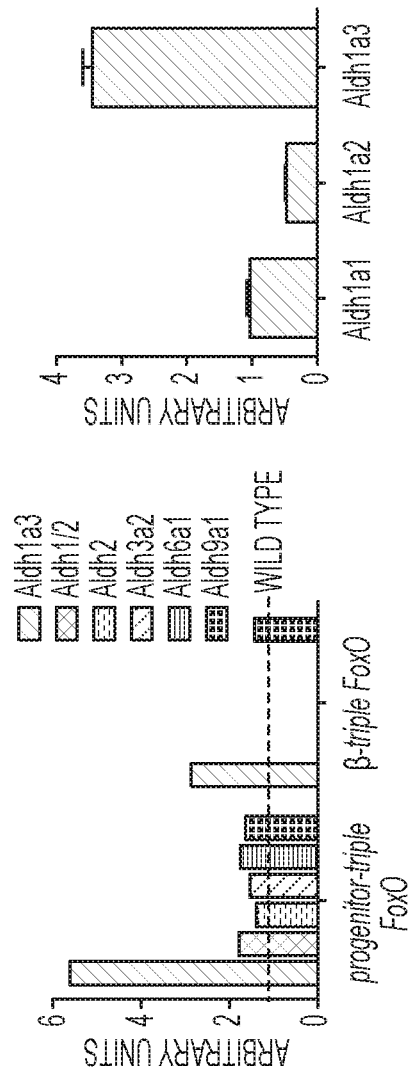
Figure 6D:
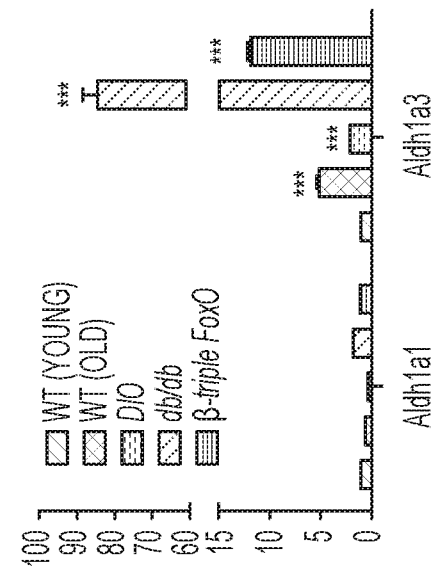
Figure 6C:
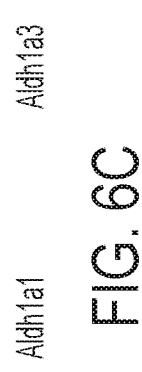

Within the ALDH1 family, ALDH1A3 is the major isoform expressed in normal mouse pancreatic islets (FIG. 6B). Notably, ALDH1A3 but not ALDH1A1 was consistently increased in several β-cell stress models, including aging, diet-induced obese (DIO) animals, as well as db/db mice, a widely used model of obesity and diabetes with severe β-cell dysfunction (FIG. 6C, FIG. 6D). An increase of over 100-fold in ALDH1A3 was seen in db/db mice (FIG. 6C) with no change in the expression of other isoforms (ALDH2, ALDH3a1, ALDH3a2, ALDH6a1, ALDH9a1 and ALDH7a1. Importantly for identifying potential therapeutic agents in embodiments of the invention, ALDH1A3 expression was inversely related to insulin expression, as was expected and acute overexpression of human ALDH1A3 in mice did not affect β-cell function.

Figure 2A:
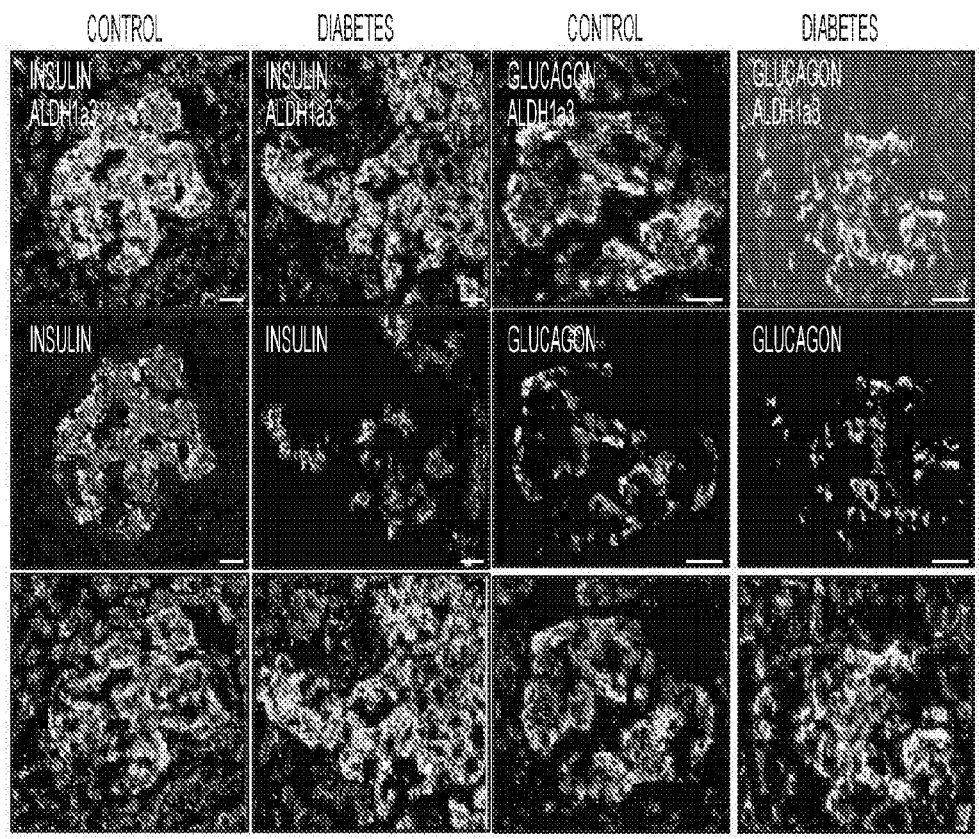
FIG. 2A-2D. ALDH1A3 Localization in Human Islets.
Figure 2B:
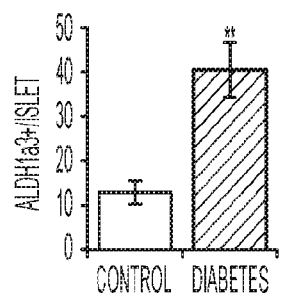
Figure 2C:
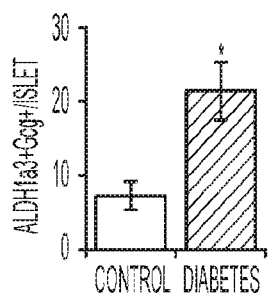
Figure 2D:
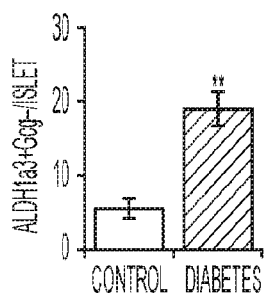

As in mice, the progenitor cell marker ALDH1A3 was the most abundant isoform of the ALDH1 family in normal human pancreatic islets, with mean values of ALDH1A3 per islet three-fold higher in type 2 diabetics than in controls ($P=0.01$) (FIG. 2B). Nearly 60% of ALDH1A3-positive cells in controls were also immunoreactive with glucagon, indicating that they are α-cells. The number of Gcg-positive/ALHD1A3-positive cells rose threefold in diabetics ($P=0.05$) (FIG. 2A, FIG. 2C). Importantly, 40% of ALDH1A3-positive cells were insulin-negative and Gcg-negative, which is consistent with their identity as progenitor-like cells. This critical population increased over threefold in diabetics compared to controls ($P=0.007$) (FIG. 2D).

Example 4

A Transcriptional Signature of Dedifferentiated β-Cells in Human Pancreata

The expression and localization of transcription factors required for maintenance of 1-(FOXO1, NKX6.1, and MAFA) was assessed (Guo et al., 2013; Talchai et al., 2012; Taylor et al., 2013). As reported, transcripts encoding the three proteins were decreased in diabetics (Guo et al., 2013). FOXO1 localization was restricted to β cells (Al-Masri et al., 2010) and its levels declined in type 2 diabetics, paralleling the loss of insulin immunoreactivity (FIG. 3(A)). NKX6.1 localized to the nucleus of β cells in control donors, whereas it localized to both nucleus and cytoplasm in 84% of insulin-positive cells in diabetics ($P<1\times10-5$) (FIG. 3B, FIG. 3C). Similar to NKX6.1, the subcellular localization of MAFA was altered in β-cells of diabetics, with diffuse cytoplasmic immunoreactivity (FIG. 3D). However, because MAFA is also found in a cells (Guo et al., 2013), subsequent analyses focused on FOXO1 and NKX6.1.

Figure 4A:
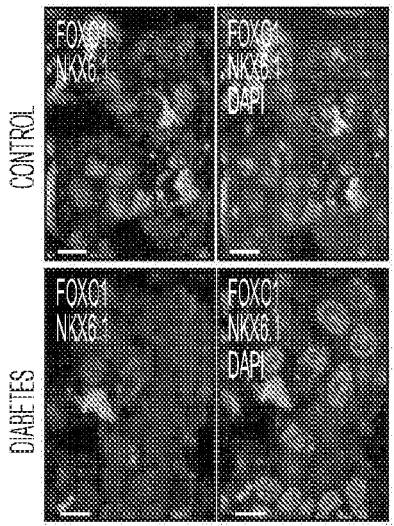
FIG. 4A-4E. Altered Localization of FOXO1 and NKX6.1 In Dedifferentiating β cells.
Figure 4B:
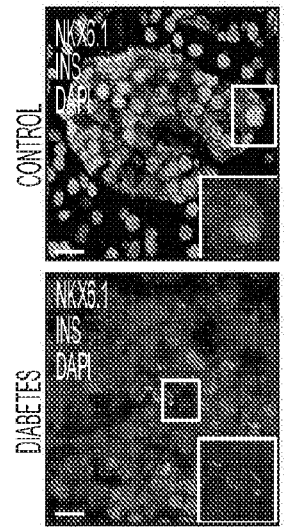
Figure 4C:
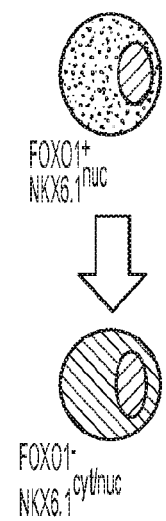
Figure 4D:
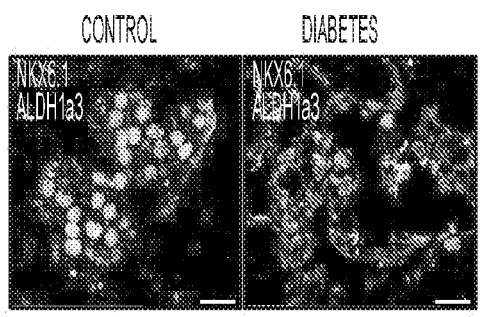
Figure 4E:
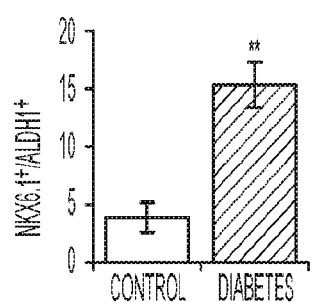

FOXO1 and NKX6.1 co-localized to the same cells in control donors, with NKX6.1 in the nucleus and FOXO1 in the cytoplasm (FIG. 4A). In contrast, pancreata from type 2 diabetics showed cells with cytoplasmic NKX6.1 that lacked FOXO1 immunoreactivity (FIG. 4A). Insulin-negative cells with cytoplasmic NKX6.1 were also observed (FIG. 13B). These cells might represent dedifferentiating β cells that have lost FOXO1, and are in the process of losing NKX6.1 (FIG. 4C). As these findings suggest, cytoplasmic localization of NKX6.1 is a marker of dedifferentiating β cells, and is therefore a marker of progenitor cells, as is ALD2A3. Cytoplasmic NKX6.1 was observed in nearly 20% of ALDH1A3-positive cells in diabetics, which is a nearly fourfold increase compared to controls (P=0.009) (FIG. 4D, FIG. 4E).

Example 5

Evidence of β-Cell Dedifferentiation to Other Cell Types

Figures 5A, 5B:
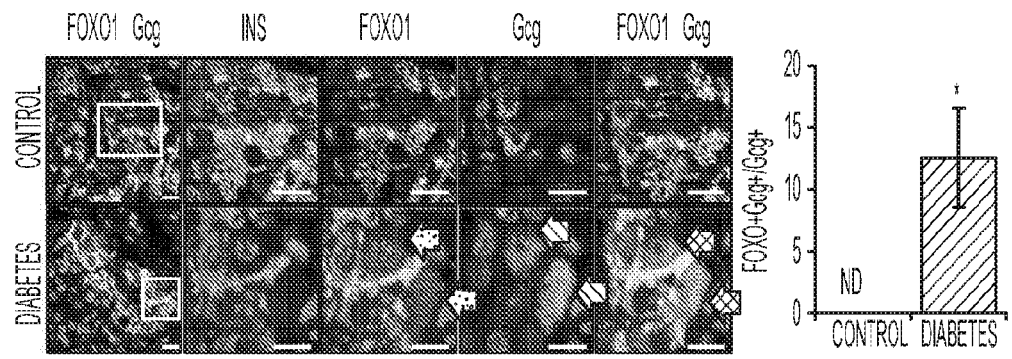
FIG. 5A-5F. Evidence of β-cell conversion to non-β-cells.
Figures 5C, 5D:
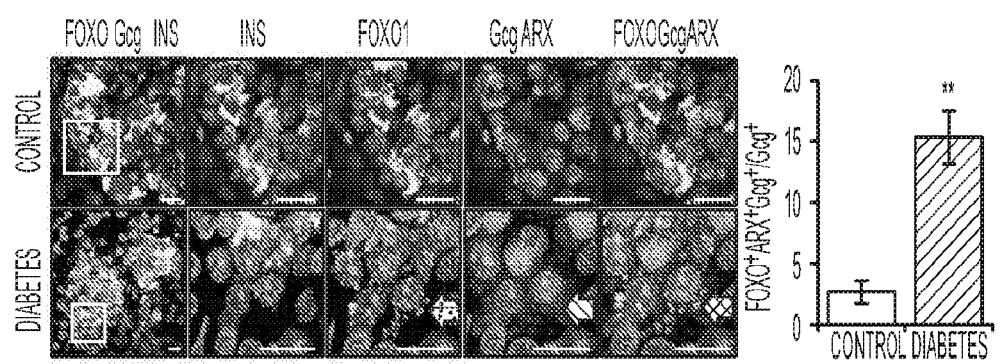
Figures 5E, 5F:
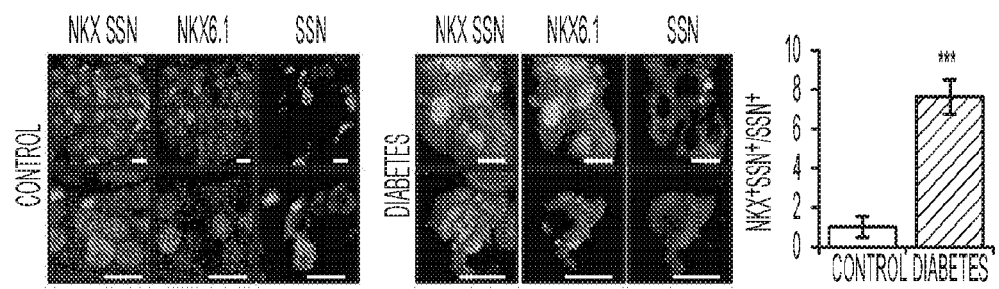

Type 2 diabetes is a state of relative glucagon overproduction (Henquin et al., 2011). It is unclear whether this can be explained by increased pancreatic α-cell mass or function. (Dunning and Gerich, 2007; Henquin et al., 2011; Yoon et al., 2003). Examination of the transcriptional profile of a cells in diabetics showed that up to 12% of glucagon-immunoreactive cells in human diabetic pancreata tested weakly positive for cytoplasmic FOXO1 immunoreactivity (P=0.05). Such cells were not detected in controls. The variance among our diabetic sample was entirely due to a single outlier with an inordinately high number of these cells (FIG. 5A, FIG. 5B). Furthermore, 15% of glucagon-positive/cytoplasmic FOXOβ cells scored positive for the α-cell transcription factor, ARX (Spijker et al., 2013) (P=0.005), which is a 7-fold rise compared to controls (FIG. 5C, FIG. 5D). Since cytoplasmic FOXO1 is inactive because it is a transcription factor, the findings are compatible with the explanation that these cells represent former β cells that, through loss of FOXO1 function, are undergoing conversion to glucagon-producing, "a-like" cells. There was no evidence of FOXO1 expression in β cells (data not shown). There was no evidence of NKX6.1 co-localization with glucagon, but 7.5% of somatostatin-positive cells also scored positive for cytoplasmic NKX6.1 (FIG. 5E, FIG. 5F) (P=0.001). These data are consistent with the possibility that as β cells lose NKX6.1 they convert to somatostatin-producing cells. No PP-positive cells were found that express either FOXO1 or NKX6.1 (data not shown).

Example 6

Aldehyde Dehydrogenase 1a3 is Increased in Dedifferentiated β Cells in FOXO1, 3a and 4 Knockout Mice Analysis of transcriptomes in mice showed that ALDH1A3 was significantly increased (p<0.05) in two models of diabetes where β cells are known to have dedifferentiated into non-insulin-producing cells: (i) mature pancreatic β-cell-specific FOXO1-, 3a- and 4-deficient islets (β-triple FOXO or RtKO); and (ii) pancreatic islets with triple FOXO1, 3a and 4 deletions at the pancreatic progenitor stage (progenitor-triple FOXO or PtKO). Among ALDH family members, the elevation of ALDH1A3 mRNA levels was the largest and most statistically significant (p<$10^6$, FDR<0.05) in triple FOXO knockouts (FIG. 6A). Within the ALDH1 family, ALDH1A3 is the major isoform expressed in normal mouse pancreatic islets (FIG. 6B). Notably, ALDH1A3 but not ALDH1A1 was consistently increased in several β-cell stress models, including aging, diet-induced obese (DIO) animals, as well as db/db mice, a widely used model of obesity and diabetes with severe β-cell dysfunction (FIG. 6C, FIG. 6D). An increase of over 100-fold in ALDH1A3 was seen in db/db mice (FIG. 6C) with no change in the expression of other isoforms (ALDH2, ALDH3a1, ALDH3a2, ALDH6a1, ALDH9a1 and ALDH7a1).

Example 7

ALDH1A3 Expression is Inversely Related to Insulin Expression

Figure 7A:
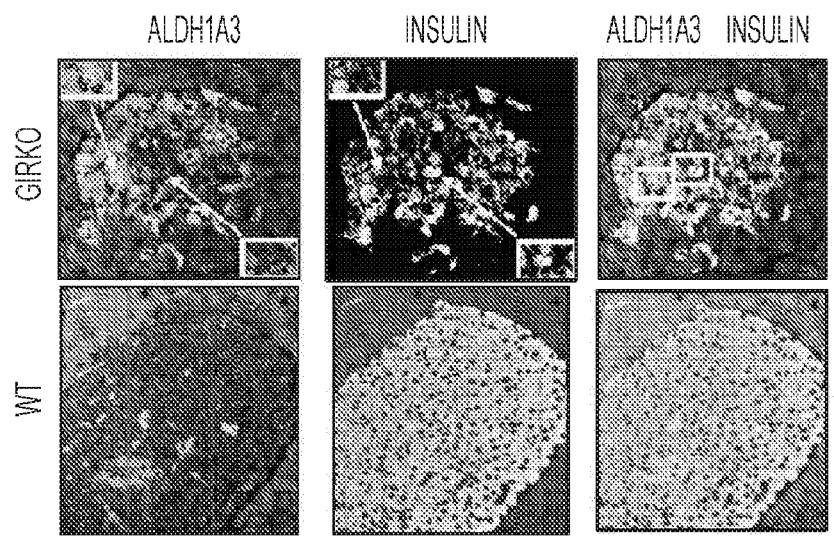
FIG. 7A-7B. ALDH1A3 expression in non-obese diabetic GirKO mice.
Figure 7B:
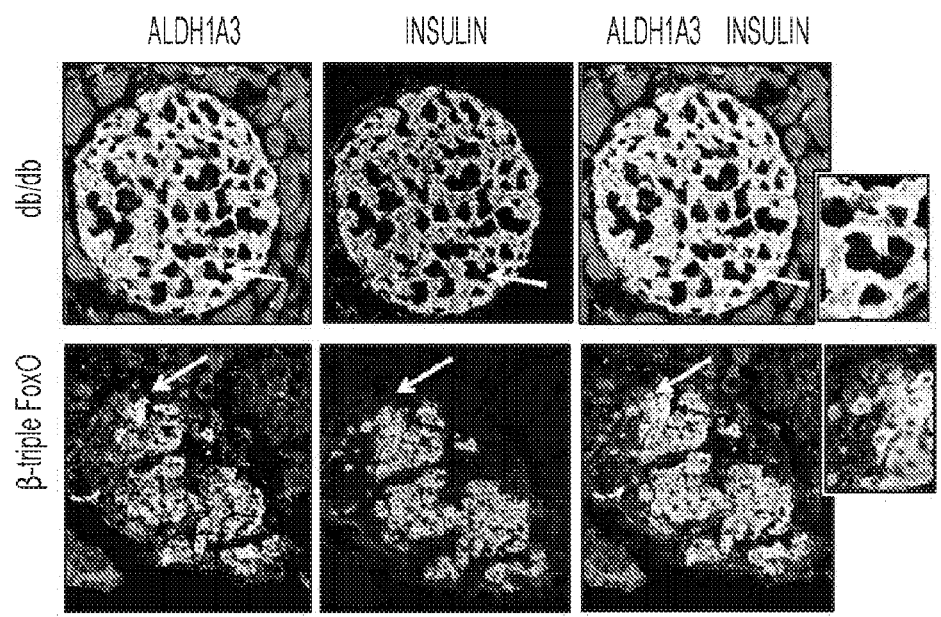

Using immunohistochemistry, most of endocrine cells expressing ALDH1A3 were β cells, judging by their immunostaining against insulin in several diabetic mice models. However, cells with high levels of ALDH1A3 expression rather showed low levels of insulin expression suggesting that β-cell dedifferentiation is associated with a substantial induction of ALDH1A3 (FIG. 7A, FIG. 7B).

Example 8

Acute Overexpression of Human ALDH1A3 in Mice does not Affect β-Cell Function

Figure 8A:
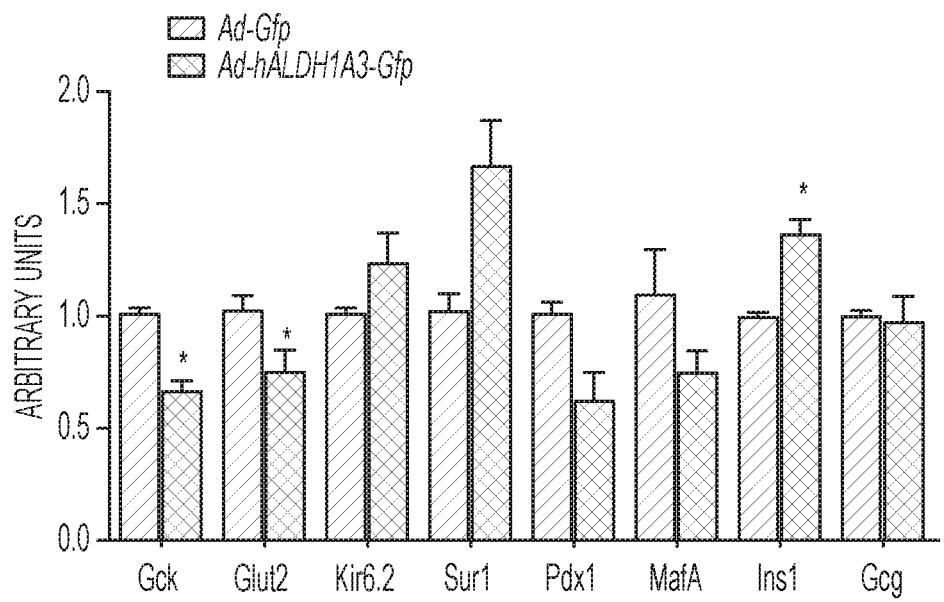
FIG. 8A-8B. Gene expression and Insulin secretion in hALDH1A3 overexpressing primary islets.
Figure 8B:
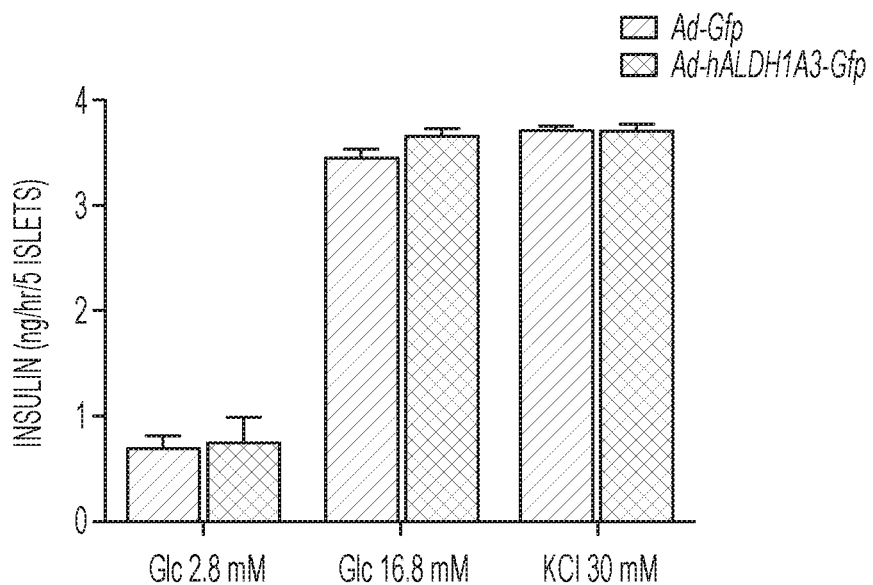
Figure 9:
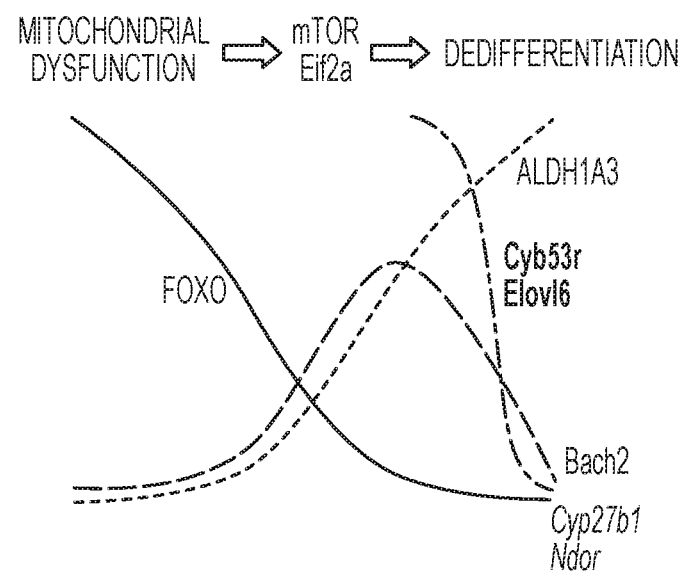
FIG. 9. Model. In diabetic β cells, mitochondrial dysfunction brings about changes in mTOR signaling, reduced protein synthesis, and dedifferentiation. These processes are associated with a gradual loss of Foxo function and a parallel increase in ALDH1A3 activity. As loss of Foxo progresses, there is a gradual increase in Pparα/γ activity. The former is pathogenic, the latter compensatory, as it attempts to draw acyl-CoA away from oxidation into FA synthesis. When Foxo levels bottom out, two key genes required for FA synthesis, Cyb5r3 and Elovl6, fail. At the same time, transcriptional repressor Bach2 is inactivated, leading to dedifferentiation.

To test whether the elevated ALDH1A3 expression/activity disturbed β-cell function, primary islets from wild type mice were transiently transduced with adeno-associated viral vectors to overexpress human ALDH1A3 (hALDH1A3). Expression of several key genes related to β-cell function was then measured by real time PCR and their response to GSIS (glucose stimulated insulin secretion) was assessed. A mild but significant reduction of Gck and Glut2 expression was seen, however expression of two key components of potassium channels (Kir6.2 and Surf) and Ins increased (FIG. 8A). Consistent with this observation, excess hALDH1A3 did not result in defects of insulin secretion in primary pancreatic islets (FIG. 8B). Thus, increased ALDH1A3 was not a cause of β-cell dysfunction.

Primary pancreatic islets are isolated from C57Bl6 mice to ectopically express Human ALDH1A3 (hALDH1A3). There is 94% protein sequence identity between mouse and human ALDH1A3 [18]). An adenoviral ALDH1A3-Gfp construct as well as control vectors are generated, (bare backbone vector, and Gfp-only). These viral vectors have already been packaged and amplified and are currently being titrated. Expression of Ad-Gfp-ALDH1A3 and control is tested with antibodies and confocal microscopy. >80% transduction efficiency, and 2- to 3-fold increase of ALDH proteins levels is achieved.

As described here, ALDH1A3 levels were dramatically increased in diabetic mice, especially in db/db mice (>100 fold induction in db/db beta cells), without any changes in the expression of other isoforms (ALDH2, ALDH3a, ALDH3a2, ALDH6a1, ALDH9a1 and ALDH7a1). ALDH1A3 has also been shown to be the major contributor to ALDEFLUOR™ oxidation in stem cells. The ALDEFLUOR™ method relies on the presence of ALDH1A1 and/or ALDH1A3 in R cells. Because ALDH1A3, and not ALDH1A1, is selectively induced in all of the models of β-cell dysfunction (FIG. 6B), it is expected that the ALDEFLUOR™ method can be used to identify the non-insulin-producing cells that express significantly increased levels of ALDH1A3 compared to insulin-producing β cells.

Example 9

Isolation of Pancreatic Islets and ALDH1a3$^{hi}$ Cells

An example of a method to isolate ALDH1A3 or ALDH1A3$^{hi}$ cells by FACS is as follows: Pancreatic cells can be perfused with 30 mg/dl collagenase (Sigma, China), and then incubated in a shaker (for example a 37 uC shaker for 30 minutes at a speed of 200 times per minute). After centrifugation, the pellet can be resuspended in Histopaque (Sigma) of a gravity of 1.12 for a subsequent gradient centrifugation at 1200 rpm for 20 minutes. The suspension fraction can be used for serial islet hand-pickings. Islet purity can be assured by absence of exocrine cell markers Sox9 and Amylase. Islets isolated from diabetic pancreata as just described are useful in embodiments of the invention to determine if a test agent that has been shown to reduce ALDH in noninsulin-producing ALDH1A3$^{hi}$ cells has the ability to increase insulin production and/or secretion in an in vitro bioassay.

To obtain a population of noninsulin-producing ALDH1A3$^{Hi}$ cells (that are not organized in islets), one uses the same method above to obtain islets (from diabetic pancreata) and then resuspends and digests the cells, for example with 10 mg/ml trypsin (Sigma) for 25 minutes, to prepare a single cell fraction for flow cytometry to isolate ALDH1A3$^{Hi}$/ALDH+ cells.

The ALDEFLUOR™ Kit (StemCell Technologies, Vancouver, Canada, Catalog #01700) is used according to the manufacturer's instructions to identify β cells that have dedifferentiated into non-insulin-producing high dysfunctional β cells that overexpress enzymatic activity ALDH1A3. Flow cytometry can be performed, for example, using a FACSAria (Becton Dickinson) flow cytometer. Pancreatic cells that overexpress ALDH1A3 (herein ALDH1A3+ cells) are then selected.

Techniques for conducting ALDEFLUOR™ assays and using FACS to isolate Aldh expressing are taught in Liu et al., *Histochem Cell Biol.* 2014 December; 142(6):685-91, Yang et al., *Mod Pathol.* 2014 May; 27(5):775-83. Such references are incorporated herein in their entirety.

Example 10

Elevated ALDH1A3 is a Common Feature of Diabetic β Cells.

Figure 10A:
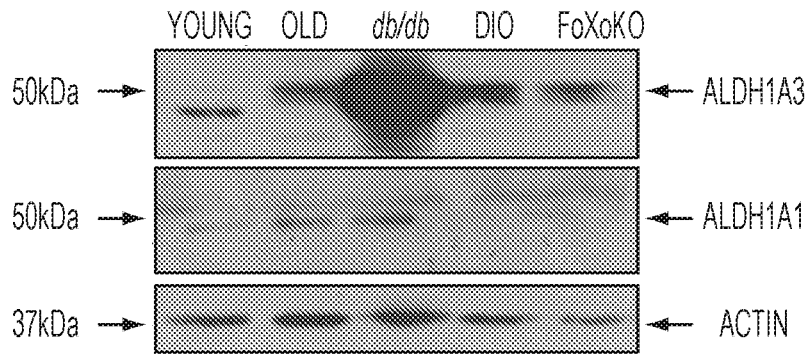
FIG. 10A-10C. Increased levels and activity of ALDH1A3 in diabetic mice.

Changes in gene expression during β-cell failure would be shared across multiple models of diabetes. Two permutations of a genetic approach involving triple Foxo knockouts (Foxo1, 3a, and 4) were used at two distinct developmental stages: (i) in pancreatic precursors (generated using Pdx1-cremediated gene knockout); (ii) in terminally differentiated b-cells (generated using Ins-cre). The triple Foxo knockout faithfully replicates human MODY, a genetic form of diabetes caused by an intrinsic β-cell abnormality 10. When Applicant compared transcriptomes of islets from these models, a narrow selection of genes was uniformly affected across the board. Among them was aldehyde dehydrogenase isoform 1A3 (ALDH1A3), expression of which increased 3- to 6-fold with robust adjusted p values (Table 3). The expression of ALDH1A3 was tested in other models of diabetes including aging, diet-induced, and db/db mutants, and found it to be increased too (FIG. 10A). Applicant sought independent confirmation of this observation in the literature, and found that similar increases of ALDH1A3 had been observed in diabetic Nkx6.1 and MafA knockout mice, as well as in a cross of diabetes-sensitive vs. resistant mice. ALDH1A3 is notably absent from normal β cells. In a recent study inspired by these findings, Applicant found that ALDH1A3 is also elevated in islets from patients with type 2 diabetes. ALDH1A3 had two attractive features that justified further studies: ALDH1 activity marks human cancer progenitor cells, and ALDH1A3 has been recognized as the isoform conveying increased ALDH1 activity in lung, ovary, breast, head and neck cancer, and melanoma.

Figure 10B:
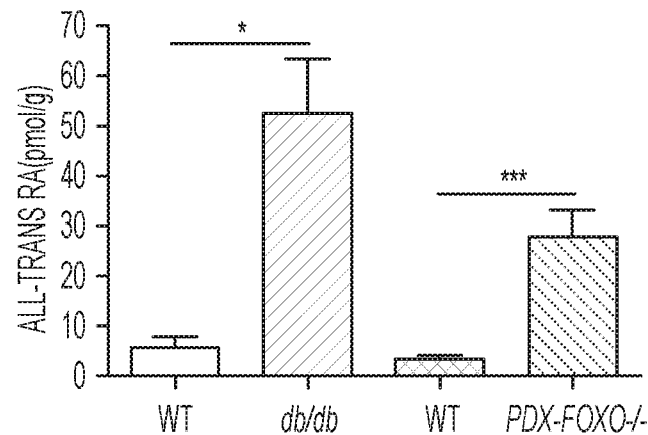
Figure 10C:
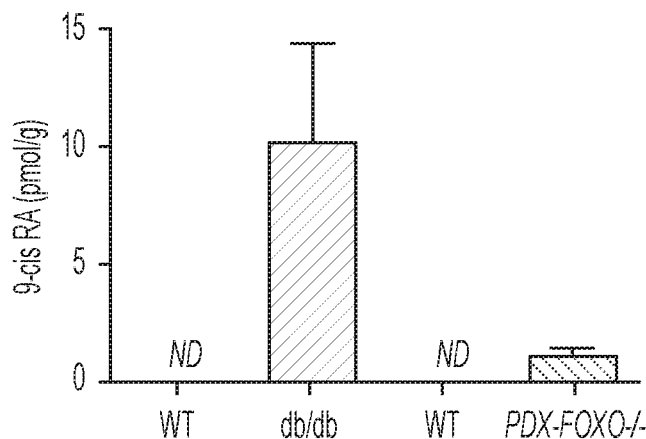

This observation is consistent with the notion that dedifferentiating β cells have progenitorlike features. Moreover, ALDH-expressing cells can be readily isolated using live cell assays. ALDH1A3 is one of 20 murine genes encoding NAD(P)+-dependent enzymes that catalyze aldehyde oxidation. ALDHs also have additional catalytic (e.g., esterase and reductase) and non-catalytic activities. ALDH1A3 is also known as retinaldehyde dehydrogenase (RALDH3) owing to its ability to synthesize retinoic acid (RA) from retinal. The increase was specific to ALDH1A3, as other isoforms showed little if any change (FIG. 10A). Measurements of all-trans-RA and 9-cis-RA production in islets confirmed a correlation between ALDH1A3 levels and RA generation, indicating that the enzyme is catalytically active (FIG. 10B, FIG. 10C). Applicant localized ALDH1A3 in islets using immunohistochemistry. ALDH1A3-positive cells were rare in normal islets (FIG. 11A). Applicant studied a classic model of diabetes secondary to extreme obesity, db/db mice, as well as mice that develop diabetes as a consequence of extreme peripheral insulin resistance, brought about by targeted knockout of Insulin Receptor in muscle, fat, and brain (GIRKO). Of note, the latter mice are lean and have no intrinsic R cell abnormalities, but develop diabetes as a result of their inability to compensate for insulin resistance. In both models, the number of ALDH1A3-expressing cells rose considerably (FIG. 11A, FIG. 11B). There was heterogeneity of immunohistochemical signal intensity among ALDH1A3-expressing cells.

Figure 11C:
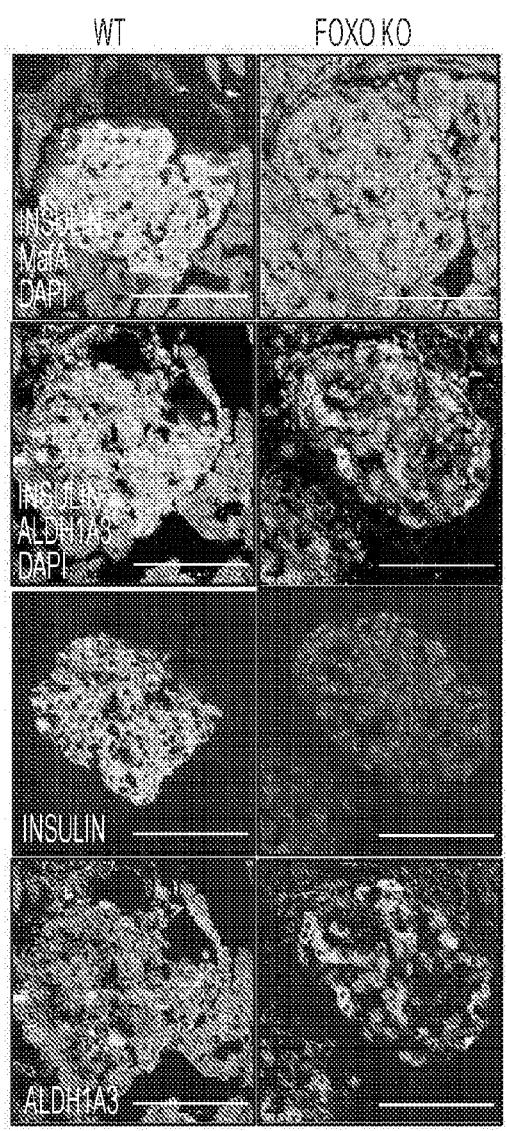
Figure 11D:
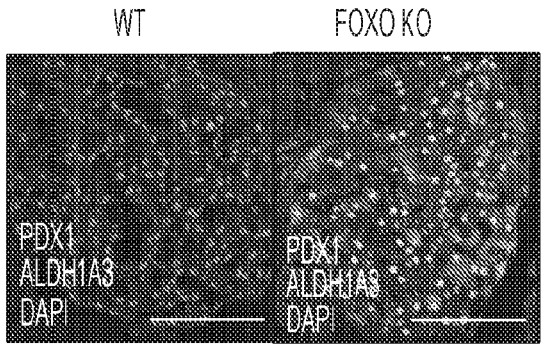
Figure 11E:
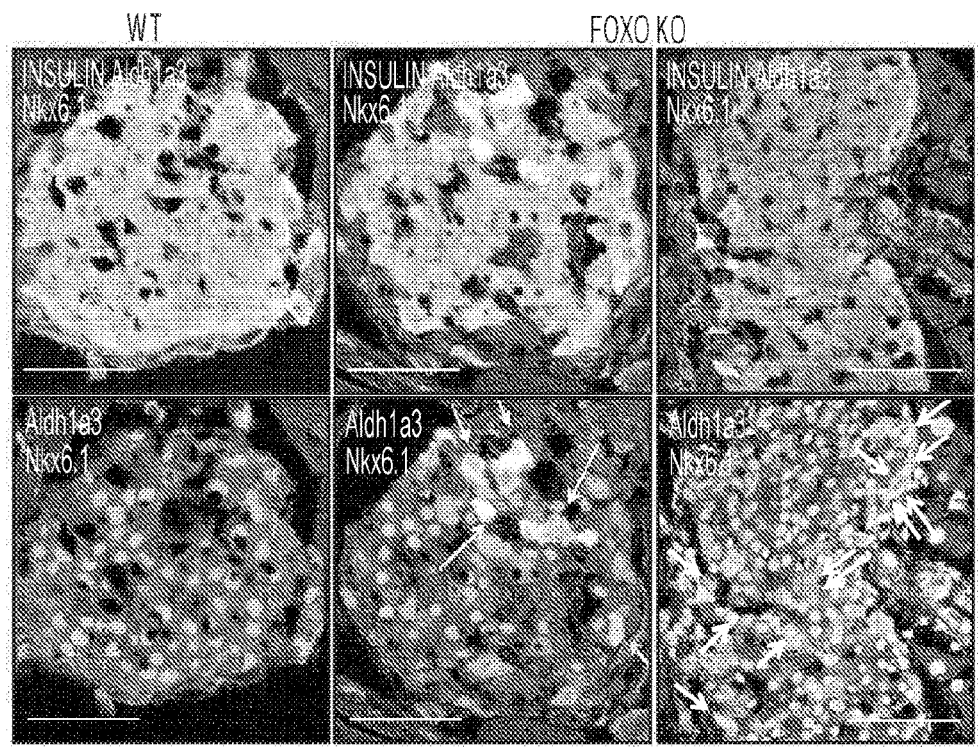
Figure 11F:
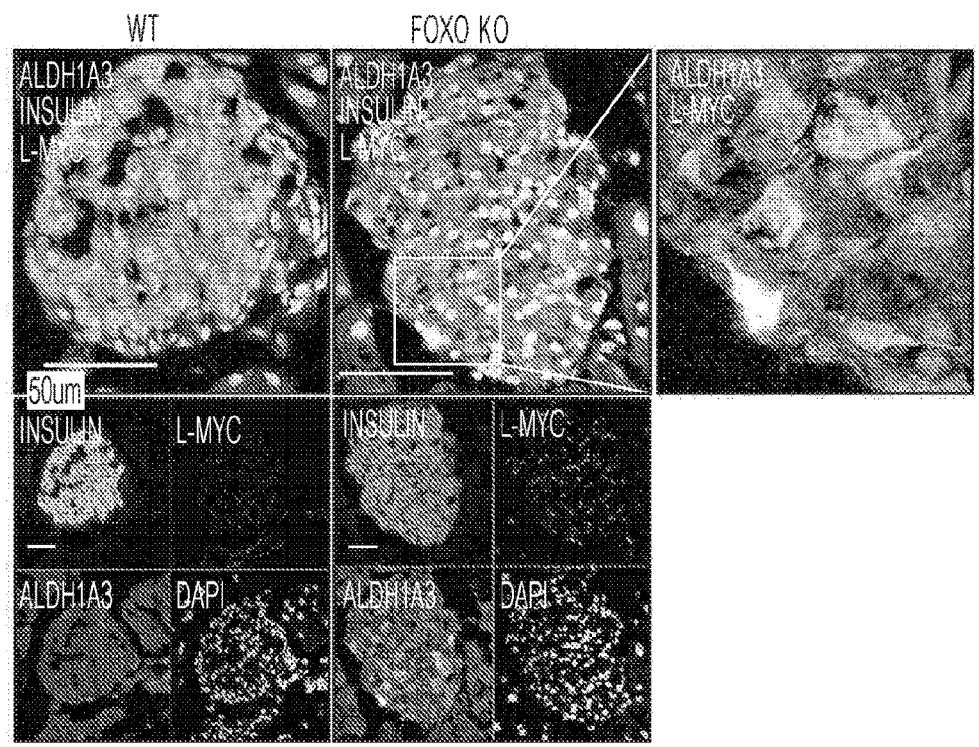
Figure 11G:
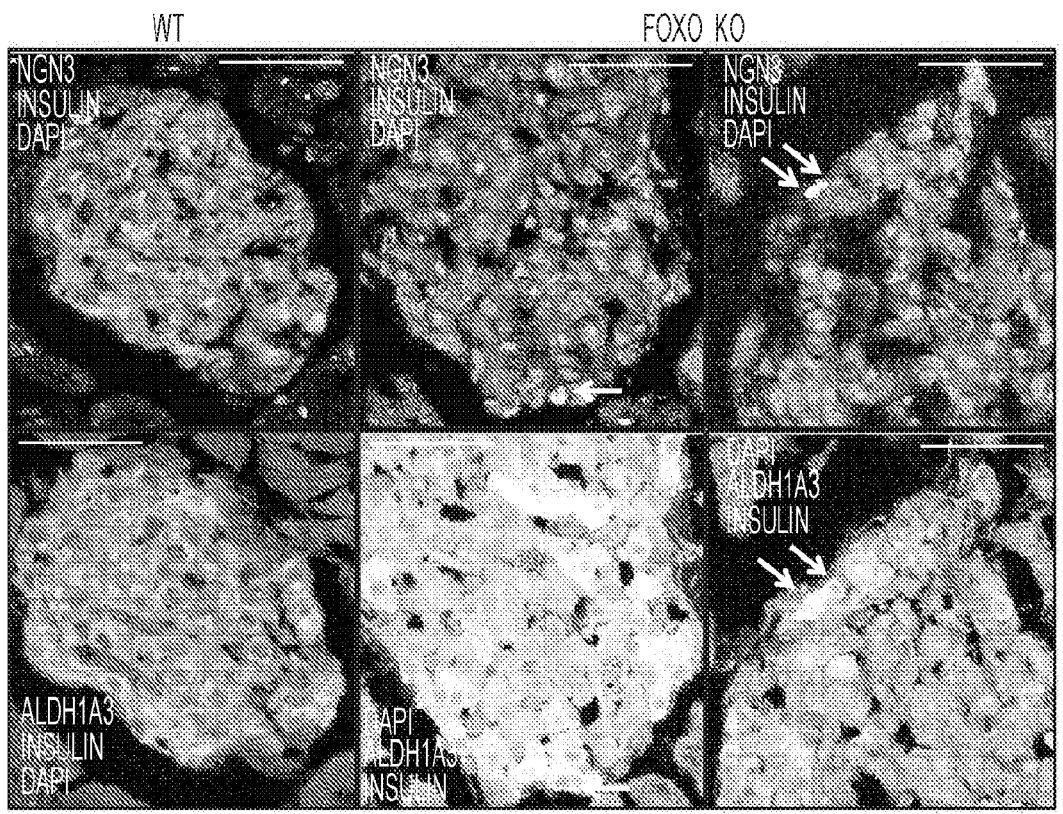
Figure 15:
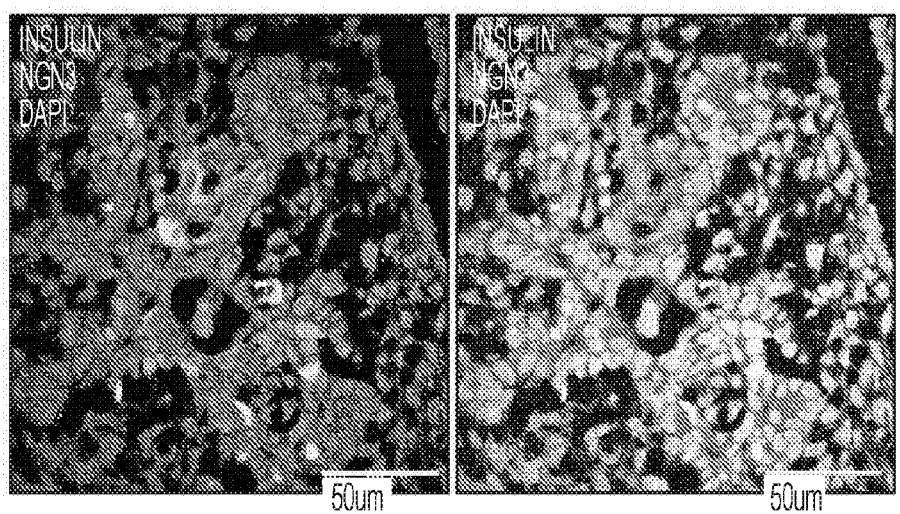
FIG. 15. Neurogenin3 localization in mouse E12.5 pancreas. Neurogenin3 immunohistochemistry in E12.5 mouse embryos.

ALDH1A3$^{low}$ and ALDH1A3$^{hi}$ cells were empirically defined. ALDH1A3 immunoreactivity showed a reciprocal pattern with insulin immunoreactivity such that ALDH1A3$^{hi}$ cells were insulin-negative, while ALDH1A3$^{low}$ cells retained some insulin immunoreactivity (FIG. 11A, FIG. 11B). Applicant did not detect strongly insulin-immunoreactive cells that were also ALDH1A3-positive, nor did Applicant detect any other endocrine cell type that co-localized with ALDH1A3 in mouse islets (FIG. 11B). These data show that ALDH1A3+ cells are heterogeneous and are comprised of insulin-producing cells as well as hormone-negative cells that can potentially represent a pro-genitor-like population. Applicant tested the expression of various β cell markers in ALDH1A3-positive cells. They had weak MafA immunoreactivity (FIG. 11C), but retained Pdx1 immunoreactivity (FIG. 11D). Nkx6.1 was generally reduced in ALDH1A3-positive cells (FIG. 11E), with Nkx6.1 absent in a subset of ~10% of ALDH1A3-positive cells (FIG. 11E, right panels, white arrows). Applicant also examined two progenitor cell markers, L-myc and Neurogenin3. Consistent with previous results, Applicant found that L-myc expression increased in Foxo knockout islets and that ALDH1A3-positive cells were L-myc-positive (FIG. 11F). Moreover, there was a subset of ALDH1A3+/Neurog3+ cells (FIG. 11G, white arrows). In Foxo knockout islets, ALDH1A3+/Neurog3+ cells accounted for 5.2% of ALDH1A3+ cells (7/134, n=9 sections from 3 mice) while in wildtype islets, we found no Neurog3+ cells and hence no ALDH1A3+/Neurog3+ cells. The staining method was validated in E12.5 fetal pancreas sections containing endocrine progenitors (FIG. 15). These data provide immunohistochemical evidence that ALDH1A3 marks a heterogeneous cell population, with features of incipient β-cell failure (reduced insulin), and includes a subset of dedifferentiating (low MafA or Nkx6.1) or dedifferentiated cells (L-myc and Neurog3-expressing).

Example 11

ALDH1A3 Overexpression does not Impair Insulin Secretion.

Figure 12A:
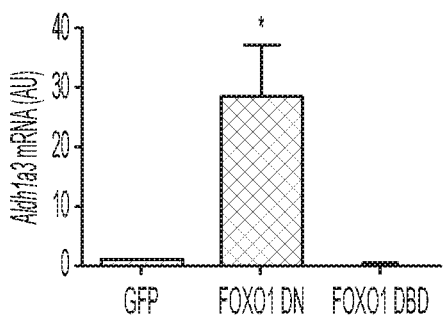
FIG. 12A-12G. ALDH gain-of-function in β cells.
Figure 12B:
Figure 12C:
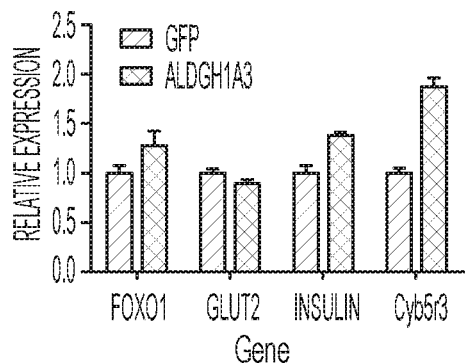
Figure 12D:
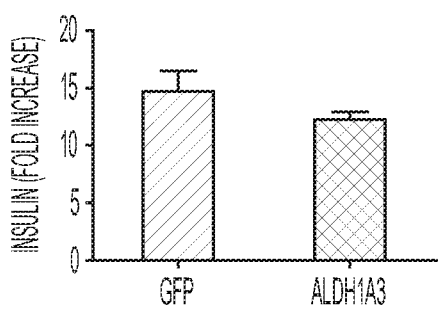
Figure 12E:
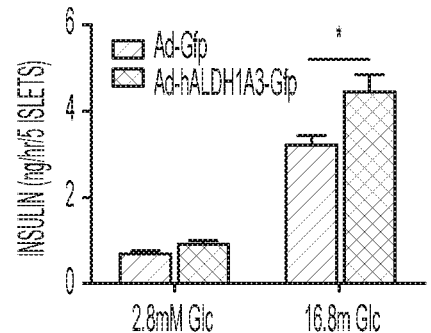
Figure 12F:
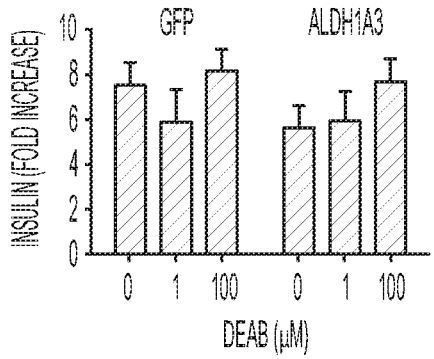
Figure 12G:
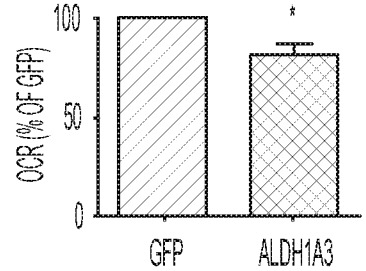

As Foxo1 loss-of-function is associated with increased ALDH1A3 levels, Applicant asked whether Foxo1 regulates ALDH1A3 in MIN6 insulinoma cells. Applicant transfected wild-type and two different mutant Foxo1 constructs to investigate this point. The first mutant is a dominant-negative that binds to DNA but lacks the transactivation domain, preventing binding of RNA polymerase, hence transcription. When overexpressed, it outcompetes endogenous Foxo (1, 3a, and 4) and effectively mimics the effect of a knockout 27. The second mutant, DNA-binding deficient (DBD), does not bind to DNA, and fails to activate Foxo targets for which DNA binding is required 28. Inhibition of Foxo1 by the dominant-negative mutant resulted in a ~30-fold increase in Aldh1a3 mRNA, while the DBD mutant Foxo1 failed to activate Aldh1a3 expression (FIG. 12A). This experiment shows that Foxo1 inhibits Aldh1a3 independently of DNA binding, likely acting as a co-repressor. These data are consistent with the possibility that activation of ALDH1A3 expression is an early correlate of reduced Foxo1 function. Reduced RA signaling in islets has been linked to defective insulin secretion. To test whether elevated ALDH1A3 activity affects β cell function, Applicant overexpressed ALDH1A3 in MIN6 cells using either transient transduction with adenovirus (FIG. 12B) or the derivation of stably transfected clones, and then measured expression of genes that are important for β-cell function or glucose-stimulated insulin secretion. In either case, no defects were found in gene expression (FIG. 12C) or insulin secretion (FIG. 12D). Moreover, Applicant transduced islets of wild-type C57Bl/6J mice with ALDH1A3 adenovirus and found a small, but statistically significant increase of glucose-induced insulin secretion (FIG. 12E). ALDH1A3 activity can be inhibited by the irreversible inhibitor N,N-diethylaminobenzaldehyde (DEAB) 25. Insulin secretion experiments were performed in MIN6 cells overexpressing ALDH1A3, in the presence of DEAB. But Applicant did not detect an effect of this compound to change insulin secretion (FIG. 12F). Finally, oxygen consumption was measured in MIN6 cells overexpressing ALDH1A3 as a surrogate of mitochondrial function, and found a modest decrease (FIG. 12G). However, in light of the fact that insulin secretion was normal (in MIN6) or slightly elevated (in primary islets), that this slight oxidative defect is unlikely to result in a functional change. These data showing that acute gain-of-function of ALDH1A3 doesn't compromise β-cell function suggest that ALDH1A3 is a marker, rather than a cause of β-cell dysfunction.

Example 12

Isolation and Characterization of ALDH1A3-Expressing Islet Cells.

Figure 13A:
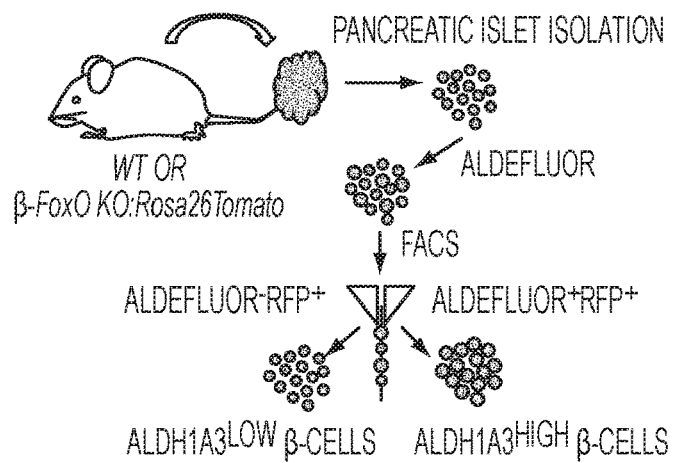
Figures 13B, 13C:
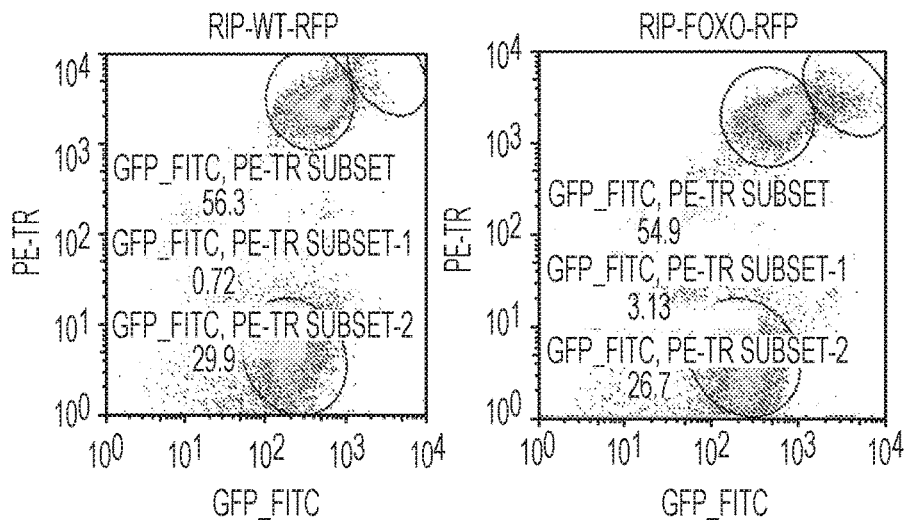
(FIG. 13B and FIG. 13C) Experimental validation. Islets from 6-month-old β cell-specific (Rip-cre) Foxo knockouts and littermate controls were sorted as described. The different circles denote the three cell populations used in further studies: RFP−ALDH−, RFP+ALDH−, and RFP+ALDH+.
Figure 13D:
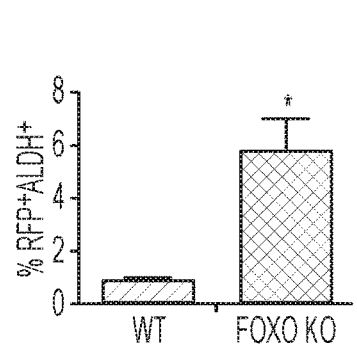
(FIG. 13D) Quantification of RFP+ALDH+ cells in repeated sorts (n=5) of wild-type and Rip-Foxo knockout animals.

An assay of ALDH activity was used to isolate ALDH1A3-expressing cells from mouse islets (FIG. 13A). The activated ALDEFLUOR™ reagent, BODIPY™-aminoacetaldehyde (BAAA) is a cell permeable fluorescent ALDH substrate is metabolized to the non-releasable derivative BODIPYT-aminoacetate (BAA) in the presence of ALDH, thus permanently labeling ALDH-expressing cells. Applicant used red fluorescent protein to label β (or former β) cells by cre-mediated recombination. Thereafter, Applicant incubated cells with ALDEFLUOR™ r, and selected for RFP (red) and ALDEFLUOR™ (green) fluorescence, yielding ALDH- and ALD$^+$ cells. The latter should include dysfunctional/dedifferentiating β cells. In wild-type mice, Applicant obtained three subpopulations: RFP$^-$ALDH$^-$ (non-β cells), RFP$^+$ALDH$^-$ (healthy β cells), and RFP$^+$ALDH$^+$ (dysfunctional β cells) (FIG. 13B). The latter represented less than 1% of total cells in normal islets. In separate experiments, RFP$^+$ALDH$^+$ cells were isolated from animals with β-cell-specific (Ripcre) triple-Foxo1 knockouts. As predicted, the RFP$^+$ALDH$^+$ sub-population increased about 7-fold in this model (FIG. 13(C)-13(D)).

Figure 13E:
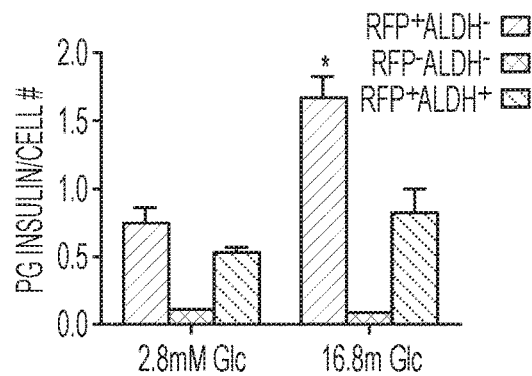
(FIG. 13E) Insulin secretion in RFP−ALDH− (GFP_FITC, PE TR subset 2), RFP+ALDH− (GFP_FITC, PE TR subset), and RFP+ALDH+ (GFP_FITC, PE TR subset 1) cells isolated from wild-type and Rip-Foxo knockout mice (n=3).
Figures 13F, 13G, 13H:
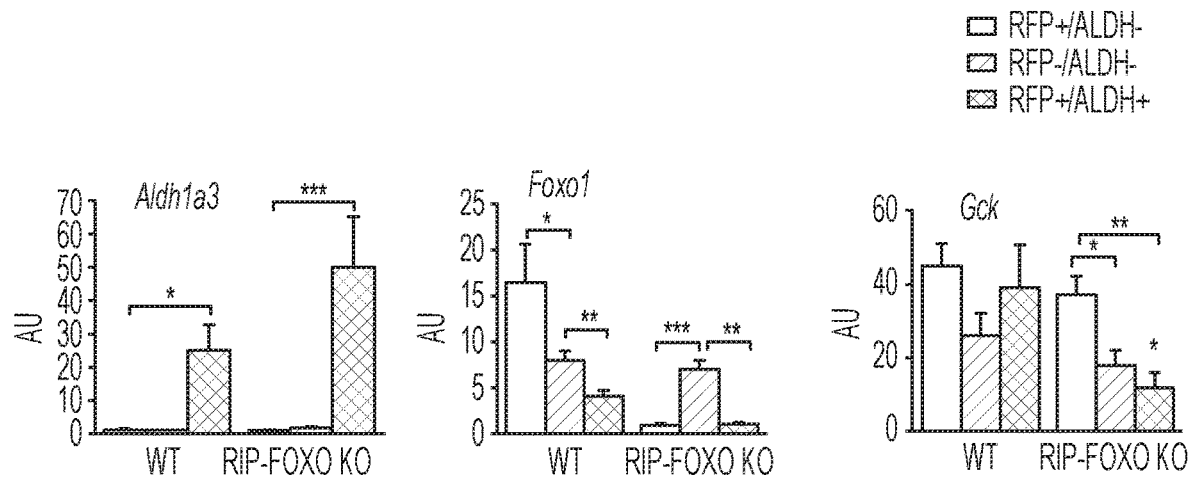
Figures 13I, 13J, 13K:
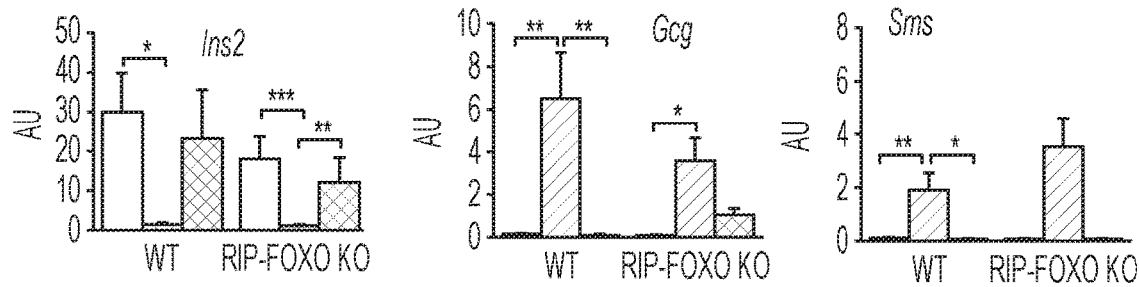
Figures 13L, 13M, 13N:
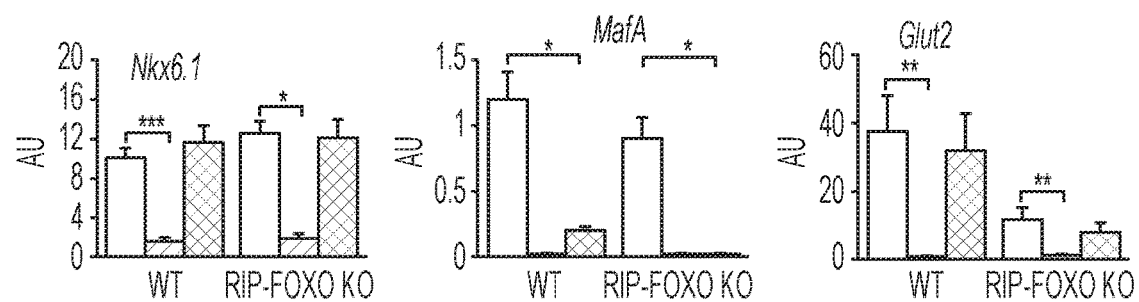

Applicant performed a preliminary characterization of ALDH- and ALDH cells by measuring insulin secretion and gene expression. The predicted outcome of these experiments was that ALDH$^+$ cells would be: (i) enriched in ALDH1A3; (ii) impaired in their ability to secrete insulin; (iii) depleted of markers of functional β cells, including Foxo1. All predictions were borne out by the data. In glucose-stimulated insulin release experiments using ALDH$^-$ vs. ALDH$^+$ cells, Applicant found that only the former responded to glucose, providing evidence for a functional impairment of ALDH$^+$ cells (FIG. 13E). Aldh1a3 mRNA was restricted to the RFP$^+$ALD$^+$ population in both wildtype and triple Foxo knockout mice (FIG. 13F). Foxo1 was reduced by ~70% in ALDH+ cells from wild-type mice (FIG. 13G). Glucokinase was nearly equally represented in all fractions, but was decreased in ALD$^+$ cells of triple Foxo knockouts (FIG. 13H), similar to previously reported single knockouts 7. Insulin2 and Nkx6.1 expression were greatly enriched in the RFP population, while glucagon and somatostatin were enriched in the RFP$^-$ population (FIG. 13I), providing another key element to support the identity of these cells. Foxo1 target MafA was enriched in the RFP$^+$ALDH$^-$ population and drastically reduced in RFP$^+$ALDH$^+$ cells. These data are consistent with the notion that ALDH$^+$ cells are β cells that have lost key functional features (FIG. 13M). Finally, Glut2 expression was restricted to RFP$^+$ cells, regardless of their ALDH status, and was significantly decreased in Foxo knockouts, consistent with prior findings (FIG. 13N).

Example 13

Transcriptome of ALDH$^+$ Cells and Progression of β Cell Failure.

RNA sequencing analyses were carried out comparing ALDH$^+$ with ALDH$^-$ β cells (RFP$^+$), as well as other islet cell types (RFP$^-$) in wild-type mice. Moreover, wild-type ALDH$^+$ cells were compared with triple Foxo-deficient ALDH$^+$ cells generated by knocking out Foxo in mature cells. As a quality control, expression of all 20 Aldh transcripts was studied, and found that only Aldh1a3 showed differential expression in the ALD$^+$ population (FIG. 14A). Moreover, in all comparisons between ALDH$^+$ and ALDH-cells, Aldh1a3 was among the top differentially expressed genes (Tables 7 and 8). This finding confirms the specificity and robustness of the enrichment technique. First, differences in the levels of individual transcripts expressed in ALDH$^+$ vs. ALDH$^-$ cells of wild-type mice were analyzed. Using p<0.05 adjusted for multiple comparisons as threshold, 671 differentially expressed transcripts were found. A complete list is shown in Table 7 and a curated sub-list in Table 8. The transcripts fell into three broad categories:

terminal differentiation of β cells, mitochondrial oxidative phosphorylation, and ribosomal subunits. ALDH+ cells were depleted of transcripts encoding insulin, IAPP, Cpe, transthyretin, as well as other pancreatic hormones commonly found at low levels in β cells, and were enriched in transcripts encoding markers of uncommitted endocrine progenitors, such as Pax6, Rfx6, Rfx7, and Mlxipl, as well as transcription factors associated with progenitor cell differentiation, such as Ncor, Hic1, and Bach2. Next, there was a striking decrease of selected mitochondrial components: ~30% of complex I NADH dehydrogenase subunits (13 of 41), complex IV cytochrome C oxidase subunits (8 of 25), and complex V F1 ATP synthase subunits (15 of 54) were substantially decreased. In addition, ~30% of genes (28 of 92) encoding ribosomal 40S and 60S subunits were coordinately decreased (Tables 7 and 8). Interestingly, 6 of the top 12 differentially expressed transcripts were long noncoding RNAs that have been associated with β cell dysfunction: Malat1, Neat1, Meg3, Peg3, Sngh11, and Kcnq1ot1. These highly abundant transcripts increased from 2.5- to 12-fold in ALDH$^+$ cells (Table 8). We used the "upstream regulator analysis" function of the Ingenuity Analysis program to identify contributors to the phenotype of ALDH$^+$ cells based on coordinated changes affecting their downstream effectors and regardless of whether the regulator's own expression levels changed. Z-scores were used to predict activation or inhibition of individual networks. This analysis confirmed that the main differences between ALDH$^+$ and ALDH$^-$ cells could be subsumed under mitochondrial oxidative phosphorylation and revealed a strong potential activation of the RICTOR branch of mTOR signaling. Importantly, the same top five pathways were altered in ALDH$^+$ cells isolated from wild-type and triple-Foxo knockout mice, confirming that most differences between wild-type and Foxo-deficient ALDH$^+$ cells are of a quantitative, rather than qualitative nature (Table 7).

Transcription factor network analyses indicated that ALDH$^+$ cells have stem/progenitor cell properties, based on the combination of activated GATA, Wnt, Nanog, and Neurog3 34 and decreased Foxo and Notch signaling (Table 8 and Table 9). Of note was also the marked inhibition of two master regulators of mitochondrial biogenesis and function, NFE2L2 and NRF1. NRF1 activates expression of EIF2A1 as well as genes required for mitochondrial biogenesis, function, and mitochondrial DNA transcription. The inhibition of NRF1 is consistent with the decrease of Tfam and Eif2 signaling in ALD$^+$ cells (Table 9). NFE2L2 is involved in NRF2-mediated oxidative stress and unfolded protein response. This analysis also indicated activation of RICTOR (mTORC2) signaling. RICTOR promotes β-cell growth and insulin secretion. However, other features of ALD$^+$ cells suggest that the activation of RICTOR is compensatory in nature. For example, ATF4-mediated signaling is inhibited, thus leading to decreased unfolded protein response and apoptotic signaling in response to endoplasmic reticulum stress. There are impairments in insulin and IGF1 receptor signaling, as well as inhibition of the transcriptional network overseen by nuclear receptor NR4A3, which is required for β-cell growth (Table 9). The decrease in insulin/IGF receptor signaling is consistent with the homeostatic role of Foxo in these pathways, such that low Foxo would be expected to result in impaired insulin/IGF receptor signaling. In addition, the mild activation of Src and EGF receptor signaling observed in ALDH$^+$ cells suggests that cells are shifting from a fully differentiated phenotype maintained through insulin receptor/Foxo signaling, to a less differentiated phenotype dependent on oncogene signaling with features of progenitor cells (Table 9). Two other features of ALDH$^+$ cells deserve mention: the decrease in estrogen receptor signaling, and activation of inflammation pathways, including NFKB1, MYD88, TICAM1, IFRD1, TLR7, CXCL12, and IL6 (Table 9).

Example 14

Comparing Wild-Type and Foxo Knockout ALDH Cells.

Next, we compared ALDH$^+$ cells from wild-type and triple Foxo-deficient mice. The rationale was threefold: first, although ALDH1A3 expression is a marker of reduced Foxo activity, Foxo is not absent in the majority of these cells, and complete Foxo ablation may exacerbate their phenotype; second, it may reduce heterogeneity of ALDH$^+$ cells; and third, because Foxo-deficient mice develop a MODY-like form of diabetes, this comparison might reveal qualitative differences between ALDH$^+$ cells isolated from euglycemic vs. diabetic animals. One can hypothesize that complete genetic ablation of Foxo mimics the final stages in the progression of the fate of ALDH$^+$ cells and that, by analyzing differences between wild-type and Foxo-deficient ALDH$^+$ cells, it's possible to identify genes that mark the mechanistic progression to an advanced phase of cellular failure, or a tipping point toward dedifferentiation (FIG. 15B). When we compared transcriptomes of wild-type vs. triple Foxo knockout ALDH$^+$ cells, we found few differentially expressed genes, as predicted (a partial list is in Table 4 and a complete list in Table 6). The dearth of differences between wild-type and Foxo-deficient ALDH$^+$ cells is wholly consistent with the concept that in diabetes there is a "spontaneous" loss of Foxo (Kitamura et al. 2005, Talchai et al. 2012, Kim-muller et al. 2014), and that Foxo normally restrains ALDH1A3 expression (FIG. 12A). Nonetheless, these genes indicated potential pathogenic processes unfolding in failing β cells. A striking aspect of the gene expression profile of Foxo-deficient ALDH+ cells is the decrease in Cyb5r3. This gene encodes cytochrome b5 reductase isoform, one of four b5 reductase subunits (r1 through 4). Its expression is regulated by Foxo and Nrf, consistent with our findings 40. Cyb5r3 has a membrane-bound and a soluble form, the latter of which is restricted to erythrocytes. It utilizes NADH and NADPH to synthesize long-chain FAs, and it's also required for mitochondrial complex III function. Cyb5r3-deficient cells show decreased NAD+/NADH ratios, mitochondrial respiration rate, ATP production, and mitochondrial electron transport. Notably, knockout of the related isoform Cyb5r4 causes early-onset β-cell failure in mice independent of peripheral insulin sensitivity.

Other interesting genes that are specifically altered in Foxo-deficient ALDH$^+$ cells include: Elovl6, Ndor, and Cyp27b1. Elovl6 is a long chain fatty acid elongase that plays an important role in liver. In β cells, its expression pattern mirrors Cyb5r3, and can potentially act in concert with the latter to synthesize long-chain FA. Similarly, the NAPDH-dependent oxidoreductase Ndor, whose expression levels track closely those of Foxo in ALDH$^+$ cells, could be involved in mitochondrial processes related to Cyb5r3. Cyp27b1 is required for the synthesis of 1,25-OH vitamin D3, and evidence suggests that it participates in β-cell dysfunction in diabetes. Finally, there were two transcripts that showed opposite changes in wild-type vs. Foxo-deficient ALDH$^+$ cells: the lncRNA Peg3, a parentally imprinted transcript whose methylation correlates with human islet function, and Bach2, a transcription factor that has been implicated in type 1 diabetes susceptibility as well as β-cell stress (Table 9, Table 10 and Table 11).

The invention is illustrated herein by the experiments described above and by the following examples, which should not be construed as limiting. The contents of all references, pending patent applications and published patents, cited throughout this application are hereby expressly incorporated by reference. Those skilled in the art will understand that this invention may beembodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

TABLE 3

Comparison of the top 10 transcripts in two models of Foxo knockout ββββ cells

| β cell-specific triple FoxO knockout (Rip-cre) | | | | Pan-pancreatic triple FoxO knockout (Pdx-cre) | | | |
|---|---|---|---|---|---|---|---|
| Gene symbol | RefSeq | P | Fold change | Gene symbol | RefSeq | P | Fold change |
| Serpina7 | NM_177920 | 0.0057 | 6.10 | Serpina7 | NM_177920 | 0.005 | 11.23 |
| Rsl1 | NM_001013769 | 0.0645 | 4.99 | Penk | NM_001013769 | $1.45 \times 10^{-5}$ | 9.24 |
| Tcea1 | NM_011541 | 0.0804 | 4.72 | Aldh1a3 | NM_053080 | $5.18 \times 10^{-7}$ | 5.59 |
| Ly96 | NM_016923 | 0.0210 | 3.54 | Aass | NM_013930 | 0.0008 | 5.29 |
| Asb11 | NM_026853 | 0.0011 | 2.93 | Rsl1 | NM_001013769 | 0.0645 | 4.63 |
| Tc2n | NM_001082976 | 0.0428 | 2.91 | Fabp3 | NM_010174 | 0.0070 | 3.49 |
| Aldh1a3 | NM_053080 | $5.18 \times 10^{-7}$ | 2.87 | Zfp423 | NM_033327 | $5.70 \times 10^{-6}$ | 3.40 |
| Fabp3 | NM_010174 | 0.0070 | 2.70 | Ly96 | NM_016923 | 0.0210 | 3.39 |
| Bet1 | NM_009748 | 0.0558 | 2.69 | Asb11 | NM_026853 | 0.0011 | 3.36 |
| Naa38 | NM_133939 | 0.04334 | 2.68 | Tmed6 | NM_025458 | 0.0097 | 3.29 |

List of the 10 top overexpressed genes from RNA sequencing analysis of β cells isolated from β cell-specific and pan-pancreatic Foxo triple Foxo knockouts compared to their relevant wild-type controls.

TABLE 4

Pathway analysis of RNA sequencing in wild-type and Foxo knockout ββββ cells

| | P |
|---|---|
| Wild-type ALDH⁻ vs. ALDH⁺ | |
| Oxidative Phosphorylation | $8.58E^{-21}$ |
| Mitochondrial Dysfunction | $1.02E^{-23}$ |
| EIF2 Signaling | $1.31E^{-15}$ |
| mTOR signaling | $1.81E^{-10}$ |
| Regulation of eIF4 and p70S6K Signaling | $7.17E^{-10}$ |
| Foxo knockout ALDH⁻ vs. ALDH⁺ | |
| EIF2 Signaling | $6.88E^{-08}$ |
| Oxidative Phosphorylation | $1.29E^{-07}$ |
| Mitochondrial Dysfunction | $2.14E^{-06}$ |
| Regulation of eIF4 and p70S6K Signaling | $1.05E^{-04}$ |
| mTOR signaling | $3.78E^{-04}$ |

The table summarizes top pathways from transcriptome analysis of ALDH⁻ vs. ALDH⁺ cells.

TABLE 5

Progenitor-like features of ALDH⁺ cells

| Transcription factor | Z-score | P |
|---|---|---|
| GATA4 | 2.607 | $1.00 \times 10^{-1}$ |
| GATA6 | 2.111 | $1.00 \times 10^{-1}$ |
| NKX6.1 | 1.969 | $2.68 \times 10^{-2}$ |
| PDX1 | 1.575 | $2.11 \times 10^{-6}$ |
| NANOG | 1.508 | $1.62 \times 10^{-2}$ |
| GLIS3 | 1.384 | $8.57 \times 10^{-4}$ |

TABLE 5-continued

Progenitor-like features of ALDH⁺ cells

| Transcription factor | Z-score | P |
|---|---|---|
| CTNNB1 | 1.366 | $2.66 \times 10^{-2}$ |
| HNF1A | 1.028 | $1.39 \times 10^{-2}$ |
| NEUROD1 | 0.741 | $4.70 \times 10^{-4}$ |
| NEUROG3 | 0.791 | $1.38 \times 10^{-4}$ |
| RBPJ | -2.130 | $1.00 \times 10^{-1}$ |
| FOXO1 | -1.811 | $4.91 \times 10^{-3}$ |
| FOXO3 | -1.400 | $2.92 \times 10^{-3}$ |
| FOXO4 | -0.640 | $1.87 \times 10^{-2}$ |
| HNF4A | -1.212 | $1.39 \times 10^{-2}$ |
| NKX2.2 | -1.000 | $2.65 \times 10^{-4}$ |

Z-score analysis of transcriptional networks involved in pancreas development in ALDH⁺ cells.

TABLE 6

Top 25 differentially expressed transcripts in ALDH+ cells from wild-type and Foxo knockout mice

| Gene | Wild-type | Foxo knockout | Fold Change | log$_2$ Fold Change | P | Adjusted P |
|---|---|---|---|---|---|---|
| Foxo1 | 1005.01 | 131.37 | 0.13 | -2.94 | 2.23E-11 | 3.47E-07 |
| Cyb5r3 | 5076.01 | 1742.73 | 0.34 | -1.54 | 8.29E-09 | 6.46E-05 |
| Cyp27b1 | 206.80 | 4.83 | 0.02 | -5.42 | 5.10E-07 | 0.002649712 |
| Elovl7 | 384.62 | 38.27 | 0.10 | -3.33 | 1.46E-06 | 0.005684329 |
| Hip1r | 1463.56 | 467.44 | 0.32 | -1.65 | 2.98E-06 | 0.009288892 |
| Bach2 | 211.79 | 11.73 | 0.06 | -4.17 | 2.45E-05 | 0.052959279 |
| Ctsl | 2272.77 | 5237.71 | 2.30 | 1.20 | 3.39E-05 | 0.052959279 |
| Etl4 | 1573.45 | 590.80 | 0.38 | -1.41 | 3.21E-05 | 0.052959279 |
| Muc4 | 3932.14 | 763.76 | 0.19 | -2.36 | 3.32E-05 | 0.052959279 |
| Ptprt | 753.26 | 181.42 | 0.24 | -2.05 | 2.71E-05 | 0.052959279 |
| Dnahc17 | 112.89 | 1.32 | 0.01 | -6.41 | 3.87E-05 | 0.054903167 |
| Spp1 | 3933.14 | 1896.47 | 0.48 | -1.05 | 0.000104638 | 0.136037989 |
| Gpc6 | 72.93 | 0.00 | 0.00 | N/A | 0.000119737 | 0.14369393 |
| Cxcl13 | 71.93 | 0.00 | 0.00 | N/A | 0.000135081 | 0.150528447 |
| Prnd | 93.91 | 1.06 | 0.01 | -6.47 | 0.000149671 | 0.155667934 |
| 2010015L04Rik | 249.75 | 32.76 | 0.13 | -2.93 | 0.000188906 | 0.173360099 |
| Ncam1 | 2471.57 | 1148.98 | 0.46 | -1.11 | 0.000183578 | 0.173360099 |
| Jam2 | 437.57 | 97.38 | 0.22 | -2.17 | 0.000207049 | 0.179454216 |
| Galntl4 | 316.69 | 53.81 | 0.17 | -2.56 | 0.000328609 | 0.269822705 |
| D0H4S114 | 613.40 | 190.91 | 0.31 | -1.68 | 0.000492415 | 0.351638321 |
| Hcn1 | 76.92 | 0.60 | 0.01 | -7.01 | 0.000495868 | 0.351638321 |
| Nog | 61.94 | 0.00 | 0.00 | N/A | 0.000451442 | 0.351638321 |
| Cox6b1 | 229.77 | 695.81 | 3.03 | 1.60 | 0.000553818 | 0.362501015 |
| Krba1 | 424.58 | 108.79 | 0.26 | -1.96 | 0.000565259 | 0.362501015 |

This table lists a subset of genes differentially expressed between wild-type and triple Foxo-deficient ALDH+ cells, arranged by p-value.

TABLE 7

Complete list of differentially expressed transcripts in wild-type ALDH− vs. ALDH+ cells

| Gene | baseMean all | baseMean ALDH− | baseMean ALDH+ | Fold-Change | log2 Fold-Change | p-value | Adjusted p-value |
|---|---|---|---|---|---|---|---|
| Malat1 | 124697.0147 | 28383.6624 | 317323.7194 | 11.17980178 | 3.482822704 | 3.39E-60 | 5.14E-56 |
| Meg3 | 5885.114667 | 1394.275924 | 14866.79215 | 10.66273318 | 3.414505386 | 3.32E-52 | 2.52E-48 |
| Eml5 | 3444.730595 | 1336.696052 | 7660.799682 | 5.731145589 | 2.518823546 | 9.41E-46 | 4.76E-42 |
| Snhg11 | 894.283641 | 142.4906105 | 2397.869702 | 16.82826464 | 4.072814506 | 4.52E-43 | 1.71E-39 |
| Pyy | 3861.622973 | 5362.393977 | 860.0809636 | 0.16039123 | -2.640332839 | 3.61E-37 | 1.10E-33 |
| Mlxipl | 3287.320318 | 1521.052155 | 6819.856646 | 4.483644184 | 2.164671792 | 1.35E-33 | 3.42E-30 |
| Neat1 | 3757.126356 | 1293.0687 | 8685.241668 | 6.716767383 | 2.747767066 | 1.34E-30 | 2.91E-27 |
| Kcnq1ot1 | 2433.872718 | 775.6169559 | 5750.384243 | 7.413948598 | 2.890242113 | 1.90E-30 | 3.61E-27 |
| Aldh1a3 | 368.1170314 | 43.89471581 | 1016.561662 | 23.15908974 | 4.533506645 | 6.71E-24 | 1.13E-20 |
| Leng8 | 1779.943272 | 852.3747044 | 3635.080408 | 4.264650733 | 2.092427592 | 6.78E-22 | 9.35E-19 |
| Peg3 | 16042.40826 | 10847.18501 | 26432.85474 | 2.436840039 | 1.285011551 | 6.41E-22 | 9.35E-19 |
| Ppy | 1932.691505 | 2650.807083 | 496.4603468 | 0.187286487 | -2.416681283 | 1.23E-21 | 1.55E-18 |
| Rtl1 | 345.7922558 | 47.55764639 | 942.2614745 | 19.81303841 | 4.308378235 | 4.43E-21 | 5.17E-18 |
| Pclo | 14100.27809 | 9753.78149 | 22793.2713 | 2.336865073 | 1.224574438 | 1.66E-19 | 1.80E-16 |
| Srek1 | 1259.611237 | 591.4150864 | 2596.003537 | 4.389478044 | 2.134049398 | 6.07E-18 | 6.14E-15 |
| Muc4 | 2414.456104 | 1406.187643 | 4430.993027 | 3.151068102 | 1.655840935 | 3.13E-17 | 2.97E-14 |
| Ddx17 | 4121.159918 | 2713.272011 | 6936.93573 | 2.556668001 | 1.35426483 | 1.22E-15 | 1.09E-12 |
| Kcnh6 | 747.3977997 | 300.980231 | 1640.232937 | 5.44963678 | 2.446160077 | 1.50E-15 | 1.27E-12 |
| Ttc14 | 1143.975357 | 574.4419657 | 2283.042139 | 3.974365167 | 1.990724434 | 8.00E-15 | 6.39E-12 |
| Mll3 | 4965.016558 | 3398.727474 | 8097.594726 | 2.382537225 | 1.252498755 | 9.11E-15 | 6.91E-12 |
| Rps5 | 3173.536935 | 4075.843065 | 1368.924675 | 0.33586295 | -1.574055439 | 1.36E-14 | 9.85E-12 |
| Atp5e | 1168.175777 | 1589.028404 | 326.4705228 | 0.205452918 | -2.283120272 | 4.43E-14 | 3.05E-11 |
| 6720401G13Rik | 491.3093791 | 172.3952163 | 1129.137705 | 6.549704391 | 2.711429795 | 1.89E-13 | 1.25E-10 |
| Zfc3h1 | 1298.696003 | 594.3170947 | 2707.453819 | 4.555571163 | 2.187631946 | 2.63E-13 | 1.66E-10 |
| A330076H08Rik | 1758.528488 | 1051.033415 | 3173.518634 | 3.019426963 | 1.594274776 | 2.86E-13 | 1.73E-10 |
| Rplp1 | 1578.464831 | 2091.323062 | 552.748368 | 0.264305586 | -1.919721178 | 2.97E-13 | 1.73E-10 |
| Cd63 | 2345.010105 | 3053.138983 | 928.7523494 | 0.304195896 | -1.716927404 | 3.20E-13 | 1.80E-10 |
| Clk1 | 1469.244663 | 846.7628045 | 2714.208381 | 3.205393962 | 1.680501684 | 6.57E-13 | 3.54E-10 |
| Nktr | 3576.811233 | 2171.434528 | 6387.564643 | 2.941633543 | 1.556617533 | 6.76E-13 | 3.54E-10 |
| Pnn | 1411.689954 | 816.7187615 | 2601.632339 | 3.185469052 | 1.671505821 | 1.48E-12 | 7.46E-10 |
| Rpl32 | 2881.163807 | 3663.738743 | 1316.013935 | 0.359199721 | -1.477141865 | 1.61E-12 | 7.87E-10 |
| Atf4 | 7482.139646 | 9156.313331 | 4133.792275 | 0.451469071 | -1.147300938 | 2.07E-12 | 9.80E-10 |
| Rian | 3597.354337 | 2481.437769 | 5829.187473 | 2.349116929 | 1.232118527 | 2.17E-12 | 1.00E-09 |
| 2810403A07Rik | 1222.687467 | 688.0070889 | 2292.048222 | 3.331431114 | 1.736142062 | 3.57E-12 | 1.59E-09 |
| Nfat5 | 2909.357259 | 1977.986671 | 4772.098435 | 2.412603939 | 1.270591098 | 9.11E-12 | 3.95E-09 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Krtcap2 | 1391.465937 | 1836.717211 | 500.9633885 | 0.27274933 | −1.874352443 | 1.01E−11 | 4.24E−09 |
| Rgs9 | 823.2847727 | 416.4993312 | 1636.855656 | 3.930031895 | 1.974541021 | 1.97E−11 | 8.07E−09 |
| Rps4x | 1727.318491 | 2240.303365 | 701.3487439 | 0.31305972 | −1.6754902 | 2.39E−11 | 9.56E−09 |
| Rpl8 | 2402.659371 | 3049.552048 | 1108.874017 | 0.363618656 | −1.459501874 | 4.04E−11 | 1.57E−08 |
| Golgb1 | 8345.742428 | 6335.374515 | 12366.47825 | 1.951972724 | 0.964932894 | 4.45E−11 | 1.69E−08 |
| Cst3 | 2615.619732 | 3293.566641 | 1259.725914 | 0.382480773 | −1.386540869 | 1.02E−10 | 3.69E−08 |
| Mt1 | 2089.802405 | 2664.698631 | 940.0099536 | 0.352764077 | −1.50322444 | 9.99E−11 | 3.69E−08 |
| Tbrg3 | 215.4640465 | 46.25900559 | 553.8741284 | 11.97332544 | 3.581751993 | 1.13E−10 | 3.99E−08 |
| Cacna1a | 843.2644231 | 448.7203277 | 1632.352614 | 3.637795111 | 1.863064289 | 1.36E−10 | 4.70E−08 |
| Fnbp4 | 863.6837877 | 466.9660098 | 1657.119343 | 3.548693714 | 1.827288061 | 1.83E−10 | 6.18E−08 |
| Rps3 | 2813.934375 | 3520.678579 | 1400.445967 | 0.397777285 | −1.329967201 | 2.01E−10 | 6.61E−08 |
| Kif12 | 1212.653456 | 725.8668125 | 2186.226742 | 3.011884143 | 1.590666275 | 2.12E−10 | 6.85E−08 |
| Prrc2c | 8966.535509 | 6914.764004 | 13070.07852 | 1.890169861 | 0.918515889 | 2.31E−10 | 7.15E−08 |
| Ttr | 4923.070751 | 6008.364008 | 2752.484236 | 0.458108768 | −1.126237918 | 2.31E−10 | 7.15E−08 |
| Egr1 | 7123.470171 | 5439.724564 | 10490.96139 | 1.928583196 | 0.947541383 | 3.31E−10 | 1.00E−07 |
| Sfrs18 | 1114.682974 | 660.5287199 | 2022.991481 | 3.062685119 | 1.614797048 | 4.38E−10 | 1.30E−07 |
| 9530091C08Rik | 193.7560951 | 40.71532863 | 499.837628 | 12.2763992 | 3.61781556 | 6.24E−10 | 1.82E−07 |
| Dtx3 | 389.911961 | 151.4501784 | 866.8355261 | 5.723568868 | 2.516915004 | 7.06E−10 | 1.98E−07 |
| Zbed6 | 2100.148856 | 1427.809836 | 3444.826896 | 2.412665054 | 1.270627643 | 6.94E−10 | 1.98E−07 |
| Gm16907 | 275.9072982 | 84.01314317 | 659.6956082 | 7.852290526 | 2.973113552 | 7.40E−10 | 2.04E−07 |
| Lamp1 | 7939.319946 | 9490.84653 | 4836.266779 | 0.509571698 | −0.972642944 | 1.14E−09 | 3.09E−07 |
| Itga4 | 720.4112402 | 379.2681164 | 1402.697488 | 3.698432394 | 1.886913904 | 1.17E−09 | 3.12E−07 |
| Iapp | 499863.3592 | 660135.5386 | 179319.0006 | 0.271639671 | −1.880233904 | 1.49E−09 | 3.89E−07 |
| Cox4i1 | 1299.685585 | 1686.100438 | 526.8558782 | 0.312470044 | −1.678210207 | 1.82E−09 | 4.67E−07 |
| Tet2 | 1379.552138 | 883.902481 | 2370.851452 | 2.682254551 | 1.423446158 | 2.92E−09 | 7.38E−07 |
| Srp14 | 980.4443428 | 1323.754779 | 293.8234705 | 0.22196216 | −2.171614345 | 3.61E−09 | 8.99E−07 |
| Mir682 | 1380.799413 | 1777.938529 | 586.5211807 | 0.329888335 | −1.599950332 | 3.67E−09 | 8.99E−07 |
| Uqcrq | 1081.424038 | 1415.559019 | 413.1540754 | 0.291866372 | −1.776620097 | 4.12E−09 | 9.92E−07 |
| Rps15 | 1831.08685 | 2313.775392 | 865.7097657 | 0.374154626 | −1.418293484 | 4.51E−09 | 1.07E−06 |
| Fosb | 396.9418115 | 165.9351156 | 858.9552032 | 5.176452253 | 2.371963667 | 4.61E−09 | 1.08E−06 |
| Cyp27b1 | 80.17526727 | 3.746697067 | 233.0324077 | 62.19675718 | 5.958767458 | 5.50E−09 | 1.27E−06 |
| Zfp612 | 1138.63936 | 698.1519397 | 2019.6142 | 2.892800385 | 1.532466775 | 5.61E−09 | 1.27E−06 |
| Rpl41 | 7227.255257 | 9232.17124 | 3217.42329 | 0.348501258 | −1.520764231 | 6.15E−09 | 1.37E−06 |
| Ddx26b | 655.9202741 | 348.3886521 | 1270.983518 | 3.648177145 | 1.867175784 | 7.18E−09 | 1.58E−06 |
| Hip1r | 906.0685398 | 534.4832995 | 1649.23902 | 3.085669883 | 1.625583725 | 7.73E−09 | 1.68E−06 |
| 4930480K15Rik | 65.07774389 | 1.364099629 | 192.5050324 | 141.1224139 | 7.140803333 | 9.01E−09 | 1.93E−06 |
| Rps24 | 1568.410415 | 1994.060928 | 717.4921578 | 0.359622607 | −1.475444378 | 9.24E−09 | 1.95E−06 |
| Nme2 | 992.0190731 | 1300.026619 | 376.0039815 | 0.28922791 | −1.78972132 | 1.07E−08 | 2.22E−06 |
| D330022K07Rik | 205.841139 | 55.46561314 | 506.5921906 | 9.133446147 | 3.191159307 | 1.17E−08 | 2.40E−06 |
| Rbm26 | 1665.026644 | 1130.303931 | 2734.472069 | 2.419236095 | 1.27455157 | 1.19E−08 | 2.40E−06 |
| Ndufa11 | 721.1160176 | 966.8464632 | 229.6551264 | 0.237530089 | −2.073817818 | 1.31E−08 | 2.62E−06 |
| Rps9 | 1562.017646 | 1981.657374 | 722.7381919 | 0.364714002 | −1.455162505 | 1.44E−08 | 2.84E−06 |
| Setd2 | 1870.046503 | 1298.239427 | 3013.660654 | 2.321344269 | 1.214960499 | 1.46E−08 | 2.84E−06 |
| 9430032N09Rik | 244.0057524 | 77.25107994 | 577.5150973 | 7.475819079 | 2.902231655 | 1.50E−08 | 2.88E−06 |
| Mat2a | 1534.736793 | 1031.121671 | 2541.967036 | 2.465244508 | 1.301730743 | 1.53E−08 | 2.90E−06 |
| 6820431F20Rik | 759.6451309 | 435.3045514 | 1408.32629 | 3.235266632 | 1.693884616 | 2.12E−08 | 3.97E−06 |
| Zc3h7a | 1224.332633 | 793.4819166 | 2086.034065 | 2.628962326 | 1.394493468 | 2.31E−08 | 4.28E−06 |
| Park7 | 933.5962577 | 1222.52424 | 355.7402938 | 0.290988336 | −1.780966771 | 2.83E−08 | 5.18E−06 |
| Calr | 5932.802875 | 7057.468779 | 3683.488106 | 0.521928282 | −0.938076516 | 3.03E−08 | 5.22E−06 |
| Zfp182 | 282.0122967 | 102.7396046 | 640.557681 | 6.234768798 | 2.640336062 | 3.03E−08 | 5.41E−06 |
| Eid3 | 69.00371785 | 2.750018869 | 201.5111158 | 73.27626661 | 6.195274096 | 3.57E−08 | 6.23E−06 |
| Gpr98 | 423.9359111 | 196.2944212 | 879.2188908 | 4.479082418 | 2.163203213 | 3.54E−08 | 6.23E−06 |
| Ankrd12 | 1720.417204 | 1194.251845 | 2772.747923 | 2.321744259 | 1.215209358 | 3.61E−08 | 6.23E−06 |
| Mbd5 | 1072.882873 | 680.0090795 | 1858.630459 | 2.733243592 | 1.450614041 | 4.12E−08 | 6.95E−06 |
| Rpl14 | 1123.021808 | 1448.685903 | 471.6936175 | 0.325601027 | −1.618822846 | 4.09E−08 | 6.95E−06 |
| Mt2 | 3313.467797 | 4244.649102 | 1451.105186 | 0.341866937 | −1.548493194 | 4.70E−08 | 7.84E−06 |
| Psmb4 | 1784.130152 | 2229.83122 | 892.7280159 | 0.400356766 | −1.320641907 | 5.25E−08 | 8.66E−06 |
| Nav2 | 3628.636742 | 2764.208186 | 5357.493856 | 1.938165831 | 0.954692014 | 5.54E−08 | 8.94E−06 |
| Pcsk4 | 206.2760136 | 61.18384699 | 496.4603468 | 8.114238826 | 3.020455766 | 5.52E−08 | 8.94E−06 |
| Gm15421 | 1107.682334 | 1426.239572 | 470.567857 | 0.329936054 | −1.599741655 | 6.31E−08 | 9.88E−06 |
| Ogt | 1260.427535 | 834.6780245 | 2111.926555 | 2.530229013 | 1.339267971 | 6.32E−08 | 9.88E−06 |
| Rbm5 | 1920.132119 | 1362.673128 | 3035.050102 | 2.227276696 | 1.155280796 | 6.30E−08 | 9.88E−06 |
| Bod1l | 1671.043882 | 1163.533637 | 2686.064371 | 2.308540367 | 1.20698096 | 6.91E−08 | 1.07E−05 |
| Ccdc56 | 634.6392382 | 850.6404192 | 202.6368762 | 0.238216844 | −2.069652666 | 8.11E−08 | 1.24E−05 |
| Snap25 | 6990.999772 | 5583.813014 | 9805.373289 | 1.756035395 | 0.812321924 | 8.69E−08 | 1.32E−05 |
| Gabarap | 2509.461602 | 3069.598222 | 1389.188363 | 0.452563581 | −1.143807604 | 9.35E−08 | 1.40E−05 |
| Pam | 9800.780588 | 11442.09446 | 6518.152852 | 0.569664311 | −0.81181607 | 1.19E−07 | 1.77E−05 |
| Ppig | 1518.226593 | 1051.386789 | 2451.906202 | 2.332068681 | 1.221610278 | 1.29E−07 | 1.90E−05 |
| Cd44 | 1020.106568 | 655.4440025 | 1749.431698 | 2.66907881 | 1.416341905 | 1.43E−07 | 2.09E−05 |
| Cox7a2 | 894.9022553 | 1190.375726 | 303.9553144 | 0.255344013 | −1.969485864 | 1.45E−07 | 2.10E−05 |
| Syp | 4221.895934 | 3293.290757 | 6079.106287 | 1.84590634 | 0.884329353 | 1.79E−07 | 2.57E−05 |
| Atxn7 | 851.8757747 | 528.6201002 | 1498.387124 | 2.834525443 | 1.503107219 | 2.17E−07 | 3.08E−05 |
| Ccnl2 | 708.9787581 | 420.0960551 | 1286.744164 | 3.062976071 | 1.614934096 | 2.23E−07 | 3.13E−05 |
| Psma6 | 1432.573254 | 1798.748389 | 700.2229834 | 0.389283453 | −1.361107074 | 2.55E−07 | 3.54E−05 |
| Dnahc17 | 42.40364262 | 0 | 127.2109279 | Inf | Inf | 2.76E−07 | 3.78E−05 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Mdh1 | 2929.812363 | 3538.014862 | 1713.407365 | 0.484284954 | −1.046071914 | 2.75E-07 | 3.78E-05 |
| Fis1 | 377.4084833 | 522.7709486 | 86.68355261 | 0.16581555 | −2.592348783 | 3.29E-07 | 4.45E-05 |
| Prdx1 | 1903.520509 | 2344.748411 | 1021.064704 | 0.435468769 | −1.199358884 | 3.72E-07 | 4.97E-05 |
| Prpf39 | 518.560888 | 281.3809852 | 992.9206936 | 3.528741265 | 1.819153653 | 3.73E-07 | 4.97E-05 |
| Col6a6 | 944.1553283 | 609.6256489 | 1613.214687 | 2.646238212 | 1.403942937 | 4.71E-07 | 6.22E-05 |
| Gm17066 | 289.1343202 | 121.8658429 | 623.6712746 | 5.117687284 | 2.355491994 | 4.81E-07 | 6.29E-05 |
| Swi5 | 890.0231708 | 1148.721406 | 372.6267002 | 0.324383874 | −1.624225992 | 5.44E-07 | 7.05E-05 |
| Cox17 | 561.6042762 | 750.0940595 | 184.6247095 | 0.246135411 | −2.022475866 | 6.45E-07 | 8.30E-05 |
| Clk4 | 823.3771513 | 521.3336184 | 1427.464217 | 2.738101221 | 1.45317578 | 7.31E-07 | 9.32E-05 |
| Fth1 | 4264.9379 | 5041.991301 | 2710.8311 | 0.537650888 | −0.895258401 | 8.28E-07 | 0.000104333 |
| Rps27l | 715.8016824 | 936.3597519 | 274.6855433 | 0.29335471 | −1.76928194 | 8.32E-07 | 0.000104333 |
| Rpl13a | 1291.434964 | 1619.125126 | 636.0546393 | 0.392838471 | −1.347991873 | 9.02E-07 | 0.000111832 |
| Tmem181b-ps | 285.4795395 | 122.5753542 | 611.28791 | 4.987037679 | 2.318183103 | 9.03E-07 | 0.000111832 |
| Shfm1 | 284.5550301 | 400.3771753 | 52.91073991 | 0.132152238 | −2.919727234 | 9.48E-07 | 0.000115947 |
| Gm7694 | 38.65110787 | 0 | 115.9533236 | Inf | Inf | 1.05E-06 | 0.000127759 |
| Setd5 | 4366.232198 | 3479.681174 | 6138.771589 | 1.764033832 | 0.81887823 | 1.07E-06 | 0.000128501 |
| Dst | 10942.1612 | 9094.673288 | 14637.13703 | 1.609418674 | 0.686539678 | 1.21E-06 | 0.000144648 |
| Slc7a15 | 97.32465051 | 15.96164685 | 260.0506578 | 16.29221973 | 4.026111272 | 1.32E-06 | 0.000156516 |
| Srrm2 | 15682.22232 | 11549.18273 | 23948.30149 | 2.073592742 | 1.052132574 | 1.36E-06 | 0.000159857 |
| Ncoa6 | 3024.722863 | 2351.420432 | 4371.327725 | 1.859015795 | 0.894539028 | 1.40E-06 | 0.000162812 |
| Ncor1 | 4756.034573 | 3821.501813 | 6625.100092 | 1.733637825 | 0.793802536 | 1.41E-06 | 0.000162812 |
| Rev3l | 2126.893097 | 1598.514407 | 3183.650478 | 1.991630769 | 0.993950209 | 1.43E-06 | 0.00016437 |
| Rfx6 | 1900.222731 | 1409.360754 | 2881.946684 | 2.044860889 | 1.032002701 | 1.46E-06 | 0.000166394 |
| A930012L18Rik | 42.3315224 | 0.454996876 | 126.0851674 | 277.2931464 | 8.115268241 | 1.50E-06 | 0.000168352 |
| Dhx57 | 473.5894326 | 260.6428597 | 899.4825784 | 3.451015614 | 1.787021001 | 1.51E-06 | 0.000168352 |
| Gria3 | 306.6181575 | 134.0195937 | 651.8152852 | 4.863582014 | 2.282019246 | 1.49E-06 | 0.000168352 |
| Bnip2 | 299.5960726 | 135.3069507 | 628.1743163 | 4.642587191 | 2.214929005 | 1.59E-06 | 0.000176512 |
| Gcfc1 | 818.5148381 | 526.8963934 | 1401.571727 | 2.659597562 | 1.41120796 | 1.61E-06 | 0.000176894 |
| Insrr | 2924.26832 | 2273.913045 | 4224.978869 | 1.858021299 | 0.89376704 | 1.65E-06 | 0.000180243 |
| Phc3 | 1515.320881 | 1094.310158 | 2357.342327 | 2.154181161 | 1.107139582 | 1.79E-06 | 0.000193945 |
| Pkd1 | 1064.446332 | 726.4566899 | 1740.425615 | 2.395773401 | 1.260491461 | 1.96E-06 | 0.000210658 |
| Ndufb9 | 951.5812564 | 1211.788764 | 431.1662422 | 0.355809738 | −1.4908221 | 1.97E-06 | 0.000210659 |
| Anxa5 | 3243.975579 | 3855.030718 | 2021.865721 | 0.524474607 | −0.93105517 | 2.06E-06 | 0.000218601 |
| D4Wsu53e | 1461.268119 | 837.6123884 | 2708.579579 | 3.233690925 | 1.693181793 | 2.11E-06 | 0.000222815 |
| Qdpr | 917.8697902 | 1170.790528 | 412.028315 | 0.351923171 | −1.506667589 | 2.13E-06 | 0.000222852 |
| Rps20 | 880.677503 | 1126.822581 | 388.3873461 | 0.344674798 | −1.536692278 | 2.17E-06 | 0.000225538 |
| Mysm1 | 1421.579475 | 1019.555034 | 2225.628357 | 2.182940875 | 1.126273056 | 2.22E-06 | 0.000229527 |
| B430010I23Rik | 36.39958703 | 0 | 109.1987611 | Inf | Inf | 2.35E-06 | 0.000240834 |
| 5330434G04Rik | 340.2046871 | 166.9501015 | 686.7138584 | 4.113288056 | 2.040292108 | 2.53E-06 | 0.000257955 |
| Ndor1 | 400.7365395 | 209.903062 | 782.4034944 | 3.727451552 | 1.898189601 | 2.66E-06 | 0.000269397 |
| Tia1 | 655.5193016 | 405.7638531 | 1155.030195 | 2.846557622 | 1.509218304 | 2.81E-06 | 0.000281964 |
| Mycbp2 | 3956.556309 | 3169.403983 | 5530.860961 | 1.745079198 | 0.803292513 | 2.97E-06 | 0.000296631 |
| Ssr2 | 1744.583094 | 2130.546138 | 972.6570059 | 0.456529426 | −1.131220241 | 3.09E-06 | 0.000306238 |
| Gdap10 | 159.7800565 | 49.41657315 | 380.5070232 | 7.699988058 | 2.944856208 | 3.24E-06 | 0.000318732 |
| Gm10538 | 46.34416298 | 1.407743851 | 136.2170112 | 96.7629835 | 6.596383348 | 3.31E-06 | 0.000323552 |
| Ubn2 | 2792.643118 | 2050.019873 | 4277.889609 | 2.08675519 | 1.061261359 | 3.49E-06 | 0.000339281 |
| Gnb2l1 | 2891.811573 | 3663.386865 | 1348.660987 | 0.368145936 | −1.441650318 | 3.65E-06 | 0.000352859 |
| Cspp1 | 725.273222 | 464.2385584 | 1247.342549 | 2.686856847 | 1.425919458 | 4.32E-06 | 0.000415166 |
| Rps11 | 1423.455085 | 1754.675706 | 761.0510463 | 0.433750404 | −1.20520933 | 4.37E-06 | 0.000416959 |
| Eef1a1 | 12058.09772 | 14428.42521 | 7317.442753 | 0.507154637 | −0.979502386 | 4.83E-06 | 0.000457169 |
| Ftl1 | 5236.563516 | 6257.954113 | 3193.782322 | 0.510355663 | −0.970425094 | 4.87E-06 | 0.000457169 |
| Gpr137b-ps | 590.5667842 | 360.1200585 | 1051.460236 | 2.919749153 | 1.545844427 | 4.94E-06 | 0.000457169 |
| Slc2a4rg-ps | 127.0909647 | 33.59286789 | 314.0871582 | 9.349816728 | 3.224938086 | 4.91E-06 | 0.000457169 |
| Zfp187 | 1394.277116 | 1012.937188 | 2156.956971 | 2.129408414 | 1.090452681 | 4.92E-06 | 0.000457169 |
| Ubl5 | 669.8284767 | 868.5257038 | 272.4340225 | 0.313674105 | −1.672661663 | 5.49E-06 | 0.000504996 |
| Bach2 | 90.34029857 | 16.17984297 | 238.6612098 | 14.75052695 | 3.88269459 | 5.61E-06 | 0.000512996 |
| Ndufc2 | 1196.019296 | 1486.696348 | 614.6651912 | 0.413464668 | −1.274237321 | 5.86E-06 | 0.000532564 |
| Tmem59 | 2694.538932 | 3203.679762 | 1676.257271 | 0.523228723 | −0.934486354 | 6.40E-06 | 0.0005778 |
| Uqcrh | 902.7605125 | 1142.497809 | 423.2859192 | 0.370491668 | −1.432486996 | 6.81E-06 | 0.000611076 |
| Gm5148 | 1134.385222 | 1412.820284 | 577.5150973 | 0.408767558 | −1.290647394 | 7.31E-06 | 0.000652729 |
| Kcnmb1 | 213.780519 | 86.51261043 | 468.3163362 | 5.413272515 | 2.436501018 | 7.58E-06 | 0.000672217 |
| Fermt1 | 33.02230576 | 0 | 99.06691727 | Inf | Inf | 7.84E-06 | 0.000691542 |
| Tnrc6a | 1225.919763 | 880.8575235 | 1916.044241 | 2.175203356 | 1.121150282 | 8.23E-06 | 0.000722211 |
| Cttnbp2 | 1449.986654 | 1069.483246 | 2210.993472 | 2.06734746 | 1.047780884 | 8.50E-06 | 0.000736801 |
| Gcc2 | 1836.373666 | 1394.079027 | 2720.962944 | 1.951799641 | 0.964804963 | 8.60E-06 | 0.000736801 |
| Inha | 270.3199716 | 125.1656119 | 560.6286293 | 4.479095197 | 2.163207329 | 8.57E-06 | 0.000736801 |
| Tnfrsf18 | 119.1784898 | 30.73023901 | 296.0749914 | 9.634646555 | 3.268231743 | 8.48E-06 | 0.000736801 |
| Cox7b | 1380.800168 | 1696.322031 | 749.7564421 | 0.44198945 | −1.17791616 | 8.68E-06 | 0.000739806 |
| 4930565N06Rik | 123.6967957 | 33.56753632 | 303.9553144 | 9.055037923 | 3.178720683 | 9.65E-06 | 0.000818223 |
| Rps15a | 849.6370594 | 1076.584635 | 395.7419513 | 0.367032833 | −1.446018969 | 9.22E-06 | 0.000831648 |
| Gm5577 | 80.75459424 | 13.0588907 | 216.1460013 | 16.55163568 | 4.04890189 | 9.93E-06 | 0.00083258 |
| Uqcr10 | 773.9672974 | 987.5838408 | 346.7342104 | 0.351093443 | −1.510073044 | 1.00E-05 | 0.000836426 |
| Nav1 | 2466.261041 | 1933.073458 | 3532.636209 | 1.827471271 | 0.869848726 | 1.02E-05 | 0.000848599 |
| Rbm39 | 2895.10376 | 2299.963351 | 4085.384577 | 1.776282468 | 0.82886102 | 1.04E-05 | 0.00086138 |
| Atp6v1e1 | 1154.079101 | 1431.666379 | 598.9045453 | 0.418326891 | −1.257297354 | 1.06E-05 | 0.000867355 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Wbp7 | 640.6860535 | 407.7178321 | 1106.622496 | 2.714187139 | 1.440520196 | 1.06E−05 | 0.000867355 |
| 4931430N09Rik | 94.00393133 | 18.86089104 | 244.2900119 | 12.95219889 | 3.695125139 | 1.11E−05 | 0.000901606 |
| Smap2 | 2257.314638 | 2694.192176 | 1383.559561 | 0.513534102 | −0.96146801 | 1.23E−05 | 0.000994242 |
| Ddost | 2387.450381 | 2842.113854 | 1478.123436 | 0.520078896 | −0.943197597 | 1.24E−05 | 0.000998838 |
| Ncrna00085 | 163.6534571 | 58.04107512 | 374.878221 | 6.458843505 | 2.691275865 | 1.33E−05 | 0.001061652 |
| Lpcat4 | 236.9220706 | 105.4642919 | 499.837628 | 4.739401547 | 2.244704899 | 1.35E−05 | 0.0010736 |
| Scn8a | 487.3484476 | 291.413226 | 879.2188908 | 3.017086434 | 1.593156028 | 1.44E−05 | 0.001137431 |
| Tnfrsf11a | 324.0356241 | 167.4632362 | 637.1803997 | 3.804897206 | 1.927857478 | 1.46E−05 | 0.001149413 |
| Mga | 3217.622249 | 2590.110292 | 4472.646163 | 1.726816876 | 0.788115097 | 1.53E−05 | 0.001193868 |
| Atp1a1 | 8664.992101 | 9889.826502 | 6215.323298 | 0.628456252 | −0.670115775 | 1.55E−05 | 0.001206084 |
| Ndufs6 | 272.5132017 | 376.6856305 | 64.16834414 | 0.170349859 | −2.553427339 | 1.64E−05 | 0.001253071 |
| Nfasc | 2402.874348 | 1891.467037 | 3425.688969 | 1.81112803 | 0.856888535 | 1.65E−05 | 0.001253071 |
| Nrxn1 | 1556.885771 | 1171.292379 | 2328.072556 | 1.987610095 | 0.991034774 | 1.66E−05 | 0.001253071 |
| Son | 5191.689544 | 4300.491404 | 6974.085824 | 1.621695097 | 0.697502597 | 1.63E−05 | 0.001253071 |
| Ssr4 | 1947.500427 | 2336.4181 | 1169.66508 | 0.500623189 | −0.998202976 | 1.66E−05 | 0.001253071 |
| Timm17a | 544.0317757 | 710.2261838 | 211.7429596 | 0.297993744 | −1.746646051 | 1.62E−05 | 0.001253071 |
| Ghitm | 6403.814598 | 7351.949529 | 4507.544736 | 0.61310877 | −0.705785053 | 1.75E−05 | 0.001316353 |
| Hook3 | 2507.831178 | 1984.733939 | 3554.025657 | 1.790681153 | 0.840508475 | 1.80E−05 | 0.001343701 |
| Sumo3 | 1156.450233 | 1427.905634 | 613.5394308 | 0.429677855 | −1.218672669 | 1.81E−05 | 0.001343701 |
| BC006779 | 266.1946306 | 127.4208036 | 543.7422686 | 4.267295992 | 2.093322184 | 1.82E−05 | 0.001344302 |
| Plekha6 | 2642.469704 | 2102.259695 | 3722.889721 | 1.770899061 | 0.824481983 | 1.85E−05 | 0.001365357 |
| Smarcc2 | 3309.723387 | 2675.914139 | 4577.341882 | 1.710571283 | 0.774478226 | 1.91E−05 | 0.001398138 |
| Mbd6 | 978.5069081 | 690.4227896 | 1554.675145 | 2.251772636 | 1.171061164 | 1.95E−05 | 0.001420211 |
| Atat1 | 255.1542928 | 120.4292605 | 524.6043574 | 4.35612039 | 2.123043826 | 1.96E−05 | 0.001420678 |
| 2010107E04Rik | 481.1938088 | 633.41852 | 176.7443865 | 0.279032553 | −1.841494655 | 1.97E−05 | 0.001422433 |
| Dmxl2 | 2854.792721 | 2285.652971 | 3993.072222 | 1.747015961 | 0.804892789 | 2.02E−05 | 0.00145584 |
| Prdm2 | 2251.292642 | 1766.538677 | 3220.800572 | 1.823226751 | 0.866493997 | 2.06E−05 | 0.001472489 |
| Eif2s3y | 846.3030765 | 559.0997876 | 1420.709654 | 2.541066346 | 1.345434044 | 2.13E−05 | 0.001513936 |
| Slc4a4 | 285.8319481 | 143.3676548 | 570.7605347 | 3.981096961 | 1.993166009 | 2.19E−05 | 0.001554403 |
| A330023F24Rik | 296.7012939 | 151.2284703 | 587.6469411 | 3.885822159 | 1.958219875 | 2.21E−05 | 0.001555815 |
| Myeov2 | 273.2224108 | 376.6236836 | 66.41986499 | 0.176356049 | −2.50343703 | 2.21E−05 | 0.001555815 |
| Golt1b | 2267.577427 | 2753.491017 | 1295.750247 | 0.47058452 | −1.087474233 | 2.23E−05 | 0.001559353 |
| Zfhx2 | 1479.767563 | 1113.028848 | 2213.244993 | 1.988488436 | 0.991672172 | 2.25E−05 | 0.001565715 |
| Dync2h1 | 1311.461567 | 970.894375 | 1992.59595 | 2.052330306 | 1.03726294 | 2.26E−05 | 0.001566599 |
| Ndufa5 | 160.643432 | 230.8333042 | 20.26368762 | 0.087784939 | −3.509882741 | 2.27E−05 | 0.001566944 |
| Ndufa2 | 456.2225583 | 602.1533266 | 164.3610218 | 0.272955433 | −1.873262683 | 2.40E−05 | 0.001645658 |
| Fam76b | 409.2772988 | 235.6604459 | 756.5110046 | 3.210173865 | 1.682653437 | 2.46E−05 | 0.001678334 |
| Tmem206 | 1779.102049 | 2137.294153 | 1062.71784 | 0.497225821 | −1.008026878 | 2.49E−05 | 0.001696681 |
| AF357425 | 42.11516172 | 1.818799505 | 122.7078862 | 67.46641718 | 6.076097644 | 2.51E−05 | 0.001698001 |
| Ostc | 2610.89929 | 3079.34606 | 1674.00575 | 0.543623782 | −0.879319525 | 2.58E−05 | 0.001732547 |
| St18 | 4812.606544 | 3989.666041 | 6458.48755 | 1.618804051 | 0.694928364 | 2.58E−05 | 0.001732547 |
| Abcc10 | 255.5501049 | 123.8373797 | 518.9755552 | 4.190782755 | 2.067219736 | 2.84E−05 | 0.001899492 |
| 2410021H03Rik | 192.0032945 | 79.73926347 | 416.5313567 | 5.223666969 | 2.385062922 | 2.87E−05 | 0.001907047 |
| 1500016L03Rik | 69.7994055 | 10.69811288 | 188.0019907 | 17.57337886 | 4.135319702 | 2.98E−05 | 0.001962504 |
| Cox6a1 | 1512.019127 | 1830.107885 | 875.8416759 | 0.478573759 | −1.063186802 | 2.98E−05 | 0.001962504 |
| Pfdn5 | 1055.656043 | 1305.984121 | 554.9998888 | 0.424966797 | −1.234577968 | 3.00E−05 | 0.001962504 |
| Rhoa | 2341.72954 | 2772.406831 | 1480.374957 | 0.533967432 | −0.905176343 | 3.00E−05 | 0.001962504 |
| Gm3086 | 33.33998542 | 0.476519488 | 99.06691727 | 207.8968853 | 7.699724334 | 3.08E−05 | 0.001996247 |
| Gnai2 | 5066.878258 | 5832.301349 | 3536.01349 | 0.606280033 | −0.721943784 | 3.08E−05 | 0.001996247 |
| Eif3d | 986.0999174 | 1224.72802 | 508.8437114 | 0.415474867 | −1.267166887 | 3.20E−05 | 0.002059309 |
| Lamtor2 | 255.8089329 | 353.317868 | 60.79106287 | 0.172057709 | −2.539035563 | 3.21E−05 | 0.002059309 |
| Rabac1 | 643.9548192 | 824.6492957 | 282.5658663 | 0.342649739 | −1.545193505 | 3.22E−05 | 0.002059309 |
| Maged1 | 21055.50113 | 23654.52103 | 15857.46133 | 0.670377612 | −0.576954125 | 3.32E−05 | 0.002115983 |
| Luc7l2 | 1630.528674 | 1247.983921 | 2395.618181 | 1.919590583 | 0.94079864 | 3.41E−05 | 0.002163588 |
| Eif3i | 1555.789297 | 1876.625214 | 914.1174639 | 0.487107099 | −1.037689086 | 3.73E−05 | 0.002355575 |
| Rps14 | 1070.103394 | 1438.542548 | 333.2250854 | 0.231640757 | −2.110038976 | 3.75E−05 | 0.002361914 |
| Asns | 4361.644749 | 5033.948156 | 3017.037935 | 0.599338301 | −0.738557522 | 3.81E−05 | 0.002389791 |
| Zfp445 | 1120.147309 | 821.2657603 | 1717.910406 | 2.091783792 | 1.064733742 | 4.00E−05 | 0.002498028 |
| A1cf | 260.0347413 | 128.8756936 | 522.3528365 | 4.053152474 | 2.019044449 | 4.10E−05 | 0.002547972 |
| Nme1 | 1295.632852 | 1577.577141 | 731.7442753 | 0.463840567 | −1.108299093 | 4.13E−05 | 0.002558093 |
| Ppp4r1l-ps | 377.6084717 | 216.3012158 | 700.2229834 | 3.237258658 | 1.694772642 | 4.16E−05 | 0.002565789 |
| 9530068E07Rik | 2280.043972 | 2695.076245 | 1449.979426 | 0.53801054 | −0.894293659 | 4.23E−05 | 0.002595107 |
| Dpysl2 | 1732.685632 | 2074.98697 | 1048.082954 | 0.505103391 | −0.985349368 | 4.24E−05 | 0.002595107 |
| Hist1h4d | 297.7060014 | 404.9058664 | 83.30627134 | 0.205742318 | −2.281089534 | 4.28E−05 | 0.002607945 |
| Zfp9 | 1483.363057 | 1127.991052 | 2194.107065 | 1.945145807 | 0.959878303 | 4.34E−05 | 0.002636423 |
| Snrnp70 | 898.2326662 | 636.9941721 | 1420.709654 | 2.230333835 | 1.157259668 | 4.65E−05 | 0.002809923 |
| 1500032L24Rik | 700.0585464 | 887.4154384 | 325.3447624 | 0.36662058 | −1.447640324 | 4.88E−05 | 0.002923773 |
| Surf4 | 5092.375572 | 5842.412602 | 3592.301511 | 0.61486611 | −0.701655803 | 4.89E−05 | 0.002923773 |
| Zcchc7 | 634.2945632 | 420.6458051 | 1061.592079 | 2.523719639 | 1.335551649 | 4.88E−05 | 0.002923773 |
| Cct5 | 1236.78048 | 1507.87363 | 694.5941813 | 0.460644823 | −1.118273296 | 4.96E−05 | 0.002952784 |
| Vegfa | 4479.943254 | 3733.272477 | 5973.284807 | 1.600013083 | 0.678083702 | 5.04E−05 | 0.002990147 |
| 2810407C02Rik | 4677.363403 | 5376.375047 | 3279.340114 | 0.609953749 | −0.713228244 | 5.11E−05 | 0.003016348 |
| Prr22 | 34.7834255 | 0.953038975 | 102.4441985 | 107.4921396 | 6.748087356 | 5.25E−05 | 0.003089182 |
| Unc80 | 4490.226046 | 3743.630744 | 5983.416651 | 1.598292423 | 0.676531387 | 5.58E−05 | 0.003267 |
| Ctsb | 7595.618513 | 8624.057127 | 5538.741284 | 0.642243112 | −0.638808583 | 5.65E−05 | 0.003295369 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Gcg | 6437.569918 | 8148.96167 | 3014.786414 | 0.369959577 | −1.434560448 | 5.72E−05 | 0.00332584 |
| Gpc6 | 27.39350364 | 0 | 82.18051092 | Inf | Inf | 5.85E−05 | 0.003389026 |
| Fbxl16 | 1315.452979 | 991.5163785 | 1963.326179 | 1.980124808 | 0.985591367 | 5.92E−05 | 0.003415321 |
| Ttll10 | 114.7332338 | 34.75707906 | 274.6855433 | 7.903009999 | 2.982402234 | 5.99E−05 | 0.003442825 |
| Zfp236 | 754.9879402 | 522.3197607 | 1220.324299 | 2.336354836 | 1.224259402 | 6.20E−05 | 0.00354946 |
| 2900005J15Rik | 93.24143118 | 23.34594293 | 233.0324077 | 9.981708958 | 3.319286839 | 6.23E−05 | 0.003554073 |
| Ikzf3 | 275.3225095 | 143.3641428 | 539.2392429 | 3.761325756 | 1.911241259 | 6.54E−05 | 0.003690809 |
| Romo1 | 333.450785 | 447.2654376 | 105.8214798 | 0.236596595 | −2.079498781 | 6.54E−05 | 0.003690809 |
| Rpl38 | 216.5089342 | 301.1224324 | 47.28193779 | 0.157018982 | −2.670989118 | 6.52E−05 | 0.003690809 |
| Cox6b1 | 812.71709 | 1089.613186 | 258.9248974 | 0.237630106 | −2.073210466 | 6.69E−05 | 0.003759072 |
| Kdelr2 | 4334.712904 | 4985.107186 | 3033.924341 | 0.608597615 | −0.716439416 | 6.92E−05 | 0.003877218 |
| Akap9 | 4850.95605 | 3886.769439 | 6779.32927 | 1.744206693 | 0.802571013 | 7.04E−05 | 0.003926638 |
| 9130011J15Rik | 1587.60084 | 1901.82732 | 959.1478808 | 0.504329636 | −0.987561088 | 7.09E−05 | 0.003939596 |
| B3gat2 | 36.22686558 | 1.429558463 | 105.8214798 | 74.02389099 | 6.209919066 | 7.39E−05 | 0.004091923 |
| Chgb | 45331.8843 | 39831.30066 | 56333.05159 | 1.414291039 | 0.500079035 | 7.47E−05 | 0.0041114 |
| Zfp280d | 723.1304097 | 498.7373314 | 1171.916601 | 2.349767238 | 1.232517854 | 7.48E−05 | 0.0041114 |
| Ndufb11 | 752.7061421 | 944.4345038 | 369.2494189 | 0.390974088 | −1.354855099 | 8.00E−05 | 0.004381781 |
| Cacna1c | 928.328995 | 670.3181807 | 1444.350623 | 2.154723928 | 1.107503037 | 8.03E−05 | 0.004383741 |
| Kcnc3 | 255.7027975 | 130.2581009 | 506.5921906 | 3.889141535 | 1.959451739 | 8.11E−05 | 0.004408328 |
| Gpr116 | 123.2672393 | 41.36640501 | 287.068908 | 6.939662944 | 2.794865594 | 8.20E−05 | 0.004414367 |
| Polr2j | 269.621827 | 367.2826465 | 74.30018795 | 0.202297028 | −2.305452967 | 8.20E−05 | 0.004414367 |
| Sall1 | 62.90341223 | 94.35511834 | 0 | 0 | #NAME? | 8.19E−05 | 0.004414367 |
| Rfx7 | 1219.369321 | 916.0622785 | 1825.983407 | 1.993296144 | 0.995156067 | 8.29E−05 | 0.004444825 |
| Atxn2l | 3564.834393 | 2700.568835 | 5293.325511 | 1.960063466 | 0.970900369 | 8.35E−05 | 0.004459771 |
| Gm10804 | 33.2824116 | 0.953038975 | 97.94115685 | 102.7672104 | 6.683236211 | 8.44E−05 | 0.004495045 |
| D17Wsu104e | 550.2777199 | 707.7746155 | 235.2839285 | 0.332427758 | −1.588887242 | 8.67E−05 | 0.004601629 |
| Csf2ra | 201.7046763 | 93.1655756 | 418.7828776 | 4.495038804 | 2.16833357 | 9.49E−05 | 0.005018856 |
| Syne1 | 1098.962409 | 817.632412 | 1661.622385 | 2.032236421 | 1.023068248 | 9.56E−05 | 0.005035259 |
| Ccdc162 | 193.2416733 | 87.22563368 | 405.2737525 | 4.646268939 | 2.216072664 | 0.000102502 | 0.00536655 |
| Mrps14 | 803.9980748 | 1001.108715 | 409.7767942 | 0.409322972 | −1.28868846 | 0.00010257 | 0.00536655 |
| Ankrd16 | 223.7081564 | 109.8472696 | 451.4299298 | 4.10961448 | 2.039003062 | 0.000104526 | 0.005431431 |
| BC005561 | 366.944317 | 216.62851 | 667.5759312 | 3.081662387 | 1.623708816 | 0.000104484 | 0.005431431 |
| Glul | 4214.51327 | 4834.640385 | 2974.259039 | 0.615197575 | −0.700878279 | 0.000106553 | 0.00551785 |
| Zfp92 | 935.5919879 | 681.2126701 | 1444.350623 | 2.120263886 | 1.084243833 | 0.000107485 | 0.005547198 |
| Dclre1c | 353.0553379 | 205.9268851 | 647.3122435 | 3.143408124 | 1.652329596 | 0.000107868 | 0.005548063 |
| Dhdh | 625.778481 | 423.6323278 | 1030.070788 | 2.431520732 | 1.281858892 | 0.000108577 | 0.005565664 |
| Lphn1 | 1582.849503 | 1235.567587 | 2277.413337 | 1.84321222 | 0.882222226 | 0.000112148 | 0.005715499 |
| Lrrcc1 | 409.9598862 | 250.7563322 | 728.366994 | 2.904680362 | 1.538379415 | 0.00011263 | 0.005715499 |
| Pisd-ps2 | 140.4864015 | 53.12314296 | 315.2129186 | 5.93362706 | 2.568914254 | 0.000112495 | 0.005715499 |
| Gm15708 | 25.51723627 | 0 | 76.5517088 | Inf | Inf | 0.000114407 | 0.005786301 |
| Tpr | 5227.129035 | 4429.639469 | 6822.108167 | 1.54010461 | 0.623028348 | 0.00011692 | 0.005893761 |
| D14Abb1e | 1112.692813 | 833.7249856 | 1670.628469 | 2.003812405 | 1.002747451 | 0.000121379 | 0.006098309 |
| BC024479 | 133.2115213 | 48.96538524 | 301.7037935 | 6.161572957 | 2.623298696 | 0.000122933 | 0.00615596 |
| Yod1 | 246.9572198 | 127.2715783 | 486.328503 | 3.82118702 | 1.934020869 | 0.000126799 | 0.006328696 |
| Cmpk1 | 2132.430309 | 2504.614153 | 1388.062602 | 0.554202109 | −0.851513733 | 0.00012749 | 0.006342321 |
| B230206F22Rik | 295.58024 | 164.1817749 | 558.3771701 | 3.400969263 | 1.765945967 | 0.000128505 | 0.006371898 |
| Atp6v0e | 981.0203647 | 1202.473806 | 538.1134824 | 0.447505368 | −1.160023108 | 0.000130094 | 0.006429695 |
| Evi2b | 31.7813977 | 0.953038975 | 93.43811515 | 98.04228115 | 6.615332147 | 0.000135467 | 0.006673499 |
| Rlf | 689.7138915 | 479.5709484 | 1109.999778 | 2.314568431 | 1.210743217 | 0.000138427 | 0.006797283 |
| Slc25a5 | 2246.645561 | 2630.906623 | 1478.123436 | 0.561830444 | −0.831793293 | 0.000140396 | 0.0068717 |
| Med12 | 1386.685294 | 1071.909482 | 2016.236919 | 1.880976847 | 0.911482091 | 0.000143211 | 0.006986941 |
| A2ld1 | 278.3589763 | 375.8853288 | 83.30627134 | 0.221626823 | −2.173795595 | 0.000143993 | 0.007002571 |
| E030024N20Rik | 108.9182815 | 35.04703401 | 256.760766 | 7.324999999 | 2.872828759 | 0.000149319 | 0.007215341 |
| Ggt7 | 234.4704889 | 119.2362058 | 464.9390549 | 3.89931105 | 1.963219244 | 0.000149026 | 0.007215341 |
| Dad1 | 1893.443774 | 2233.380793 | 1213.569737 | 0.543377887 | −0.879972239 | 0.000152901 | 0.007364973 |
| 2310016M24Rik | 395.7665988 | 518.2239499 | 150.8518968 | 0.291094028 | −1.780442855 | 0.000154054 | 0.007397015 |
| Tmem66 | 2746.161887 | 3396.504638 | 1445.476384 | 0.425577627 | −1.232505786 | 0.000156668 | 0.007498825 |
| Kifc2 | 93.789618 | 26.41974401 | 228.529366 | 8.649946264 | 3.11269117 | 0.000157365 | 0.007508507 |
| 2010015L04Rik | 123.0352146 | 43.83276893 | 281.4401059 | 6.4207695 | 2.682746208 | 0.000161306 | 0.007646262 |
| Atp1b3 | 1025.848352 | 1251.14074 | 575.2635764 | 0.459791259 | −1.120949055 | 0.000162268 | 0.007646262 |
| Itsn2 | 905.7570125 | 662.915577 | 1391.439883 | 2.098969962 | 1.069681521 | 0.000161859 | 0.007646262 |
| Pcf11 | 1280.394084 | 982.8326158 | 1875.516866 | 1.908276838 | 0.932270482 | 0.000161837 | 0.007646262 |
| Slc25a23 | 1401.828709 | 1086.744281 | 2031.997564 | 1.869802859 | 0.902886169 | 0.00016525 | 0.007738718 |
| Dvl3 | 934.4881156 | 688.0000649 | 1427.464217 | 2.074802445 | 1.052973975 | 0.000165776 | 0.007739431 |
| 1700110K17Rik | 145.6273557 | 58.58305344 | 319.7159603 | 5.457482011 | 2.44823547 | 0.000166609 | 0.007754458 |
| Abcc8 | 9727.155573 | 7912.155143 | 13357.15673 | 1.688179716 | 0.755468495 | 0.000169805 | 0.007855446 |
| Zfp788 | 524.2312206 | 346.7373855 | 879.2188908 | 2.535691066 | 1.342378987 | 0.000169814 | 0.007855446 |
| Atp5o | 691.1031771 | 865.5391812 | 342.2311688 | 0.395396507 | −1.33862797 | 0.000171152 | 0.007869345 |
| Rpl22l1 | 585.9680708 | 742.735095 | 272.4340225 | 0.36679837 | −1.446940865 | 0.000170912 | 0.007869345 |
| 6430550D23Rik | 31.00179794 | 0.909399752 | 91.18659431 | 100.2711888 | 6.647763322 | 0.000172453 | 0.007905241 |
| Scai | 482.182625 | 313.4971434 | 819.5535883 | 2.614229844 | 1.386385989 | 0.000179788 | 0.008216614 |
| Txn1 | 1003.886864 | 1224.39019 | 562.8802118 | 0.459722902 | −1.121163555 | 0.000183309 | 0.008352378 |
| Tkt | 429.4814108 | 557.5385636 | 173.3671052 | 0.310950877 | −1.685241409 | 0.000185044 | 0.008406196 |
| Hsp90ab1 | 14057.50101 | 15688.23028 | 10796.04246 | 0.688161907 | −0.539180061 | 0.000185824 | 0.00841643 |
| Psmb1 | 745.4608295 | 927.3748524 | 381.6327836 | 0.411519444 | −1.280967497 | 0.000186695 | 0.008430712 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Gpatch8 | 1140.099341 | 792.6542671 | 1834.98949 | 2.314993518 | 1.211008154 | 0.000192498 | 0.008666998 |
| Rps28 | 337.9538267 | 447.2654376 | 119.3306049 | 0.266800416 | −1.906167178 | 0.000196341 | 0.008813862 |
| Atp5c1 | 2235.448076 | 2636.625604 | 1433.093019 | 0.543532998 | −0.879560471 | 0.000205123 | 0.009162496 |
| Baz2b | 2131.53271 | 1727.618832 | 2939.360466 | 1.701394087 | 0.766717345 | 0.000205315 | 0.009162496 |
| Nr1d1 | 877.8330844 | 642.9820131 | 1347.535227 | 2.095758823 | 1.067472703 | 0.000210042 | 0.00934596 |
| P4hb | 9332.699297 | 10463.59834 | 7070.90122 | 0.675761912 | −0.565413056 | 0.000211959 | 0.009403657 |
| Whsc1l1 | 2403.408931 | 1964.317579 | 3281.591635 | 1.670601368 | 0.740367524 | 0.00021287 | 0.009416544 |
| Ankrd11 | 2818.034821 | 2197.869067 | 4058.366327 | 1.846500498 | 0.884793651 | 0.000217595 | 0.009562485 |
| D10Bwg1379e | 4853.095619 | 4063.908779 | 6431.4693 | 1.582582103 | 0.662280347 | 0.000217575 | 0.009562485 |
| Fam195b | 465.3717136 | 624.3202627 | 147.4746155 | 0.236216289 | −2.081819642 | 0.00021869 | 0.009562485 |
| Iffo1 | 235.2368718 | 122.6373011 | 460.4360132 | 3.754453247 | 1.908602826 | 0.000218097 | 0.009562485 |
| Churc1 | 396.3338028 | 516.823235 | 155.3549384 | 0.300595886 | −1.734102828 | 0.000220284 | 0.009604495 |
| Evi2a | 23.64096889 | 0 | 70.92290668 | Inf | Inf | 0.000223675 | 0.009669026 |
| Runx2 | 23.64096889 | 0 | 70.92290668 | Inf | Inf | 0.000223675 | 0.009669026 |
| Srxn1 | 1490.202843 | 1773.17961 | 924.2493077 | 0.521238403 | −0.939984715 | 0.000223131 | 0.009669026 |
| Arhgap12 | 744.5430173 | 532.5448661 | 1168.53932 | 2.194255159 | 1.133731299 | 0.000227086 | 0.009788583 |
| Wdr6 | 659.1747904 | 871.1202213 | 235.2839285 | 0.270093522 | −1.888469058 | 0.000228419 | 0.009818127 |
| Mtap2 | 1914.758485 | 1539.237385 | 2665.800683 | 1.731897047 | 0.792353172 | 0.000230391 | 0.009874919 |
| Sfi1 | 282.3582662 | 158.9836998 | 529.1073991 | 3.328060674 | 1.734681735 | 0.000231786 | 0.009906714 |
| Bclaf1 | 3363.903138 | 2673.314614 | 4745.080185 | 1.774980079 | 0.827802833 | 0.000232541 | 0.009911081 |
| Eif3l | 1206.838133 | 1456.768427 | 706.977546 | 0.485305374 | −1.04303526 | 0.000234793 | 0.009979014 |
| Solh | 149.0769691 | 62.6317131 | 321.9674811 | 5.140646251 | 2.361949738 | 0.000238913 | 0.010125792 |
| Bax | 280.8048949 | 376.7398056 | 88.93507346 | 0.236064977 | −2.08274408 | 0.000240528 | 0.01013757 |
| Grik5 | 302.6832224 | 174.8362486 | 558.3771701 | 3.193715145 | 1.675235628 | 0.000240213 | 0.01013757 |
| Cpe | 32594.00207 | 36064.65172 | 25652.70277 | 0.711297671 | −0.491474655 | 0.000247654 | 0.010380277 |
| Cxxc1 | 738.9059749 | 529.7181047 | 1157.281715 | 2.184712407 | 1.127443377 | 0.000246992 | 0.010380277 |
| Gipr | 281.4715472 | 158.2165014 | 527.9816386 | 3.337083261 | 1.738587683 | 0.000249629 | 0.010434218 |
| 4932413F04Rik | 52.9559206 | 7.94809401 | 142.9715738 | 17.98815373 | 4.168975586 | 0.000253429 | 0.010535006 |
| Agrn | 127.0032042 | 48.09611275 | 284.8173872 | 5.92183798 | 2.566045019 | 0.000253288 | 0.010535006 |
| Nog | 23.26571542 | 0 | 69.79714626 | Inf | Inf | 0.000255771 | 0.01060331 |
| 0610007C21Rik | 973.5953856 | 1223.983389 | 472.8193779 | 0.386295584 | −1.372222911 | 0.000256474 | 0.010603504 |
| Airn | 169.3754678 | 72.25289326 | 363.6206168 | 5.032609774 | 2.331306736 | 0.000258725 | 0.010609813 |
| Ccdc88b | 50.48793314 | 7.060513868 | 137.3427717 | 19.45223453 | 4.281863986 | 0.000258339 | 0.010609813 |
| Ptpn13 | 398.474222 | 250.4142424 | 694.5941813 | 2.773780655 | 1.471853707 | 0.000258105 | 0.010609813 |
| Zfp618 | 131.9119218 | 51.51902761 | 292.6977101 | 5.681351604 | 2.50623419 | 0.000261347 | 0.010688469 |
| BC051142 | 53.87864313 | 8.206417383 | 145.2230946 | 17.69628424 | 4.145374559 | 0.000262993 | 0.010726877 |
| Pax6 | 3069.499802 | 2560.431654 | 4087.636078 | 1.596463663 | 0.674879716 | 0.000270125 | 0.010988238 |
| Cep350 | 1645.041635 | 1310.843618 | 2313.43767 | 1.764846423 | 0.819542646 | 0.000279156 | 0.011325235 |
| Prdx3 | 501.9419165 | 640.3368325 | 225.1520847 | 0.351615077 | −1.507931161 | 0.000283536 | 0.011472228 |
| Psmb6 | 835.4554358 | 1026.342428 | 453.6814507 | 0.44203712 | −1.177760572 | 0.00028478 | 0.011491939 |
| Rps21 | 833.0553918 | 1023.305243 | 452.5556903 | 0.442248971 | −1.17706931 | 0.000289137 | 0.011636817 |
| Mll2 | 2536.130805 | 1914.607336 | 3779.177742 | 1.973865696 | 0.981023831 | 0.000292053 | 0.011692119 |
| Zfp398 | 447.3137015 | 289.9006489 | 762.1398067 | 2.628968958 | 1.394497107 | 0.000291306 | 0.011692119 |
| Npc2 | 1378.54365 | 1641.715155 | 852.2006406 | 0.519091657 | −0.945938793 | 0.00029784 | 0.011892448 |
| Ankhd1 | 3201.155129 | 2681.925816 | 4239.843755 | 1.58080948 | 0.660663504 | 0.000298759 | 0.011897826 |
| Prss53 | 7565.5501 | 8841.256686 | 5014.136926 | 0.567129437 | −0.818250053 | 0.000299823 | 0.011908933 |
| Cadps | 3166.584731 | 2649.771026 | 4200.21214 | 1.585122676 | 0.664594498 | 0.000302501 | 0.011983947 |
| Tanc2 | 1532.331003 | 1213.263457 | 2170.466097 | 1.78894871 | 0.839112026 | 0.000314776 | 0.012437759 |
| Cox6c | 713.1898575 | 884.5671793 | 370.6713594 | 0.418693594 | −1.25603325 | 0.000315848 | 0.012447694 |
| Uimc1 | 422.0585706 | 271.1558798 | 723.8639523 | 2.669549164 | 1.416596119 | 0.000317777 | 0.012491252 |
| Gabarapl1 | 1363.391882 | 1623.490544 | 843.1945572 | 0.5193714 | −0.945161522 | 0.00032391 | 0.012699433 |
| Tomm7 | 217.8532907 | 297.510165 | 58.53954202 | 0.196764847 | −2.345455597 | 0.000326048 | 0.012732379 |
| Vwa5b2 | 1230.383394 | 954.5257154 | 1782.07985 | 1.866958692 | 0.900690007 | 0.000326428 | 0.012732379 |
| Map3k14 | 140.1265181 | 58.21212004 | 303.9553144 | 5.221512532 | 2.384467777 | 0.000329725 | 0.012827977 |
| Prpf38b | 913.3280259 | 680.4637794 | 1379.056519 | 2.026642065 | 1.01909131 | 0.000330997 | 0.012844556 |
| Psmb10 | 220.0374798 | 300.2235685 | 59.66530245 | 0.198736238 | −2.331073137 | 0.000333138 | 0.012894632 |
| Arpc5l | 917.8574896 | 1118.987097 | 515.598274 | 0.460772314 | −1.117874062 | 0.00033628 | 0.012950202 |
| Spcs1 | 1377.401026 | 1654.636104 | 822.3098696 | 0.497348552 | −1.00767082 | 0.000335711 | 0.012950202 |
| Rapgef6 | 972.4477975 | 731.9933429 | 1453.356707 | 1.985478039 | 0.989486403 | 0.000339769 | 0.013051447 |
| Golga4 | 6427.309589 | 5558.394208 | 8165.140352 | 1.46897468 | 0.554809529 | 0.000350347 | 0.01342376 |
| Bcl9 | 1008.891503 | 765.2694525 | 1496.135603 | 1.955044198 | 0.967201223 | 0.000365463 | 0.013905205 |
| Psmd8 | 712.1409072 | 882.6459897 | 371.5009398 | 0.420982894 | −1.248166482 | 0.000365661 | 0.013905205 |
| Smg1 | 2186.936473 | 1791.586549 | 2977.63632 | 1.66201087 | 0.732929818 | 0.0003652 | 0.013905205 |
| Atox1 | 346.7473263 | 454.2640046 | 131.7139696 | 0.289950267 | −1.786122627 | 0.000376609 | 0.014250102 |
| Celsr3 | 858.9289187 | 638.2667335 | 1300.253289 | 2.037162868 | 1.026561326 | 0.000375867 | 0.014250102 |
| Atp6v1b2 | 3451.60437 | 3943.01025 | 2468.792609 | 0.62611874 | −0.675491813 | 0.000378227 | 0.014275718 |
| Pion | 157.448117 | 70.6853932 | 330.9735645 | 4.682347364 | 2.227231966 | 0.000379817 | 0.014300162 |
| Adi1 | 4677.014425 | 5295.35971 | 3440.323854 | 0.649686526 | −0.62218431 | 0.000382109 | 0.01435084 |
| Mdn1 | 1031.257631 | 785.8724005 | 1522.028093 | 1.93673692 | 0.953627996 | 0.000384277 | 0.014368374 |
| Ndufa13 | 656.2767273 | 817.2390458 | 334.3508458 | 0.409122145 | −1.289396466 | 0.00038447 | 0.014368374 |
| Slc25a39 | 1090.792858 | 1313.096046 | 646.1864831 | 0.492109077 | −1.022949967 | 0.00038818 | 0.014471404 |
| Dstn | 3447.707503 | 3938.290711 | 2466.541088 | 0.626297363 | −0.67508029 | 0.000397218 | 0.014772025 |
| Srsf5 | 1754.435378 | 1413.017408 | 2437.271317 | 1.724869986 | 0.786487621 | 0.000398645 | 0.014788857 |
| AW549877 | 1289.376304 | 1008.689388 | 1850.750136 | 1.834806789 | 0.87562815 | 0.000410103 | 0.015176796 |
| Nbea | 2801.377968 | 2340.059211 | 3724.015481 | 1.591419338 | 0.670314035 | 0.000414807 | 0.015276388 |

TABLE 7-continued

Complete list of differentially expressed transcripts in wild-type ALDH⁻ vs. ALDH⁺ cells

| Gene | baseMean all | baseMean ALDH- | baseMean ALDH+ | Fold-Change | log2 Fold-Change | p-value | Adjusted p-value |
|---|---|---|---|---|---|---|---|
| Prpf4b | 1951.959458 | 1589.972923 | 2675.932527 | 1.683005092 | 0.751039542 | 0.000413996 | 0.015276388 |
| Laptm4a | 1618.280495 | 1905.067906 | 1044.705673 | 0.54838238 | -0.866745877 | 0.000417648 | 0.015343752 |
| Appl2 | 673.7196046 | 483.1606484 | 1054.837517 | 2.183202461 | 1.126445926 | 0.000422857 | 0.015434151 |
| Fam178a | 1708.307217 | 1375.909339 | 2373.102973 | 1.724752427 | 0.786389291 | 0.000422743 | 0.015434151 |
| Pex5l | 639.6020937 | 453.9367104 | 1010.93286 | 2.22703482 | 1.155124115 | 0.00042316 | 0.015434151 |
| Manf | 1808.547651 | 2116.731333 | 1192.180289 | 0.563217575 | -0.828235741 | 0.000434955 | 0.015819649 |
| Prnd | 37.42485217 | 3.226538356 | 105.8214798 | 32.79721737 | 5.035501511 | 0.000435815 | 0.015819649 |
| 1700029J07Rik | 161.8634803 | 74.49403714 | 336.6023666 | 4.518514227 | 2.175848465 | 0.000448383 | 0.016209421 |
| Rps6kb2 | 246.8180858 | 137.194721 | 466.0648153 | 3.397104581 | 1.764305633 | 0.000448689 | 0.016209421 |
| Chchd2 | 658.3810546 | 817.5817579 | 339.9796479 | 0.415835658 | -1.265914621 | 0.000469585 | 0.016924027 |
| Mll5 | 3155.695394 | 2659.329511 | 4148.427161 | 1.55995229 | 0.641501906 | 0.000477682 | 0.017141462 |
| Sdf2l1 | 1237.150686 | 1475.219005 | 761.0140463 | 0.515865132 | -0.95493416 | 0.000477878 | 0.017141462 |
| Mrfap1 | 5077.086838 | 6082.90744 | 3065.445633 | 0.503944152 | -0.988664234 | 0.000482878 | 0.017279968 |
| Rpl22 | 1128.919362 | 1352.836516 | 681.0850562 | 0.50344964 | -0.990080623 | 0.000488305 | 0.017393076 |
| Uba7 | 135.9806186 | 57.0591926 | 293.8234705 | 5.149450196 | 2.364418405 | 0.000488331 | 0.017393076 |
| Ica1l | 356.9559138 | 223.5982334 | 623.6712746 | 2.789249562 | 1.479877022 | 0.000493727 | 0.017544058 |
| Hivep1 | 1405.956039 | 1114.324725 | 1989.218668 | 1.785133745 | 0.836032167 | 0.000498858 | 0.017684984 |
| Dus3l | 209.0219959 | 109.207477 | 408.6510337 | 3.741969369 | 1.903797749 | 0.000505869 | 0.017880046 |
| Rer1 | 948.1427097 | 1148.091401 | 548.2453263 | 0.477527595 | -1.066343989 | 0.00050744 | 0.017880046 |
| Whamm | 273.1799672 | 158.7253764 | 502.0891489 | 3.163256942 | 1.661410747 | 0.000507896 | 0.017880046 |
| Myt1 | 910.884993 | 687.4939541 | 1357.667071 | 1.974805833 | 0.981710812 | 0.000511283 | 0.017957622 |
| 1810046J19Rik | 1171.629764 | 1442.794608 | 629.3000768 | 0.436167472 | -1.197045913 | 0.00051498 | 0.01802971 |
| BC031181 | 952.4015143 | 1152.228087 | 552.748368 | 0.47972131 | -1.059731566 | 0.000515712 | 0.01802971 |
| Fryl | 2040.770487 | 1673.656008 | 2774.999444 | 1.658046475 | 0.729484446 | 0.000518771 | 0.018036776 |
| Hap1 | 1443.756477 | 1120.929043 | 2089.411346 | 1.863999652 | 0.898401591 | 0.000518773 | 0.018036776 |
| Maml3 | 948.419958 | 719.5925525 | 1406.074769 | 1.953987384 | 0.966421152 | 0.000520616 | 0.018036776 |
| Znf512b | 799.2369739 | 592.6334727 | 1212.443976 | 2.045858076 | 1.032706067 | 0.000520669 | 0.018036776 |
| Epcam | 1621.133607 | 1904.281652 | 1054.837517 | 0.55392936 | -0.852226087 | 0.000522356 | 0.018054016 |
| Itgb2l | 31.66625007 | 1.90607795 | 91.18659431 | 47.83990827 | 5.580142718 | 0.000524893 | 0.018059418 |
| Mir665 | 41.0628511 | 4.743375265 | 113.7018028 | 23.97065305 | 4.583197309 | 0.000523976 | 0.018059418 |
| Nedd8 | 530.5532954 | 668.6190152 | 254.4218557 | 0.380518427 | -1.393961777 | 0.00053164 | 0.018250166 |
| Ush2a | 927.4775535 | 701.1251623 | 1380.182279 | 1.968524813 | 0.977114898 | 0.000535073 | 0.018326555 |
| Crip1 | 197.5033945 | 270.362602 | 51.78497948 | 0.191538989 | -2.384290002 | 0.000537396 | 0.018364651 |
| Cep290 | 1085.302475 | 838.795655 | 1578.316114 | 1.881645553 | 0.911994892 | 0.000541629 | 0.018385085 |
| Runx1t1 | 1614.302253 | 1299.633118 | 2243.640524 | 1.726364535 | 0.787737133 | 0.000541607 | 0.018385085 |
| Tmed3 | 1715.759039 | 2009.632586 | 1128.011944 | 0.561302574 | -0.833149418 | 0.000539456 | 0.018385085 |
| BC065397 | 43.45810653 | 5.521857349 | 119.3066049 | 21.61059175 | 4.433666672 | 0.000545739 | 0.018483266 |
| Luc7l3 | 1473.959255 | 1178.053694 | 2065.770377 | 1.75354518 | 0.810274602 | 0.00054705 | 0.018486393 |
| F8a | 227.3689221 | 307.2805704 | 67.54562541 | 0.21981743 | -2.185622306 | 0.000551724 | 0.018602912 |
| Tbca | 825.4011635 | 1006.757978 | 462.6875341 | 0.459581691 | -1.12160677 | 0.000557131 | 0.018743566 |
| Chd3 | 522.4277092 | 359.7927643 | 847.6975989 | 2.356071836 | 1.236383528 | 0.000559521 | 0.018782335 |
| Rcbtb2 | 307.0383767 | 185.3091414 | 550.4968471 | 2.970694499 | 1.570800249 | 0.000564548 | 0.018909246 |
| Khdrbs2 | 21.01419457 | 0 | 63.04258372 | Inf | Inf | 0.000571753 | 0.019108376 |
| Ndufb8 | 615.7630674 | 813.8829599 | 219.5232826 | 0.269723404 | -1.890447383 | 0.000579175 | 0.019313885 |
| Alkbh7 | 147.8778485 | 207.1818867 | 29.26977101 | 0.141275724 | -2.823414514 | 0.000584317 | 0.019400077 |
| Ptpn2 | 652.1793741 | 469.4253498 | 1017.687423 | 2.167943046 | 1.116326856 | 0.00058336 | 0.019400077 |
| Rufy3 | 1153.91926 | 900.6305784 | 1660.496625 | 1.843704472 | 0.882607424 | 0.00059804 | 0.019791029 |
| Tspan31 | 1191.429362 | 1420.146145 | 733.9957961 | 0.516845255 | -0.952195698 | 0.0005987 | 0.019791029 |
| Lrrc4 | 194.1739491 | 79.05508376 | 424.4116797 | 5.368556448 | 2.424534214 | 0.000610591 | 0.020140223 |
| Kcnab1 | 41.6830522 | 5.110796695 | 114.8275632 | 22.46764449 | 4.489776975 | 0.000615647 | 0.020206063 |
| Mrpl46 | 172.2068286 | 238.0465553 | 40.52737525 | 0.170249787 | -2.554275105 | 0.000617935 | 0.020206063 |
| Pdia6 | 3177.050946 | 3629.684151 | 2271.784535 | 0.625890419 | -0.676018003 | 0.000617577 | 0.020206063 |
| Rpl36al | 1398.515829 | 1651.972616 | 891.6022554 | 0.539719755 | -0.8897711 | 0.000614025 | 0.020206063 |
| Spag9 | 1168.436595 | 879.0648034 | 1747.180177 | 1.98754423 | 0.990986966 | 0.000619246 | 0.020206063 |
| Ampd3 | 26.88855612 | 0.931219364 | 78.80322965 | 84.62370168 | 6.40298989 | 0.000622387 | 0.020264985 |
| Cstb | 763.4571514 | 935.2314082 | 419.908638 | 0.448989025 | -1.155247915 | 0.000627917 | 0.020401256 |
| Rps25 | 1104.27209 | 1320.93153 | 670.9532124 | 0.507939433 | -0.977271615 | 0.000635685 | 0.020609513 |
| Cd300lf | 20.6389411 | 0 | 61.91682329 | Inf | Inf | 0.000653768 | 0.021105565 |
| Sema6d | 330.946817 | 205.9740363 | 580.8923785 | 2.820221369 | 1.495808409 | 0.000652498 | 0.021105565 |
| Aldoa | 5192.717537 | 6099.872789 | 3378.407031 | 0.553848768 | -0.852436001 | 0.000656669 | 0.021124089 |
| Gabbr1 | 146.1321152 | 66.09475522 | 306.2068352 | 4.632846195 | 2.211898787 | 0.000657126 | 0.021124089 |
| Aak1 | 3365.0818 | 2623.297627 | 4848.650144 | 1.848303484 | 0.886201661 | 0.000660847 | 0.021198797 |
| Krba1 | 259.9112952 | 150.6428528 | 478.44818 | 3.176043013 | 1.667230451 | 0.000679616 | 0.021754887 |
| Akap8 | 779.2412833 | 578.4005828 | 1180.922684 | 2.041703828 | 1.029773603 | 0.000681348 | 0.021764404 |
| Tnrc6b | 2366.995621 | 1969.362917 | 3162.26103 | 1.605727925 | 0.683227462 | 0.000684216 | 0.021810089 |
| Lman2 | 3657.653258 | 4151.328045 | 2670.303725 | 0.64324208 | -0.636569088 | 0.000687244 | 0.021860689 |
| Cox8a | 1518.438619 | 1783.449103 | 988.4176519 | 0.554216911 | -0.851477363 | 0.000706031 | 0.022364515 |
| Ccnt2 | 596.4629487 | 426.3780868 | 936.6326724 | 2.196718596 | 1.13535007 | 0.000743902 | 0.023515057 |
| Fkbp14 | 184.7473733 | 94.74787135 | 364.7463772 | 3.849652473 | 1.944728212 | 0.000756266 | 0.023757389 |
| Ptbp2 | 184.4326468 | 94.83046876 | 363.6206168 | 3.834096876 | 1.938886679 | 0.000754277 | 0.023757389 |
| Ssh3 | 144.1534112 | 65.37822001 | 301.7037935 | 4.614744688 | 2.206250833 | 0.000755994 | 0.023757389 |
| Safb2 | 559.1832936 | 394.6624534 | 888.2249742 | 2.250594062 | 1.170305863 | 0.000758023 | 0.0237634 |
| Senp7 | 663.766432 | 462.6020875 | 1066.095121 | 2.304561847 | 1.204492485 | 0.000761311 | 0.02381727 |
| Zmym5 | 762.9349799 | 566.8873725 | 1155.030195 | 2.037495013 | 1.026796528 | 0.000766089 | 0.023917416 |
| BC018242 | 242.7182727 | 138.3624442 | 451.4299298 | 3.262662296 | 1.706049668 | 0.000769702 | 0.023980865 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Sdcbp | 2121.570664 | 2452.300362 | 1460.111269 | 0.595404744 | −0.748057378 | 0.000773121 | 0.024038045 |
| Atp6v0d1 | 2125.116808 | 2455.930937 | 1463.488551 | 0.595899717 | −0.746858532 | 0.00077602 | 0.024052844 |
| D8Ertd738e | 277.4724453 | 366.6752093 | 99.06691727 | 0.270176207 | −1.888027465 | 0.00077747 | 0.024052844 |
| Nsd1 | 3903.239117 | 3346.664452 | 5016.388447 | 1.498921843 | 0.58392516 | 0.000778353 | 0.024052844 |
| Hirip3 | 303.8164233 | 185.5421332 | 540.3650033 | 2.912357392 | 1.542187408 | 0.000786068 | 0.024241879 |
| Sil1 | 442.923922 | 563.0674449 | 202.6368762 | 0.359880292 | −1.474410998 | 0.000794428 | 0.024450007 |
| Mapk15 | 219.9567632 | 121.6694664 | 416.5313567 | 3.423466618 | 1.775457945 | 0.000803466 | 0.024648391 |
| Tmem86b | 76.26652275 | 22.0874294 | 184.6247095 | 8.358813792 | 3.063298222 | 0.000804123 | 0.024648391 |
| 4833439L19Rik | 4037.965552 | 4560.812725 | 2992.271206 | 0.656082893 | −0.608049991 | 0.000813269 | 0.02487848 |
| Stard8 | 87.35222925 | 28.58414533 | 204.8883971 | 7.16790356 | 2.841551227 | 0.000816388 | 0.024923663 |
| Sec61b | 930.1985269 | 1173.522987 | 443.5496069 | 0.37796414 | −1.403678731 | 0.000818464 | 0.024936869 |
| Vldlr | 3406.633258 | 2906.836738 | 4406.226298 | 1.515814851 | 0.600093547 | 0.000831882 | 0.025294889 |
| Psma2 | 1095.405043 | 1307.068077 | 672.0789728 | 0.514188193 | −0.959631612 | 0.000842252 | 0.025558978 |
| Nkrf | 285.73374 | 376.2527502 | 104.6957194 | 0.278259014 | −1.84549967 | 0.00084659 | 0.025639333 |
| Atp5a1 | 5804.75574 | 6810.790177 | 3792.686867 | 0.556864441 | −0.844601923 | 0.000857639 | 0.025870698 |
| Pcdhgc5 | 37.64131879 | 4.114118497 | 104.6957194 | 25.44791052 | 4.669475299 | 0.000856268 | 0.025870698 |
| Ptpmt1 | 145.9927287 | 203.7913273 | 30.39553144 | 0.14915027 | −2.745161508 | 0.000863764 | 0.026003753 |
| E130307A14Rik | 40.22567752 | 5.176255529 | 110.3245215 | 21.31357714 | 4.413700841 | 0.000872731 | 0.026221675 |
| Spnb3 | 525.63554 | 368.544672 | 839.817276 | 2.278739431 | 1.188235965 | 0.000876622 | 0.026286546 |
| Slc8a1 | 3483.224866 | 2976.693734 | 4496.287132 | 1.51049706 | 0.595023376 | 0.000886071 | 0.026517478 |
| C430048L16Rik | 209.0390955 | 113.7361681 | 399.6449504 | 3.513789475 | 1.813027756 | 0.000898035 | 0.026822616 |
| 1700034H15Rik | 29.73179707 | 1.818799505 | 85.55779219 | 47.04080464 | 5.555840833 | 0.000901572 | 0.026875333 |
| Zfml | 1533.150333 | 1240.38494 | 2118.681117 | 1.708083554 | 0.772378549 | 0.000910068 | 0.027075409 |
| Ndufb2 | 319.5876039 | 416.3388221 | 126.2851674 | 0.302842587 | −1.723359523 | 0.000918555 | 0.027274428 |
| 2900010M23Rik | 485.9971948 | 611.9167081 | 234.1581621 | 0.382663465 | −1.385851928 | 0.000923456 | 0.027366411 |
| Ins1 | 2373536.279 | 2590036.277 | 1940536.285 | 0.749231315 | −0.416516896 | 0.000930546 | 0.027522748 |
| BC018507 | 976.3485853 | 754.1680507 | 1420.709654 | 1.883810449 | 0.913653807 | 0.000937625 | 0.027644699 |
| Tmem146 | 67.0886237 | 17.88954441 | 165.4867823 | 9.250474938 | 3.209527438 | 0.000938313 | 0.027644699 |
| Atp6v1f | 476.8921888 | 634.2835327 | 162.109501 | 0.255578921 | −1.96815924 | 0.000947641 | 0.027859186 |
| Zfp692 | 106.0492187 | 41.43186385 | 235.2839285 | 5.678815932 | 2.50559015 | 0.000949265 | 0.027859186 |
| C030046E11Rik | 457.2330913 | 312.0971763 | 747.5049212 | 2.395103122 | 1.260087773 | 0.000962917 | 0.028150931 |
| Etl4 | 1203.492025 | 918.7017036 | 1773.072667 | 1.929976466 | 0.948583255 | 0.000961991 | 0.028150931 |
| Dusp3 | 1062.966636 | 1267.979431 | 652.9410456 | 0.514946086 | −0.957506702 | 0.000967131 | 0.028219777 |
| Hint1 | 679.9808002 | 834.7836106 | 370.3751793 | 0.443678068 | −1.172414856 | 0.0009723 | 0.028316135 |
| Rplp0 | 897.1549895 | 1081.178785 | 529.1073991 | 0.489380116 | −1.03097261 | 0.000975463 | 0.028353845 |
| Klhl20 | 287.2233684 | 175.2874365 | 511.0952323 | 2.915755073 | 1.543869537 | 0.000980898 | 0.028402975 |
| Mll1 | 3636.861026 | 2663.968569 | 5582.64594 | 2.09561254 | 1.067372 | 0.00097906 | 0.028402975 |
| Hnrnph1 | 2592.480979 | 2183.757307 | 3409.928323 | 1.56149601 | 0.642928883 | 0.00098806 | 0.028555889 |
| Fkbp1a | 3277.474013 | 3755.552023 | 2321.317993 | 0.618103006 | −0.694080815 | 0.00099458 | 0.028580993 |
| Gnb2 | 373.5084715 | 479.7708369 | 160.9837406 | 0.335542989 | −1.575430483 | 0.000991953 | 0.028580993 |
| Map4k3 | 764.0883155 | 571.9946573 | 1148.275632 | 2.007493632 | 1.005395411 | 0.000994401 | 0.028580993 |
| Akr1a1 | 2549.077547 | 2916.816299 | 1813.600042 | 0.62177383 | −0.685538198 | 0.001002252 | 0.028730874 |
| Phldb2 | 1375.275568 | 1104.328351 | 1917.170001 | 1.736050695 | 0.795809077 | 0.001003583 | 0.028730874 |
| Zfp169 | 359.6128166 | 233.2123896 | 612.4136704 | 2.625991146 | 1.392862052 | 0.001012249 | 0.028924395 |
| 9330159F19Rik | 211.4513446 | 116.7916615 | 400.7707108 | 3.431501064 | 1.778839082 | 0.001031272 | 0.029357397 |
| Cblb | 864.1363227 | 659.5869645 | 1273.235039 | 1.930352035 | 0.948863973 | 0.001029859 | 0.029357397 |
| Kidins220 | 4387.981643 | 3795.152536 | 5573.639857 | 1.468620775 | 0.554461913 | 0.001035547 | 0.029423896 |
| Atxn7l3b | 1088.126778 | 1295.02492 | 674.3304937 | 0.520708508 | −0.941452116 | 0.001040059 | 0.029496843 |
| Akap13 | 6731.80557 | 5909.316699 | 8376.783311 | 1.417555318 | 0.503405035 | 0.001043121 | 0.029528505 |
| 2410015M20Rik | 416.9733796 | 530.3333136 | 190.2535116 | 0.358743278 | −1.478976294 | 0.001047285 | 0.029591151 |
| Snx3 | 891.0935481 | 1073.212383 | 526.8558782 | 0.490914833 | −1.026455335 | 0.001064229 | 0.029958341 |
| Srrm1 | 2324.150683 | 1947.874405 | 3076.703237 | 1.579518284 | 0.659484637 | 0.001062643 | 0.029958341 |
| Mipep | 197.8278789 | 268.0429275 | 57.4137816 | 0.214220621 | −2.222952202 | 0.001067653 | 0.029999085 |
| Lair1 | 40.52881077 | 5.630955406 | 110.3245215 | 19.59250492 | 4.292229954 | 0.001083877 | 0.030398642 |
| Lpp | 4942.364466 | 4296.316086 | 6234.461225 | 1.451117911 | 0.537164751 | 0.001086948 | 0.030428524 |
| Dcp1a | 806.0521858 | 609.6108532 | 1198.934851 | 1.96672163 | 0.975792773 | 0.001090804 | 0.030480247 |
| Nemf | 1210.220006 | 961.4407278 | 1707.778562 | 1.776270251 | 0.828851097 | 0.001095803 | 0.030546626 |
| Polr2g | 628.1014976 | 773.8510631 | 336.6023666 | 0.434970745 | −1.201010609 | 0.001097206 | 0.030546626 |
| Atxn1 | 935.8649823 | 721.5866567 | 1364.421633 | 1.89086317 | 0.919044968 | 0.001104759 | 0.03059486 |
| Cobra1 | 405.9622397 | 271.7781126 | 674.3304937 | 2.48118028 | 1.311026564 | 0.001104988 | 0.03059486 |
| Rpl29 | 806.9978195 | 977.4643216 | 466.0648153 | 0.476810053 | −1.06851344 | 0.001104889 | 0.03059486 |
| Spred3 | 210.5553736 | 116.5734654 | 398.5191899 | 3.418609789 | 1.773409758 | 0.0011111 | 0.030708046 |
| Trpm7 | 590.398978 | 426.8510944 | 917.4947452 | 2.149449204 | 1.103967017 | 0.001113671 | 0.030723154 |
| Smarca2 | 2289.935025 | 1920.191888 | 3029.4213 | 1.577665919 | 0.657791738 | 0.001127939 | 0.031060295 |
| Tspan7 | 2176.658952 | 2502.285741 | 1525.405374 | 0.60960479 | −0.714053856 | 0.001138541 | 0.031238854 |
| Usp34 | 3289.756093 | 2813.701501 | 4241.865276 | 1.507574728 | 0.592229516 | 0.00113656 | 0.031238854 |
| Gm561 | 224.1385166 | 300.1834413 | 72.04866711 | 0.240015461 | −2.058800751 | 0.001146883 | 0.031410943 |
| Ift52 | 384.1849683 | 492.9711812 | 166.6125427 | 0.337976233 | −1.565006298 | 0.00115777 | 0.031595054 |
| Mgat4b | 103.8348367 | 148.4348122 | 14.63488551 | 0.098594698 | −3.342346121 | 0.001155947 | 0.031595054 |
| Phip | 2403.192998 | 2020.844563 | 3167.889832 | 1.567606861 | 0.648563793 | 0.001162033 | 0.03165444 |
| Hn1l | 1455.556295 | 1703.760502 | 959.1478808 | 0.562959336 | −0.828897379 | 0.001168744 | 0.031729216 |
| Rsrc2 | 1469.670975 | 1192.447841 | 2024.117242 | 1.697447194 | 0.763366694 | 0.00116896 | 0.031729216 |
| Mrpl51 | 286.8565473 | 375.6854403 | 109.1987611 | 0.290665406 | −1.782568717 | 0.001175368 | 0.031846167 |
| Gpx3 | 827.2588918 | 630.7261882 | 1220.324299 | 1.934792501 | 0.952178851 | 0.001188227 | 0.032080015 |
| Nop10 | 581.1241079 | 719.1456244 | 305.0810748 | 0.424227117 | −1.237091253 | 0.001186629 | 0.032080015 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Eef2 | 7586.148988 | 8423.53949 | 5911.367984 | 0.701767706 | −0.510934536 | 0.001202423 | 0.032405609 |
| Chd9 | 3161.922 | 2702.442233 | 4080.881535 | 1.510071699 | 0.594617051 | 0.001216801 | 0.032447306 |
| Dennd2d | 293.7170253 | 182.2135207 | 516.7240344 | 2.835816092 | 1.503763974 | 0.001214369 | 0.032447306 |
| Eno3 | 121.6242442 | 52.97391764 | 258.9248974 | 4.887780797 | 2.289179586 | 0.001216493 | 0.032447306 |
| Sfswap | 335.3083834 | 215.8936671 | 574.137816 | 2.659354597 | 1.411076158 | 0.001210717 | 0.032447306 |
| Snx32 | 198.5067643 | 108.6323953 | 378.2555023 | 3.481977003 | 1.799906675 | 0.001207447 | 0.032447306 |
| Tmem14c | 278.6988069 | 365.7003507 | 104.6957194 | 0.286288266 | −1.804459553 | 0.001213963 | 0.032447306 |
| Chdh | 24.65158169 | 0.953038975 | 72.04086711 | 75.59886739 | 6.240292715 | 0.001241935 | 0.033059441 |
| Ndufb10 | 601.8131553 | 742.8617529 | 319.7159603 | 0.430384199 | −1.216302984 | 0.001246519 | 0.033123357 |
| Polr3a | 462.1414089 | 319.4596528 | 747.5049212 | 2.339904006 | 1.226449345 | 0.001252734 | 0.033230315 |
| Fam135b | 612.4502668 | 446.9817827 | 943.3872349 | 2.110572 | 1.077634046 | 0.001277371 | 0.033824692 |
| Fam193b | 286.8389689 | 178.0881185 | 504.3406697 | 2.831972587 | 1.5018073 | 0.001286606 | 0.033971282 |
| Nenf | 402.6908311 | 512.2867721 | 183.498949 | 0.358195759 | −1.48117984 | 0.001287385 | 0.033971282 |
| Rnaseh2a | 74.13317115 | 108.3853557 | 5.628802118 | 0.051933235 | −4.267198101 | 0.001310536 | 0.034462324 |
| Vps35 | 2635.83217 | 3004.169338 | 1899.157834 | 0.632174029 | −0.661606327 | 0.001308706 | 0.034462324 |
| LOC626693 | 30.06402313 | 2.317138604 | 85.55779219 | 36.92389918 | 5.206483005 | 0.001323688 | 0.034696897 |
| Mtch1 | 1311.408201 | 1557.898388 | 818.4278279 | 0.525340956 | −0.928674033 | 0.001325731 | 0.034696897 |
| Tmtc3 | 2131.232339 | 1784.019177 | 2825.658663 | 1.58387236 | 0.663456077 | 0.001326316 | 0.034696897 |
| Ngfrap1 | 3107.619285 | 3521.596499 | 2279.664858 | 0.647338461 | −0.627407872 | 0.001333375 | 0.0348215 |
| Trim46 | 253.6908789 | 152.0069524 | 457.058732 | 3.006827811 | 1.588242253 | 0.001374555 | 0.035835275 |
| Lrrc27 | 243.4702152 | 143.9933996 | 442.4238464 | 3.072528656 | 1.619426466 | 0.001380863 | 0.035937978 |
| Mir344c | 24.2472354 | 0.909399752 | 70.92290668 | 77.98870243 | 6.285193243 | 0.001400975 | 0.03639895 |
| Chd8 | 1166.661756 | 929.3132859 | 1641.358698 | 1.766205996 | 0.820653617 | 0.001404461 | 0.036427145 |
| Eef1g | 913.5236553 | 1094.474179 | 551.6226963 | 0.504069526 | −0.988484429 | 0.001407257 | 0.036437394 |
| Pard6b | 158.7677526 | 218.4508214 | 39.40161482 | 0.180368353 | −2.470981868 | 0.001414164 | 0.036531508 |
| Unc50 | 1010.872604 | 1203.910388 | 624.7970351 | 0.518973041 | −0.946268498 | 0.001415707 | 0.036531508 |
| Atp5g3 | 1559.828839 | 1859.606438 | 960.2736413 | 0.516385414 | −0.953479843 | 0.001441708 | 0.037046485 |
| Ids | 11227.51458 | 9903.773266 | 13874.99922 | 1.400980904 | 0.486437291 | 0.001442989 | 0.037046485 |
| Rimbp2 | 1171.893947 | 933.7842899 | 1648.11326 | 1.764982853 | 0.819654168 | 0.001439192 | 0.037046485 |
| Odf2 | 706.4916651 | 530.0672184 | 1059.340559 | 1.998502306 | 0.998919238 | 0.001448095 | 0.037114767 |
| Svil | 769.9844281 | 566.2039406 | 1177.545403 | 2.079719547 | 1.056388992 | 0.001479557 | 0.0378572 |
| Jmjd1c | 2977.502157 | 2545.705953 | 3841.094565 | 1.508653411 | 0.593451695 | 0.001485792 | 0.037952743 |
| Samm50 | 495.3736683 | 618.6639757 | 248.7930536 | 0.402145694 | −1.314209824 | 0.001502712 | 0.038320421 |
| Fam126b | 864.6066949 | 666.4842052 | 1260.851674 | 1.891795281 | 0.919755977 | 0.001519757 | 0.038690066 |
| Ext2 | 1701.16078 | 1404.591299 | 2294.299743 | 1.633428702 | 0.707903484 | 0.001526657 | 0.038800624 |
| Idh3a | 443.6596706 | 558.5422657 | 213.8944805 | 0.382951289 | −1.384767201 | 0.001536353 | 0.038975129 |
| Luc7l | 671.11157 | 499.5122842 | 1014.301142 | 2.030600996 | 1.021906784 | 0.001539187 | 0.038975129 |
| Vamp8 | 677.6090253 | 826.7229066 | 379.3812627 | 0.458897727 | −1.123755434 | 0.00154123 | 0.038975129 |
| Lrrc45 | 116.2105792 | 50.48222215 | 247.6672932 | 4.906029938 | 2.294556038 | 0.00154585 | 0.039026925 |
| Fyco1 | 1147.410893 | 915.0718764 | 1612.088926 | 1.761707433 | 0.816974356 | 0.001551281 | 0.039080843 |
| Hspe1 | 564.5596161 | 697.676163 | 298.3256522 | 0.427600262 | −1.225665358 | 0.001553137 | 0.039080843 |
| Atn1 | 998.8781013 | 784.5850434 | 1427.464217 | 1.819387495 | 0.863452843 | 0.001563207 | 0.0392691 |
| Lsmd1 | 181.4157619 | 246.2311531 | 51.78497948 | 0.210310429 | −2.249407701 | 0.001576995 | 0.039549983 |
| Herpud1 | 2303.723151 | 2633.216737 | 1644.735979 | 0.624610939 | −0.678970259 | 0.001587192 | 0.039674569 |
| Tpi1 | 662.8254121 | 817.4937316 | 353.488773 | 0.432405484 | −1.209543273 | 0.001586422 | 0.039674569 |
| Trim39 | 425.0291134 | 293.0609805 | 688.9653792 | 2.35092839 | 1.233230595 | 0.001594373 | 0.039788522 |
| Carhsp1 | 326.492525 | 421.0674017 | 137.3427717 | 0.326177641 | −1.616270205 | 0.001606091 | 0.040015129 |
| Chchd10 | 1104.786266 | 1306.505027 | 701.3487439 | 0.536812893 | −0.897508772 | 0.00162463 | 0.040362195 |
| Rock1 | 1863.231807 | 1549.756682 | 2490.182057 | 1.606821307 | 0.684209497 | 0.001625341 | 0.040362195 |
| BC005764 | 202.3457299 | 90.74987483 | 425.5374401 | 4.689124265 | 2.229318512 | 0.001630711 | 0.040379748 |
| Ccnd2 | 10390.013 | 11455.16739 | 8259.704227 | 0.72104614 | −0.471836515 | 0.001631371 | 0.040379748 |
| Smek2 | 1360.989577 | 1102.037292 | 1878.894147 | 1.704927919 | 0.769710746 | 0.001646505 | 0.04065768 |
| Zfp706 | 790.4602164 | 969.5443233 | 432.2920026 | 0.445871315 | −1.165300707 | 0.001647958 | 0.04065768 |
| Sec63 | 2767.114371 | 2359.586722 | 3582.169668 | 1.518134356 | 0.602299476 | 0.001654953 | 0.040763976 |
| Snap23 | 1201.307606 | 962.7070131 | 1678.508791 | 1.743530242 | 0.802011388 | 0.001688332 | 0.041518744 |
| 0610011F06Rik | 559.4268035 | 691.1027095 | 296.0749914 | 0.428409536 | −1.2229375 | 0.001695439 | 0.041626049 |
| Lmna | 405.1610406 | 512.6148141 | 190.2535116 | 0.371143218 | −1.429952089 | 0.001705643 | 0.041804294 |
| Atp6v1c1 | 1493.012841 | 1737.430113 | 1004.478298 | 0.577967592 | −0.790939496 | 0.001718365 | 0.042052834 |
| Zfp407 | 418.6472512 | 288.554109 | 678.8335354 | 2.352534634 | 1.234215963 | 0.001721622 | 0.042064679 |
| Bcar1 | 550.0477768 | 679.8485705 | 290.4461893 | 0.427221887 | −1.226942535 | 0.001730303 | 0.042073535 |
| Cisd1 | 674.0296119 | 821.3537865 | 379.3812627 | 0.461897503 | −1.114355349 | 0.00172703 | 0.042073535 |
| Nipbl | 2474.650814 | 2098.761534 | 3226.429402 | 1.537301557 | 0.620400192 | 0.001729335 | 0.042073535 |
| Mettl9 | 1050.404815 | 1245.196539 | 660.8213686 | 0.530696439 | −0.914041227 | 0.001734631 | 0.0421113 |
| Cltb | 813.4388791 | 978.6827078 | 482.9512217 | 0.49347068 | −1.018963726 | 0.001767974 | 0.042852185 |
| Cdc42 | 2305.889123 | 2632.525534 | 1652.616302 | 0.627768385 | −0.671695721 | 0.001772629 | 0.042896485 |
| Hivep3 | 513.4139153 | 368.2244017 | 803.7929424 | 2.182888854 | 1.126238675 | 0.001776069 | 0.042911301 |
| Ezh1 | 738.7828394 | 559.9289328 | 1096.490653 | 1.958267538 | 0.969577879 | 0.00177979 | 0.04293283 |
| Araf | 1842.659448 | 1532.970149 | 2462.038046 | 1.606057396 | 0.683523452 | 0.001789203 | 0.043091403 |
| Plekhn1 | 109.3958896 | 46.45187013 | 235.2839285 | 5.065112079 | 2.340594193 | 0.001794346 | 0.043146773 |
| Ndufb3 | 306.075184 | 396.0701922 | 126.2581674 | 0.318340461 | −1.651357562 | 0.001797277 | 0.043148871 |
| Hspa8 | 2514.577212 | 2861.688516 | 1820.354605 | 0.63611207 | −0.652647134 | 0.001804456 | 0.043252782 |
| Dido1 | 1115.78254 | 890.7074356 | 1565.932749 | 1.758077553 | 0.813998713 | 0.001819422 | 0.043542733 |
| Rps17 | 572.1499406 | 704.5586131 | 307.3325956 | 0.43620586 | −1.196918944 | 0.001832148 | 0.043778235 |
| Psmd13 | 337.3323781 | 432.8241396 | 146.3488551 | 0.338125446 | −1.564369505 | 0.00185253 | 0.044195664 |
| Uqcr11 | 324.4188008 | 417.3939352 | 138.4685321 | 0.331745434 | −1.591851487 | 0.001861272 | 0.0443345 |

TABLE 7-continued

Complete list of differentially expressed transcripts in wild-type ALDH⁻ vs. ALDH⁺ cells

| Gene | baseMean all | baseMean ALDH− | baseMean ALDH+ | Fold-Change | log2 Fold-Change | p-value | Adjusted p-value |
|---|---|---|---|---|---|---|---|
| Ift46 | 209.769694 | 280.3188481 | 68.67138584 | 0.244975985 | −2.029287768 | 0.001868454 | 0.044435827 |
| Hadh | 3364.63427 | 3790.602773 | 2512.697265 | 0.662875383 | −0.593190418 | 0.00187335 | 0.044482545 |
| Commd1 | 246.102127 | 324.1227735 | 90.06083388 | 0.277860247 | −1.84756865 | 0.001894176 | 0.044697239 |
| Mtss1l | 1466.189951 | 1201.298311 | 1995.973231 | 1.661513392 | 0.732497921 | 0.00189235 | 0.044697239 |
| Pitpnm2 | 732.7104238 | 551.3831897 | 1095.364892 | 1.986576509 | 0.990284357 | 0.001887363 | 0.044697239 |
| Zfp760 | 272.1681547 | 169.5910223 | 477.3224196 | 2.814550046 | 1.492904301 | 0.001893888 | 0.044697239 |
| 6330407A03Rik | 17.6369133 | 0 | 52.91073991 | Inf | Inf | 0.001909502 | 0.044919193 |
| Cib1 | 138.222341 | 191.5728656 | 31.52129186 | 0.164539439 | −2.603494664 | 0.001907048 | 0.044919193 |
| Sec16b | 455.0268644 | 320.6083204 | 723.8639523 | 2.257782803 | 1.174906707 | 0.001933959 | 0.045424091 |
| Hyou1 | 8555.516144 | 9591.084196 | 6484.38004 | 0.676084153 | −0.564725262 | 0.001959345 | 0.045949212 |
| Hic2 | 125.6225503 | 58.40849655 | 260.0506578 | 4.452274467 | 2.154542532 | 0.001977283 | 0.046291597 |
| Trappc3 | 590.0193263 | 724.0452489 | 321.9674811 | 0.444678674 | −1.169164878 | 0.001980047 | 0.046291597 |
| Tspyl2 | 1340.339019 | 1089.636502 | 1841.744053 | 1.690237111 | 0.757225646 | 0.001990742 | 0.04647005 |
| Tmco1 | 777.8762881 | 937.1593057 | 459.3102528 | 0.490109045 | −1.028825321 | 0.002012185 | 0.046898446 |
| Cenpt | 58.28313094 | 15.37602931 | 144.0973342 | 9.371556942 | 3.22828875 | 0.002021683 | 0.047047546 |
| Atp5g1 | 920.4261292 | 1096.947567 | 567.3832535 | 0.517238262 | −0.951099093 | 0.00203175 | 0.047209409 |
| 0610011L14Rik | 291.1386589 | 377.6055661 | 118.2048445 | 0.313037876 | −1.675590867 | 0.002064051 | 0.047644865 |
| AI450353 | 51.84430667 | 11.90947523 | 131.7139696 | 11.05959474 | 3.467226616 | 0.002066191 | 0.047644865 |
| Gm3414 | 221.2714389 | 130.3960425 | 403.0222316 | 3.090755086 | 1.627959339 | 0.002062854 | 0.047644865 |
| Nfkb1 | 575.1478759 | 390.4653162 | 944.5129953 | 2.418942109 | 1.274376242 | 0.002064607 | 0.047644865 |
| Tm4sf4 | 1992.097086 | 2395.432765 | 1185.425726 | 0.494869129 | −1.014881049 | 0.002057845 | 0.047644865 |
| Tprgl | 559.7711287 | 689.3676765 | 300.5780331 | 0.436019911 | −1.197534077 | 0.00207039 | 0.047669245 |
| Hscb | 164.2187507 | 223.8129176 | 45.03041694 | 0.201196684 | −2.313321564 | 0.002074216 | 0.047684969 |
| 2700038G22Rik | 26.74431568 | 1.840619116 | 76.5517088 | 41.59019545 | 5.37891156 | 0.002081286 | 0.047775112 |
| 1300002E11Rik | 629.4849262 | 469.1564905 | 950.1417975 | 2.025212944 | 1.01807361 | 0.002099617 | 0.048123093 |
| Cfp | 57.09857307 | 14.72495293 | 141.8458134 | 9.633023212 | 3.267988642 | 0.002109852 | 0.048212019 |
| Dhrs7b | 116.7658002 | 163.8910961 | 22.51520847 | 0.137379083 | −2.863765736 | 0.002109282 | 0.048212019 |
| Ccdc47 | 4859.92733 | 5418.31429 | 3743.153408 | 0.690833571 | −0.533589903 | 0.002118424 | 0.04833512 |
| Atp5j | 1260.646689 | 1475.001557 | 831.936953 | 0.564024458 | −0.826170372 | 0.002127738 | 0.048474728 |
| Wapal | 2088.982965 | 1761.735371 | 2743.478152 | 1.557258938 | 0.639008853 | 0.002134971 | 0.04856659 |
| Cltc | 9046.104038 | 9968.411342 | 7201.489429 | 0.722431006 | −0.469068283 | 0.00213941 | 0.04859472 |
| Ahsa1 | 570.5917528 | 701.0955709 | 309.5841165 | 0.441571919 | −1.179279666 | 0.002154408 | 0.048852832 |
| Ndufv3 | 682.7556679 | 828.8140773 | 390.638867 | 0.471322674 | −1.085213009 | 0.002157213 | 0.048852832 |
| Ccdc39 | 17.26165983 | 0 | 51.78497948 | Inf | Inf | 0.002183067 | 0.049364638 |
| Dmtf1 | 418.6072828 | 291.8714378 | 672.0789728 | 2.302654134 | 1.20329773 | 0.002203911 | 0.049761809 |
| Sec61a1 | 4296.264659 | 4801.91253 | 3284.968916 | 0.68409595 | −0.547729405 | 0.002217321 | 0.049990207 |

This table lists a complete set of genes differentially expressed between ALDH⁻ and ALDH⁺ cells, arranged by p-value.

TABLE 8

Curated list of differentially expressed transcripts in wild-type ALDH⁻ vs. ALDH⁺ cells

| Gene | ALDH⁻ | ALDH⁺ | Fold change | Log₂ Fold Change | p-value | Adjusted p-value | Function |
|---|---|---|---|---|---|---|---|
| Aldh1a3 | 43.89 | 1016.56 | 23.16 | 4.53 | 6.71E−24 | 1.13E−20 | Biomarker |
| Ins1 | 2590036.28 | 1940536.28 | 0.75 | −0.42 | 0.000930546 | 0.027522748 | Hormone production |
| Gcg | 8148.96 | 3014.79 | 0.37 | −1.43 | 5.72E−05 | 0.00332584 | |
| Ppy | 2650.81 | 496.46 | 0.19 | −2.42 | 1.23E−21 | 1.55E−18 | |
| Pyy | 5362.39 | 860.08 | 0.16 | −2.64 | 3.61E−37 | 1.10E−33 | |
| Gipr | 158.22 | 527.98 | 3.34 | 1.74 | 0.000249629 | 0.010434218 | |
| Malat1 | 28383.66 | 317323.72 | 11.18 | 3.48 | 3.39E−60 | 5.14E−56 | LncRNA |
| Meg3 | 1394.28 | 14866.79 | 10.66 | 3.41 | 3.32E−52 | 2.52E−48 | |
| Neat1 | 1293.07 | 8685.24 | 6.72 | 2.75 | 1.34E−30 | 2.91E−27 | |
| Peg3 | 10847.19 | 26432.85 | 2.44 | 1.29 | 6.41E−22 | 9.35E−19 | |
| Snhg11 | 142.49 | 2397.86 | 16.82 | 4.07 | 4.52E−43 | 1.71E−39 | |
| Kcnq1ot1 | 775.61 | 5750.38 | 7.41 | 2.89 | 1.90E−30 | 3.61E−27 | |
| Bach2 | 16.18 | 238.66 | 14.75 | 3.88 | 5.61E−06 | 0.000512996 | Cellular differentiation |
| Mlxipl | 1521.05 | 6819.86 | 4.48 | 2.16 | 1.35E−33 | 3.42E−30 | |
| Hic2 | 58.41 | 260.05 | 4.45 | 2.15 | 0.001977283 | 0.046291597 | |
| Ncor1 | 3821.50 | 6625.10 | 1.73 | 0.79 | 1.41E−06 | 0.000162812 | |
| Pax6 | 2560.43 | 4087.64 | 1.60 | 0.67 | 0.000270125 | 0.010988238 | |
| Rfx6 | 1409.36 | 2881.95 | 2.04 | 1.03 | 1.46E−06 | 0.000166394 | |
| Rfx7 | 916.06 | 1825.98 | 1.99 | 1.00 | 8.29E−05 | 0.004444825 | |
| Sall1 | 94.36 | 0.00 | 0.00 | INF | 8.19E−05 | 0.004414367 | |
| Atp1a1 | 9889.83 | 6215.32 | 0.63 | −0.67 | 1.55E−05 | 0.001206084 | Complex V |

TABLE 8-continued

Curated list of differentially expressed transcripts in wild-type ALDH⁻ vs. ALDH⁺ cells

| Gene | ALDH⁻ | ALDH⁺ | Fold change | Log$_2$ Fold Change | p-value | Adjusted p-value | Function |
|---|---|---|---|---|---|---|---|
| Atp1b3 | 1251.14 | 575.26 | 0.46 | −1.12 | 0.000162268 | 0.007646262 | |
| Atp5a1 | 6810.79 | 3792.69 | 0.56 | −0.84 | 0.000857639 | 0.025870698 | |
| Atp5c1 | 2636.63 | 1433.09 | 0.54 | −0.88 | 0.000205123 | 0.009162496 | |
| Atp5e | 1589.03 | 326.47 | 0.21 | −2.28 | 4.43E−14 | 3.05E−11 | |
| Atp5g1 | 1096.95 | 567.38 | 0.52 | −0.95 | 0.00203175 | 0.047209409 | |
| Atp5g3 | 1859.61 | 960.27 | 0.52 | −0.95 | 0.001441708 | 0.037046485 | |
| Atp5j | 1475.00 | 831.94 | 0.56 | −0.83 | 0.002127738 | 0.048474728 | |
| Atp5o | 865.54 | 342.23 | 0.40 | −1.34 | 0.000171152 | 0.007869345 | |
| Atp6v0d1 | 2455.93 | 1463.49 | 0.60 | −0.75 | 0.00077602 | 0.024052844 | |
| Atp6v0e | 1202.47 | 538.11 | 0.45 | −1.16 | 0.000130094 | 0.006429695 | |
| Atp6v1b2 | 3943.01 | 2468.79 | 0.63 | −0.68 | 0.000378227 | 0.014275718 | |
| Atp6v1c1 | 1737.43 | 1004.18 | 0.58 | −0.79 | 0.001718365 | 0.042052834 | |
| Atp6v1e1 | 1431.67 | 598.90 | 0.42 | −1.26 | 1.06E−05 | 0.000867355 | |
| Atp6v1f | 634.28 | 162.11 | 0.26 | −1.97 | 0.000947641 | 0.027859186 | |
| Cox17 | 750.09 | 184.62 | 0.25 | −2.02 | 6.45E−07 | 8.30E−05 | Complex IV |
| Cox4i1 | 1686.10 | 526.86 | 0.31 | −1.68 | 1.82E−09 | 4.67E−07 | |
| Cox6a1 | 1830.11 | 875.84 | 0.48 | −1.06 | 2.98E−05 | 0.001962504 | |
| Cox6b1 | 1089.61 | 258.92 | 0.24 | −2.07 | 6.69E−05 | 0.003759072 | |
| Cox6c | 884.60 | 370.38 | 0.42 | −1.26 | 0.000315848 | 0.012447694 | |
| Cox7a2 | 1190.38 | 303.96 | 0.26 | −1.97 | 1.45E−07 | 2.10E−05 | |
| Cox7b | 1696.32 | 749.76 | 0.44 | −1.18 | 8.68E−06 | 0.000739806 | |
| Cox8a | 1783.45 | 988.42 | 0.55 | −0.85 | 0.000706031 | 0.022364515 | |
| Cyp27b1 | 3.75 | 233.03 | 62.20 | 5.96 | 5.50E−09 | 1.27E−06 | |
| Ndufa11 | 966.85 | 229.66 | 0.24 | −2.07 | 1.31E−08 | 2.62E−06 | Complex I |
| Ndufa13 | 817.24 | 334.35 | 0.41 | −1.29 | 0.00038447 | 0.014368374 | |
| Ndufa2 | 602.15 | 164.36 | 0.27 | −1.87 | 2.40E−05 | 0.001645658 | |
| Ndufa5 | 230.83 | 20.26 | 0.09 | −3.51 | 2.27E−05 | 0.001566944 | |
| Ndufb10 | 742.86 | 319.72 | 0.43 | −1.22 | 0.001246519 | 0.033123357 | |
| Ndufb11 | 944.43 | 369.25 | 0.39 | −1.35 | 8.00E−05 | 0.004381781 | |
| Ndufb2 | 416.34 | 126.09 | 0.30 | −1.72 | 0.000918555 | 0.027274428 | |
| Ndufb3 | 396.07 | 126.09 | 0.32 | −1.65 | 0.001797277 | 0.043148871 | |
| Ndufb8 | 813.88 | 219.52 | 0.27 | −1.89 | 0.000579175 | 0.019313885 | |
| Ndufb9 | 1211.79 | 431.17 | 0.36 | −1.49 | 1.97E−06 | 0.000210659 | |
| Ndufc2 | 1486.70 | 614.67 | 0.41 | −1.27 | 5.86E−06 | 0.000532564 | |
| Ndufs6 | 376.69 | 64.17 | 0.17 | −2.55 | 1.64E−05 | 0.001253071 | |
| Ndufv3 | 828.81 | 390.64 | 0.47 | −1.09 | 0.002157213 | 0.048852832 | |
| Ndor1 | 209.90 | 782.40 | 3.73 | 1.90 | 2.66E−06 | 0.000269397 | |
| Rpl13a | 1619.13 | 636.05 | 0.39 | −1.35 | 9.07E−07 | 0.000111832 | Ribosomal subunits |
| Rpl14 | 1448.69 | 471.69 | 0.33 | −1.62 | 4.09E−08 | 6.95E−06 | |
| Rpl22 | 1352.84 | 681.09 | 0.50 | −0.99 | 0.000488305 | 0.017393076 | |
| Rpl22l1 | 742.74 | 272.43 | 0.37 | −1.45 | 0.000170912 | 0.007869345 | |
| Rpl29 | 977.46 | 466.06 | 0.48 | −1.07 | 0.001104889 | 0.03059486 | |
| Rpl32 | 3663.74 | 1316.01 | 0.36 | −1.48 | 1.61E−12 | 7.87E−10 | |
| Rpl36al | 1651.97 | 891.60 | 0.54 | −0.89 | 0.000614025 | 0.020206063 | |
| Rpl38 | 301.12 | 47.28 | 0.16 | −2.67 | 6.52E−05 | 0.003690809 | |
| Rpl41 | 9232.17 | 3217.42 | 0.35 | −1.52 | 6.15E−09 | 1.37E−06 | |
| Rpl8 | 3049.55 | 1108.87 | 0.36 | −1.46 | 4.04E−11 | 1.57E−08 | |
| Rplp0 | 1081.18 | 529.11 | 0.49 | −1.03 | 0.000975463 | 0.028353845 | |
| Rplp1 | 2091.32 | 552.75 | 0.26 | −1.92 | 2.97E−13 | 1.73E−10 | |
| Rps11 | 1754.68 | 761.01 | 0.43 | −1.21 | 4.37E−06 | 0.000416959 | |
| Rps14 | 1438.54 | 333.23 | 0.23 | −2.11 | 3.75E−05 | 0.002361914 | |
| Rps15 | 2313.78 | 865.71 | 0.37 | −1.42 | 4.51E−09 | 1.07E−06 | |
| Rps15a | 1076.58 | 395.14 | 0.37 | −1.45 | 9.87E−06 | 0.000831648 | |
| Rps17 | 704.56 | 307.33 | 0.44 | −1.20 | 0.001832148 | 0.043778235 | |
| Rps20 | 1126.82 | 388.39 | 0.34 | −1.54 | 2.17E−06 | 0.000225538 | |
| Rps21 | 1023.31 | 452.56 | 0.44 | −1.18 | 0.000289137 | 0.011636817 | |
| Rps24 | 1994.06 | 717.11 | 0.36 | −1.48 | 9.24E−09 | 1.95E−06 | |
| Rps25 | 1320.93 | 670.95 | 0.51 | −0.98 | 0.000635685 | 0.020609513 | |
| Rps27l | 936.36 | 274.69 | 0.29 | −1.77 | 8.32E−07 | 0.000104333 | |
| Rps28 | 447.27 | 119.33 | 0.27 | −1.91 | 0.000196341 | 0.008813862 | |
| Rps3 | 3520.68 | 1400.45 | 0.40 | −1.33 | 2.01E−10 | 6.61E−08 | |
| Rps5 | 4075.84 | 1368.92 | 0.34 | −1.57 | 1.36E−14 | 9.85E−12 | |
| Rps6kb2 | 137.19 | 466.06 | 3.40 | 1.76 | 0.000448689 | 0.016209421 | |
| Rps9 | 1981.66 | 722.74 | 0.36 | −1.46 | 1.44E−08 | 2.84E−06 | |

This table lists a subset of genes differentially expressed between ALDH⁻ and ALDH⁺ cells, arranged by functional category

TABLE 9

Ingenuity analyses of differentially activated or suppressed functional networks in
ALDH⁻ vs. ALDH⁺ cells isolated from wild-type mice

| | Wild-type ALDH+ | Foxo KO ALDH+ |
|---|---|---|
| Transcription Factor ACTIVATION | | |
| CREB1 | z = 2.020, p = 5.66E−03 | |
| CTNNB1 | | z = 2.028, p = 4.66E−02 |
| GLI1 | z = 2.779, p = 1.00E00 | |
| IRF4 | | z = 2.236, p = 2.23E−01 |
| MITF | | z = 2.000, p = 4.72E−01 |
| MYOCD | z = 2.200, p = 9.37E−02 | |
| NEUROG3 | z = 0.479, p = 3.72E−02 | |
| NFKB1 | z = 2.178, p = 3.70E−01 | z = 2.219, p = 4.03E−01 |
| STAT1 | | z = 2.207, p = 1.00E−00 |
| STAT3 | z = 1.817, p = 1.00E00 | |
| STAT4 | z = 2.006, p = 1.46E−02 | |
| SPIB | z = 2.000, p = 4.92E−01 | |
| WT1 | z = 1.967, p = 2.61E−01 | |
| XBP1 | z = 0.204, p = 1.58E−02 | |
| Transcription Factor INHIBITION | | |
| ATF4 | z = −1.772, p = 1.59E−01 | |
| Esrra | z = −3.148, p = 6.84E−04 | |
| NFE2L2 | z = −2.778, p = 2.68E−04 | |
| NRF1 | z = −2.345, p = 3.43E−05 | |
| MYC | z = −1.777, p = 2.62E−03 | |
| MYCN | z = −4.932, p = 1.78E−09 | |
| RBPJ | z = −1.622, p = 2.56E−02 | |
| TP53 | z = −2.428, p = 1.88E−02 | z = −2.008, p = 7.59E−02 |
| Other ACTIVATION | | |
| RICTOR | z = 8.699, p = 2.47E−48 | z = 4.359 p = 5.93E−06 |
| CD24 | z = 3.308, p = 5.91E−04 | |
| TSC2 | z = 2.000, p = 2.90E−02 | |
| INS | z = 2.499, p = 4.12E−03 | z = 2.618 p = 1.67E−02 |
| MYD88 | z = 2.359, p = 1.00E00 | z = 1.961 p = 0.00E−00 |
| TICAM1 | z = 2.155, p = 2.55E−01 | |
| IFRD1 | z = 2.219, p = 8.97E−03 | |
| CUL4B | z = 2.236, p = 1.92E−02 | |
| HIST1H1T | | z = 2.000, p = 1.38E−01 |
| Other INHIBITION | | |
| SOCS1 | | z = −1.969 p = 1.51E−01 |
| HIST1H1T | z = 0.632 p = 4.19E−03 | z = 2.000 p = 1.38E−01 |
| Biological and chemical drug (random cut) | | |
| CD437 | z = 4.562, p = 7.15E−13 | z = 2.496 p = 9.66E−04 |
| sirolimus | z = 3.748, p = 4.48E−11 | |
| 5-fluorouracil | z = 3.115, p = 3.14E−09 | |
| Biological and chemical drug (random cut) | | |
| mono-2-ethyl-phthlate | z = −2.626, p = 1.98E−07 | z = −2.138 p = 9.33E−03 |
| 2-amino-1-methyl-6 phenylimidazo(4,5-b)pyridine | z = −3.000, p = 9.83E−05 | |
| 1,2-dithiol-3-thione | z = −3.393, p = 3.17E−04 | |
| curcumin | | z = −2.143 p = 5.42E−01 |
| Nuclear receptor (NR) ACTIVATION | | |
| ESR2 (NR) | z = 2.613, p = 1.00E00 | |
| NR5A2 (NR) | z = 2.433, p = 1.66E−01 | |
| AR (NR) | z = 2.260, p = 3.50E−01 | |
| TLR7 (TM) | z = 2.219, p = 5.35E−01 | |
| ADORA2A (GPCR) | | z = 0.412 p = 1.03E−03 |
| Transmembrane receptor (TM), GPCR, Nuclear receptor (NR) INHIBITION | | |
| IGF1R (TM) | z = −2.399, p = 2.23E−06 | z = −2.496 p = 1.43E−03 |
| NR4A3 (NR) | z = −2.213, p = 2.50E−02 | |
| Enzyme (EZ), Kinase (KN), Peptidase (PD), Phosphatase (PPT), ACTIVATION | | |
| PSEN1 (PD) | z = 2.064, p = 5.05E−06 | |
| SRC (KN) | z = 2.131, p = 2.43E−01 | |
| PTGS2 (EZ) | z = 2.737, p = 1.02E−01 | |
| NOS2 (EZ) | z = 2.180, p = −1.00E00 | |
| SURF1 (EZ) | z = 2.000, p = 2.10E−02 | |
| EGFR (KN) | z = 1.971, p = 2.42E−01 | z = 2.076, p = 3.21E−01 |
| MET (KN) | | z = 2.153, p = 3.44E−02 |

TABLE 9-continued

Ingenuity analyses of differentially activated or suppressed functional networks in ALDH⁻ vs. ALDH⁺ cells isolated from wild-type mice

| | Wild-type ALDH+ | Foxo KO ALDH+ |
|---|---|---|
| F2 (PD) | | z = 2.205, p = 2.17E−01 |
| Enzyme (EZ), Kinase (KN), Peptidase (PD), Phosphatase (PPT) INHIBITION | | |
| PRKAA1 (KN) | z = −2.236, p = 3.47E−01 | |
| SOCS3 (PPT) | z = −2.236, p = 2.29E−01 | |
| INSR (KN) | z = −3.637, p = 5.01E−04 | |
| EIF2AK4 (KN) | z = −2.630, p = 4.28E−04 | |
| Growth factor ACTIVATION | | |
| HGF | z = 3.30, p = 4.71E−01 | |
| EGF | z = 2.090, p = 1.00E00 | z = 2.186, p = 1.00E00 |
| AGT | | z = 2.014, p = 1.85E−01 |
| Cytokine ACTIVATION | | |
| CXCL12 | z = 2.773, p = 5.03E−01 | |
| EDN1 | z = 2.239, p = 1.31E−01 | |
| IL6 | z = 2.310, p = 1.00E00 | |
| OSM | z = 2.294, p = 1.00E00 | |
| LIF | | z = 2.364, p = 8.55E−02 |
| WNT3A | | z = 2.342, p = 2.342E−01 |

A partial list of different Ingenuity Pathway analyses to identify trends in gene expression in the different islet cell types.

TABLE 10

List of differentially expressed transcripts in ALDH⁺ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Foxo1 | 349.7794248 | 1005.012999 | 131.3682334 | 0.130712969 | −2.935525802 | 2.23E−11 | 3.47E−07 |
| Cyb5r3 | 2576.053292 | 5076.014959 | 1742.732737 | 0.343326951 | −1.542344984 | 8.29E−09 | 6.46E−05 |
| Cyp27b1 | 55.32317138 | 206.7969094 | 4.831925389 | 0.023365559 | −5.419472636 | 5.10E−07 | 0.002649712 |
| Elovl7 | 124.8599548 | 384.622271 | 38.27251604 | 0.09950676 | −3.32906165 | 1.46E−06 | 0.005684329 |
| Hip1r | 716.4685825 | 1463.562668 | 467.4372208 | 0.319383127 | −1.646639999 | 2.98E−06 | 0.009288892 |
| Bach2 | 61.74301035 | 211.7920038 | 11.7266792 | 0.055368848 | −4.174781692 | 2.45E−05 | 0.052959279 |
| Ptprt | 324.3808944 | 753.2602399 | 181.4211126 | 0.240847854 | −2.053806023 | 2.71E−05 | 0.052959279 |
| Etl4 | 836.462433 | 1573.454745 | 590.7983289 | 0.375478437 | −1.413198035 | 3.21E−05 | 0.052959279 |
| Muc4 | 1555.856509 | 3932.138334 | 763.7625667 | 0.194235935 | −2.364117959 | 3.32E−05 | 0.052959279 |
| Ctsl | 4496.474551 | 2272.767965 | 5237.71008 | 2.304551173 | 1.204485803 | 3.39E−05 | 0.052959279 |
| Dnahc17 | 29.21450191 | 112.8891341 | 1.322957853 | 0.011719089 | −6.414995718 | 3.87E−05 | 0.054903167 |
| Spp1 | 2405.635018 | 3933.137353 | 1896.467572 | 0.482176797 | −1.052365866 | 0.000104638 | 0.136037989 |
| Gpc6 | 18.23209467 | 72.92837866 | 0 | 0 | #NAME? | 0.000119737 | 0.14369393 |
| Cxcl13 | 17.98233994 | 71.92935978 | 0 | 0 | #NAME? | 0.000135081 | 0.150528447 |
| Prnd | 24.27000451 | 93.90777526 | 1.057414255 | 0.011260135 | −6.472632027 | 0.000149671 | 0.155667934 |
| Ncam1 | 1479.626588 | 2471.572723 | 1148.977876 | 0.464877228 | −1.105078338 | 0.000183578 | 0.173360099 |
| 2010015L04Rik | 87.00878742 | 249.7547214 | 32.76014275 | 0.131169263 | −2.930498403 | 0.000188906 | 0.173360099 |
| Jam2 | 182.4268457 | 437.570272 | 97.37903698 | 0.22254491 | −2.167831588 | 0.000207049 | 0.179454216 |
| Galntl4 | 119.5275192 | 316.6889868 | 53.80702993 | 0.169904961 | −2.557200117 | 0.000328609 | 0.269822705 |
| Nog | 15.48479273 | 61.93917092 | 0 | 0 | #NAME? | 0.000451442 | 0.351638321 |
| D0H4S114 | 296.5293792 | 613.3975959 | 190.9066403 | 0.311228217 | −1.683955227 | 0.000492415 | 0.351638321 |
| Hcn1 | 19.67871965 | 76.92445421 | 0.596808134 | 0.007758367 | −7.010031294 | 0.000495868 | 0.351638321 |
| Cox6b1 | 579.2995025 | 229.7743437 | 695.8078888 | 3.028222723 | 1.598471318 | 0.000553818 | 0.362501015 |
| Krba1 | 187.7400796 | 424.5830265 | 108.7924307 | 0.256233584 | −1.964468514 | 0.000565259 | 0.362501015 |
| Zfp618 | 95.90087591 | 259.7449103 | 41.28619777 | 0.158949015 | −2.653364014 | 0.000580894 | 0.362501015 |
| Pygo1 | 28.58340272 | 104.896983 | 3.145542627 | 0.029986969 | −5.059520461 | 0.000612413 | 0.367471323 |
| Anpep | 1218.657663 | 1993.042677 | 960.5293244 | 0.481941172 | −1.053071039 | 0.000641507 | 0.370672475 |
| Arhgef6 | 37.83659814 | 130.871474 | 6.824972837 | 0.052150195 | −4.261183554 | 0.000673245 | 0.375117954 |
| D330022K07Rik | 201.7932795 | 449.5584986 | 119.2048731 | 0.26515987 | −1.915065643 | 0.000707598 | 0.380663317 |
| Eml5 | 4561.421402 | 6798.323518 | 3815.787363 | 0.56128358 | −0.83319824 | 0.000836787 | 0.404802152 |
| 5730508B09Rik | 59.66791457 | 180.8224183 | 19.28307998 | 0.10664098 | −3.229166145 | 0.000839858 | 0.404802152 |
| Lair1 | 26.73296816 | 97.90385081 | 3.009340615 | 0.030737715 | −5.023846292 | 0.000840268 | 0.404802152 |
| Gpr98 | 418.6612241 | 780.2337498 | 298.1370488 | 0.382112474 | −1.387930738 | 0.00087865 | 0.404802152 |
| Slc2a4rg-ps | 109.1071855 | 278.7262691 | 52.56749097 | 0.188598983 | −2.406606196 | 0.000882205 | 0.404802152 |
| Cd44 | 839.3634842 | 1552.475349 | 601.6595295 | 0.387548524 | −1.367551138 | 0.000984629 | 0.438891384 |
| Tspan2 | 697.327608 | 1209.811871 | 526.4995204 | 0.435191234 | −1.200278599 | 0.001036288 | 0.449086763 |
| Abcc10 | 216.7436511 | 460.5477064 | 135.4756327 | 0.294161996 | −1.765317222 | 0.001092283 | 0.460559503 |
| Rfx6 | 1632.655799 | 2557.488348 | 1324.378282 | 0.51784333 | −0.949412409 | 0.001140404 | 0.46767398 |
| Ckb | 1406.377612 | 743.270051 | 1627.413466 | 2.189531872 | 1.13062245 | 0.00116911 | 0.46767398 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Dtx4 | 18.65374909 | 71.92935978 | 0.895212201 | 0.012445713 | −6.328207254 | 0.001389083 | 0.541776915 |
| Fat1 | 769.095564 | 1287.735344 | 596.2156374 | 0.462995475 | −1.110930001 | 0.001469204 | 0.55904989 |
| Hapln4 | 886.6905817 | 1460.565611 | 695.3989052 | 0.47611617 | −1.070614467 | 0.001546453 | 0.560290004 |
| Uchl1 | 54.26867086 | 161.8410595 | 18.41120798 | 0.113761045 | −3.135921478 | 0.00156609 | 0.560290004 |
| Park7 | 683.5129877 | 315.6899679 | 806.120661 | 2.553520045 | 1.352487384 | 0.001638868 | 0.560290004 |
| Szt2 | 354.4530757 | 666.3455968 | 250.488902 | 0.375914395 | −1.411523932 | 0.001650792 | 0.560290004 |
| Nnt | 632.9867799 | 285.7194013 | 748.7425727 | 2.620552084 | 1.389870783 | 0.001652031 | 0.560290004 |
| Rsph4a | 105.4461812 | 260.7439292 | 53.68026525 | 0.2058735 | −2.280169958 | 0.001811435 | 0.586371216 |
| Insrr | 2490.680039 | 3749.317878 | 2071.134093 | 0.552402906 | −0.856207185 | 0.001840231 | 0.586371216 |
| Adora3 | 701.0062234 | 328.6772134 | 825.1158934 | 2.510414047 | 1.32792533 | 0.001841689 | 0.586371216 |
| Spnb3 | 409.8191874 | 745.2680888 | 298.0028869 | 0.399859985 | −1.32243318 | 0.002037133 | 0.617919778 |
| BC021891 | 122.4157883 | 291.7135147 | 65.98321278 | 0.226191827 | −2.144381295 | 0.002050793 | 0.617919778 |
| Manscl | 159.7771067 | 357.6487611 | 93.81988857 | 0.262324098 | −1.930577752 | 0.002059601 | 0.617919778 |
| Cenpt | 40.15175484 | 127.8744174 | 10.91086732 | 0.085324864 | −3.550889973 | 0.002145816 | 0.624257214 |
| Dock5 | 818.1777035 | 1343.680401 | 643.0101375 | 0.478543958 | −1.063276641 | 0.002160752 | 0.624257214 |
| Reln | 183.3020628 | 392.6144221 | 113.5312764 | 0.289167915 | −1.790023373 | 0.002232299 | 0.633201798 |
| Zc3hav11 | 404.6971005 | 733.2798622 | 295.1695133 | 0.402533233 | −1.3128202 | 0.002353068 | 0.655063124 |
| Cdc14a | 37.8092999 | 121.8803041 | 9.78563184 | 0.08028887 | −3.638656188 | 0.002393346 | 0.655063124 |
| Hscb | 174.7209022 | 39.96075543 | 219.6409512 | 5.496416391 | 2.458491302 | 0.002469258 | 0.664187958 |
| Mgat4b | 102.9269687 | 12.98724552 | 132.9068765 | 10.23364626 | 3.355248365 | 0.002741143 | 0.674279216 |
| Zcchc12 | 103.516591 | 253.750797 | 53.43852234 | 0.2105945 | −2.247460333 | 0.00275132 | 0.674279216 |
| Rnf150 | 441.1221262 | 1061.957076 | 234.1771431 | 0.220514697 | −2.18105328 | 0.00275409 | 0.674279216 |
| Senp7 | 553.1422547 | 946.0708848 | 422.1660446 | 0.446230881 | −1.164137737 | 0.00275645 | 0.674279216 |
| Zfp9 | 1258.235545 | 1947.087808 | 1028.618124 | 0.528285463 | −0.920610468 | 0.002778284 | 0.674279216 |
| Acp1 | 99.30841826 | 241.7625704 | 51.8237009 | 0.214357834 | −2.221906952 | 0.002798093 | 0.674279216 |
| Pik3c2b | 51.65012096 | 153.8489084 | 17.58385848 | 0.114293034 | −3.129190622 | 0.002916368 | 0.674279216 |
| Gabarap | 2085.90723 | 1232.789305 | 2370.279871 | 1.922696653 | 0.943131165 | 0.002949357 | 0.674279216 |
| Map3k14 | 114.3877259 | 269.7350992 | 62.60526811 | 0.232099079 | −2.107187297 | 0.003014706 | 0.674279216 |
| Gm7694 | 30.29055789 | 102.8989452 | 6.087762111 | 0.059162532 | −4.079172399 | 0.003016649 | 0.674279216 |
| Shfm1 | 184.1675899 | 46.95388763 | 229.9054907 | 4.896410123 | 2.291724403 | 0.003036205 | 0.674279216 |
| 0610011L14Rik | 300.2149029 | 104.896983 | 365.3208762 | 3.482663331 | 1.800191014 | 0.003043961 | 0.674279216 |
| Syp | 3752.589483 | 5394.701983 | 3205.21865 | 0.59414193 | −0.751120487 | 0.003095261 | 0.674279216 |
| Asb4 | 52.43751126 | 153.8489084 | 18.63371221 | 0.121116961 | −3.045527186 | 0.003179074 | 0.674279216 |
| Rcbtb2 | 247.1144663 | 488.5202352 | 166.6462767 | 0.341124614 | −1.551629237 | 0.003190525 | 0.674279216 |
| Abca8b | 103.2835729 | 249.7547214 | 54.45985672 | 0.218053362 | −2.19724686 | 0.003198299 | 0.674279216 |
| Sema5a | 27.99619274 | 95.90581304 | 5.359652642 | 0.055884544 | −4.161406854 | 0.003271185 | 0.680450126 |
| Ampd3 | 18.65008631 | 69.93132201 | 1.556341079 | 0.022255275 | −5.489708605 | 0.00338768 | 0.690269968 |
| Mical3 | 188.2327279 | 388.6183466 | 121.4375217 | 0.312485303 | −1.678139758 | 0.003406883 | 0.690269968 |
| Odz4 | 476.6943391 | 816.1984297 | 363.5263089 | 0.445389621 | −1.166860157 | 0.003464682 | 0.692980829 |
| Csn3 | 52.78916132 | 153.8489084 | 19.10257895 | 0.12416454 | −3.009674879 | 0.003573554 | 0.705709148 |
| Acsm1 | 20.419877 | 74.92641643 | 2.255103052 | 0.030043216 | −5.056816928 | 0.003634916 | 0.70885403 |
| Gm3086 | 25.42427708 | 87.91366195 | 4.594482123 | 0.052261298 | −4.258113221 | 0.003720521 | 0.71659077 |
| Fermt1 | 25.17729849 | 87.91366195 | 4.265177338 | 0.048515524 | −4.365409748 | 0.003871923 | 0.727248507 |
| Mapk15 | 176.4894495 | 369.6369877 | 112.1069367 | 0.303289282 | −1.721233578 | 0.003882527 | 0.727248507 |
| Rcn2 | 824.8674612 | 417.5898943 | 960.6266501 | 2.300069456 | 1.201899034 | 0.003915702 | 0.727248507 |
| 9130014G24Rik | 147.2601177 | 317.6880057 | 90.45082167 | 0.284715885 | −1.812405108 | 0.003965223 | 0.727781765 |
| Acin1 | 768.9366229 | 1229.792248 | 615.318081 | 0.500343112 | −0.999010327 | 0.004137312 | 0.749799363 |
| Lrrc4 | 181.9183183 | 376.6301199 | 117.0143844 | 0.310687803 | −1.686462491 | 0.004181305 | 0.749799363 |
| Ccdc9 | 133.6720912 | 292.7125335 | 80.85610048 | 0.275525547 | −1.859584064 | 0.004240864 | 0.751837723 |
| Pappa2 | 1472.075132 | 3048.006621 | 946.7646354 | 0.310617644 | −1.686788313 | 0.004443404 | 0.778893754 |
| Gpr116 | 106.85621 | 254.7498159 | 57.55834141 | 0.22594066 | −2.145984178 | 0.004499145 | 0.779901746 |
| Kcnh6 | 865.9945329 | 1455.570517 | 669.469205 | 0.459935948 | −1.120495134 | 0.004563555 | 0.782373896 |
| Wscd1 | 35.48836532 | 111.8901152 | 10.02111536 | 0.089562115 | −3.480967593 | 0.004787408 | 0.786649589 |
| Scly | 1152.834569 | 1749.282069 | 954.018736 | 0.545377302 | −0.874673436 | 0.004797405 | 0.786649589 |
| Ifi27l1 | 965.323022 | 528.4809906 | 1110.937032 | 2.102132437 | 1.071853563 | 0.004848354 | 0.786649589 |
| Osbpl6 | 484.7301871 | 825.1895997 | 371.2437163 | 0.449888991 | −1.152359031 | 0.004894949 | 0.786649589 |
| Akap12 | 40.55993293 | 0 | 54.07991057 | Inf | Inf | 0.004985366 | 0.786649589 |
| Zfp41 | 40.63394807 | 124.8773607 | 12.55281052 | 0.100521107 | −3.314429632 | 0.004990415 | 0.786649589 |
| Atox1 | 305.017597 | 116.8852096 | 367.7283929 | 3.146064365 | 1.653548187 | 0.004999643 | 0.786649589 |
| Pkib | 219.5890818 | 434.5732153 | 147.9277039 | 0.340397656 | −1.554706991 | 0.005030792 | 0.786649589 |
| Slurp1 | 10.4896983 | 41.9587932 | 0 | 0 | #NAME? | 0.005042302 | 0.786649589 |
| Slc7a15 | 98.88376209 | 230.7733626 | 54.92056191 | 0.237984841 | −2.071058417 | 0.005158246 | 0.796770209 |
| Adcy9 | 659.3747747 | 1059.959038 | 525.846687 | 0.496100951 | −1.011294371 | 0.005378564 | 0.822656606 |
| Rbm11 | 20.02251907 | 72.92837866 | 2.387232536 | 0.032733931 | −4.933069312 | 0.005433998 | 0.823066024 |
| Rhob | 156.6510851 | 329.6762323 | 98.97603606 | 0.300221934 | −1.735898712 | 0.005527738 | 0.829213818 |
| 3930402G23Rik | 19.04945185 | 69.93132201 | 2.088828469 | 0.029869712 | −5.065172848 | 0.005639765 | 0.837079344 |
| Kctd19 | 10.23994358 | 40.95977432 | 0 | 0 | #NAME? | 0.005687482 | 0.837079344 |
| Syce1 | 12.21202968 | 47.95290652 | 0.298404067 | 0.006222857 | −7.328207254 | 0.005802659 | 0.838903494 |
| Rps19bp1 | 80.55654805 | 8.991169972 | 104.4116741 | 11.6126905 | 3.537630358 | 0.005807421 | 0.838903494 |
| Clip3 | 717.6030719 | 1135.884473 | 578.1759382 | 0.509009456 | −0.974235636 | 0.0059695 | 0.854405229 |
| Mios | 292.2013619 | 537.4721606 | 210.444429 | 0.391544799 | −1.352750711 | 0.006025654 | 0.854602107 |
| Srek1 | 1569.599895 | 2303.737551 | 1324.887343 | 0.575103419 | −0.79810668 | 0.006215742 | 0.861142883 |
| 4931430N09Rik | 92.53208695 | 216.7870982 | 51.11374987 | 0.23577856 | −2.084495558 | 0.006327141 | 0.861142883 |
| Khdrbs2 | 14.77932509 | 55.9450576 | 1.057414255 | 0.018900941 | −5.725398097 | 0.006343136 | 0.861142883 |
| Znf512b | 676.9945567 | 1075.94334 | 544.011629 | 0.50561364 | −0.98389271 | 0.0063632 | 0.861142883 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Nubp1 | 108.9000387 | 249.7547214 | 61.94847775 | 0.248037264 | -2.011371215 | 0.006370092 | 0.861142883 |
| Syt17 | 9.990188858 | 39.96075543 | 0 | 0 | #NAME? | 0.00641488 | 0.861142883 |
| Tnfrsf9 | 170.8533096 | 26.97350992 | 218.8132428 | 8.112153128 | 3.020084885 | 0.006458158 | 0.861142883 |
| Dbpht2 | 645.9488111 | 1044.973755 | 512.9404966 | 0.490864478 | -1.026603327 | 0.006669144 | 0.88174001 |
| Lpcat4 | 234.4182031 | 443.5643853 | 164.7028091 | 0.371316577 | -1.429278372 | 0.006750219 | 0.884959356 |
| Mir665 | 32.38846859 | 100.9009075 | 9.550988961 | 0.094657117 | -3.401145214 | 0.006916038 | 0.896346774 |
| Cldn2 | 43.89976497 | 127.8744174 | 15.90821417 | 0.124404979 | -3.006883871 | 0.007076861 | 0.896346774 |
| Zfp760 | 221.2580919 | 423.5840076 | 153.81612 | 0.36313014 | -1.461441415 | 0.007149886 | 0.896346774 |
| 2310069G16Rik | 11.73664052 | 45.95486875 | 0.330564439 | 0.007193241 | -7.119142374 | 0.007152067 | 0.896346774 |
| BC060267 | 11.71252024 | 45.95486875 | 0.298404067 | 0.006493416 | -7.266806709 | 0.0072036 | 0.896346774 |
| Gm5577 | 79.00028063 | 191.8116261 | 41.39649881 | 0.215818507 | -2.212109508 | 0.007208116 | 0.896346774 |
| Fosl2 | 396.6341474 | 175.8273239 | 470.2364219 | 2.674421765 | 1.419227001 | 0.00723926 | 0.896346774 |
| Pclo | 14878.82559 | 20227.13538 | 13096.05566 | 0.647449844 | -0.627159658 | 0.007401541 | 0.909019303 |
| Golgb1 | 8026.93756 | 10974.22246 | 7044.50926 | 0.641914203 | -0.639547613 | 0.007458142 | 0.909019303 |
| Mll3 | 5224.039285 | 7185.942846 | 4570.071432 | 0.635973808 | -0.652960745 | 0.007897916 | 0.929055999 |
| Sv2b | 225.7544948 | 431.5761587 | 157.1345455 | 0.364094952 | -1.457614781 | 0.007928029 | 0.929055999 |
| Gm15421 | 768.1652633 | 417.5898943 | 885.0237197 | 2.119360961 | 1.083629323 | 0.007988908 | 0.929055999 |
| Fubp3 | 1061.260638 | 615.3956336 | 1209.882306 | 1.966023546 | 0.9752806 | 0.008003981 | 0.929055999 |
| Atf4 | 5748.836747 | 3668.397349 | 6442.316547 | 1.756166504 | 0.812429635 | 0.008029915 | 0.929055999 |
| Peg3 | 16357.60053 | 23456.96344 | 13991.14623 | 0.596460248 | -0.745502104 | 0.008035593 | 0.929055999 |
| Glipr2 | 15.22771244 | 56.94407649 | 1.322257757 | 0.023220286 | -5.428470432 | 0.008039392 | 0.929055999 |
| Pnn | 1589.388383 | 2308.732645 | 1349.606963 | 0.584566154 | -0.774561795 | 0.008102446 | 0.929457757 |
| F8 | 232.2122903 | 435.5722342 | 164.4256423 | 0.377493397 | -1.405476685 | 0.008359615 | 0.951958836 |
| Mllt11 | 607.8142228 | 315.6899679 | 705.1889611 | 2.233892252 | 1.159501476 | 0.008520225 | 0.957282449 |
| Pak6 | 44.03293285 | 0.999018886 | 58.37757083 | 58.43490215 | 5.868758418 | 0.008529085 | 0.957282449 |
| 1700029J07Rik | 132.3054307 | 298.7066469 | 76.83835866 | 0.257236856 | -1.958830734 | 0.008667624 | 0.965882827 |
| E030024N20Rik | 103.1366902 | 227.776306 | 61.59015165 | 0.270397535 | -1.886846095 | 0.008858574 | 0.974747057 |
| Slc6a17 | 2184.263117 | 1386.638213 | 2450.138085 | 1.766669276 | 0.821271635 | 0.008915421 | 0.974747057 |
| Hmgn2 | 56.97685044 | 148.853814 | 26.35119593 | 0.177027348 | -2.497955843 | 0.008934609 | 0.974747057 |
| Akr1c12 | 746.2705201 | 411.5957809 | 857.8287665 | 2.084153449 | 1.059461502 | 0.009132903 | 0.979040782 |
| Carhsp1 | 297.093596 | 121.8803041 | 355.4980267 | 2.916779946 | 1.544376547 | 0.009172763 | 0.979040782 |
| Mst1 | 26.09401833 | 85.91562418 | 6.153483049 | 0.071622455 | -3.803445363 | 0.009197497 | 0.979040782 |
| Ephx1 | 102.9091246 | 229.7743437 | 60.62071828 | 0.263827185 | -1.922334866 | 0.009298081 | 0.979040782 |
| Spata17 | 19.9620638 | 69.93132201 | 3.305644392 | 0.047269868 | -4.40293534 | 0.009341102 | 0.979040782 |
| Smad9 | 15.8239719 | 57.94309538 | 1.784264072 | 0.030793385 | -5.021235701 | 0.009366325 | 0.979040782 |
| Cd300lf | 14.8267844 | 54.94603872 | 1.453699632 | 0.02645686 | -5.240214364 | 0.009416237 | 0.979040782 |
| Gpx1 | 823.1807359 | 280.7243069 | 1003.899546 | 3.576461036 | 1.838532724 | 0.009476005 | 0.979040782 |
| St8sia3 | 759.3557811 | 421.5859698 | 871.9457183 | 2.068251272 | 1.048411469 | 0.009583968 | 0.983680829 |
| Mef2c | 91.95814881 | 14.98528329 | 117.6157707 | 7.848751899 | 2.972463256 | 0.009739732 | 0.99313438 |
| Gtpbp3 | 64.26162857 | 5.994113315 | 83.68413366 | 13.961053 | 3.803335854 | 0.009876353 | 0.998148762 |
| Gipr | 259.1740891 | 468.5398574 | 189.3854996 | 0.404203605 | -1.306845905 | 0.009950358 | 0.998148762 |
| Mterfd2 | 80.0678122 | 189.8135883 | 43.48588684 | 0.22909786 | -2.125964114 | 0.009980848 | 0.998148762 |
| Dscr3 | 258.4056264 | 467.5408386 | 188.693889 | 0.403588037 | -1.309044685 | 0.010359423 | 1 |
| Rsad1 | 71.46109951 | 176.8263428 | 36.33935175 | 0.2055087 | -2.282728628 | 0.010417955 | 1 |
| Spin2 | 43.45642461 | 120.8812852 | 17.64813775 | 0.145969745 | -2.776003042 | 0.010460312 | 1 |
| A030009H04Rik | 139.1546292 | 287.7174391 | 89.63369253 | 0.311533749 | -1.682539632 | 0.010546558 | 1 |
| Ttll10 | 114.9002011 | 243.7606081 | 71.94673212 | 0.295153235 | -1.760463939 | 0.010556016 | 1 |
| Zfp839 | 176.4527049 | 341.6644589 | 121.3821202 | 0.355267038 | -1.493024256 | 0.01056986 | 1 |
| Unc119b | 236.6692258 | 88.91268084 | 285.9214074 | 3.215575107 | 1.685157543 | 0.010806077 | 1 |
| Fis1 | 258.3436797 | 76.92445421 | 318.8167549 | 4.144543607 | 2.051213242 | 0.010858969 | 1 |
| Serinc2 | 240.9717851 | 73.92739755 | 296.6532476 | 4.012764651 | 2.004596544 | 0.010892107 | 1 |
| Mtap6 | 184.4186426 | 355.6507233 | 127.3412823 | 0.358051521 | -1.4817609 | 0.010939889 | 1 |
| Ush1g | 44.14456331 | 123.8783418 | 17.56663714 | 0.141805535 | -2.818014036 | 0.011079634 | 1 |
| Ppig | 1507.947172 | 2175.863133 | 1285.308518 | 0.590712025 | -0.759473113 | 0.011183814 | 1 |
| Rala | 319.743029 | 139.862644 | 379.7031573 | 2.714828967 | 1.440861312 | 0.011239188 | 1 |
| Ush2a | 804.4036655 | 1224.797154 | 664.2725026 | 0.542353075 | -0.882695735 | 0.01138955 | 1 |
| 4933411K20Rik | 989.5923819 | 1473.552857 | 828.2722237 | 0.562091967 | -0.831121898 | 0.011434747 | 1 |
| Gpm6b | 14.22869355 | 52.94800095 | 1.322257757 | 0.024972761 | -5.323500872 | 0.01151728 | 1 |
| Arc | 111.847008 | 239.7645326 | 69.20783318 | 0.288649169 | -1.792611021 | 0.01161218 | 1 |
| Sema6d | 293.8280289 | 515.4937451 | 219.9394569 | 0.426657858 | -1.228848477 | 0.01164791 | 1 |
| Dusp26 | 11.98456385 | 45.95486875 | 0.661128878 | 0.014386482 | -6.119142374 | 0.011654718 | 1 |
| Krtcap2 | 783.3223359 | 444.5634042 | 896.2419798 | 2.016004852 | 1.011499111 | 0.011717538 | 1 |
| 2610037D02Rik | 30.80442562 | 95.90581304 | 9.103963153 | 0.094926083 | -3.397051639 | 0.011760204 | 1 |
| Ift46 | 186.0249008 | 60.94015203 | 227.7198171 | 3.736777962 | 1.901794842 | 0.011839368 | 1 |
| Bcar1 | 505.6767748 | 257.7468725 | 588.3200755 | 2.282549812 | 1.190646345 | 0.011896315 | 1 |
| Aaas | 168.5382744 | 325.6801568 | 116.157647 | 0.356667178 | -1.487167108 | 0.011915945 | 1 |
| Sepw1 | 372.2169467 | 171.8312484 | 439.0121795 | 2.554903044 | 1.353268543 | 0.012082112 | 1 |
| Eif6 | 465.2566994 | 232.7714004 | 542.751799 | 2.331694521 | 1.221378791 | 0.012166414 | 1 |
| Fam43a | 79.91294912 | 187.8155505 | 43.94541532 | 0.233981772 | -2.095531952 | 0.012262902 | 1 |
| Fam129a | 127.2652859 | 263.7409858 | 81.77338598 | 0.31005979 | -1.689418502 | 0.012263041 | 1 |
| Cox6a2 | 575.4274722 | 302.7027224 | 666.3357221 | 2.20128751 | 1.138347588 | 0.012286981 | 1 |
| BC016495 | 45.85322289 | 124.8773607 | 19.51184361 | 0.156248046 | -2.678089946 | 0.012291213 | 1 |
| Grem2 | 405.7759667 | 193.8096638 | 476.431401 | 2.458243782 | 1.297627993 | 0.012414536 | 1 |
| Gpr158 | 2694.466721 | 3770.297275 | 2335.856536 | 0.61954174 | -0.69072661 | 0.012461845 | 1 |
| Fnbp4 | 976.3796444 | 1470.5558 | 811.6542593 | 0.55193707 | -0.85742431 | 0.012475549 | 1 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Ubl5 | 475.8358909 | 241.7625704 | 553.8603311 | 2.290926715 | 1.195931309 | 0.012564173 | 1 |
| Slc23a2 | 1325.685089 | 758.2553343 | 1514.828341 | 1.997781318 | 0.998398671 | 0.012588027 | 1 |
| Ndor1 | 429.8267035 | 694.3181256 | 341.6628962 | 0.49208408 | -1.023023252 | 0.012807815 | 1 |
| 2210019I11Rik | 170.6620464 | 53.94701983 | 209.5670553 | 3.884682712 | 1.957796769 | 0.012886208 | 1 |
| 2900010M23Rik | 478.4758487 | 207.7959282 | 568.7024888 | 2.736831725 | 1.452506733 | 0.01313826 | 1 |
| Wfikkn2 | 8.491660529 | 33.96664212 | 0 | 0 | #NAME? | 0.01318776 | 1 |
| BC052040 | 190.6770446 | 358.64778 | 134.6867994 | 0.375540592 | -1.41295924 | 0.013195464 | 1 |
| Ptpmt1 | 114.7723648 | 26.97350992 | 144.0386497 | 5.340003958 | 2.416840811 | 0.013204016 | 1 |
| Iqsec2 | 104.9185068 | 228.7753248 | 63.63290076 | 0.278145822 | -1.84608666 | 0.013511336 | 1 |
| 2810454H06Rik | 34.53331918 | 101.8999264 | 12.07778345 | 0.118525929 | -3.076725392 | 0.013743684 | 1 |
| Gm5506 | 84.67478541 | 13.9862644 | 108.2376257 | 7.738851679 | 2.952119509 | 0.013807261 | 1 |
| Dom3z | 143.9441357 | 289.7154769 | 95.35368862 | 0.329128736 | -1.603276104 | 0.013949348 | 1 |
| Txlna | 664.0022971 | 367.63895 | 762.7900795 | 2.074834779 | 1.052996458 | 0.014025151 | 1 |
| Ndufa10 | 511.1454786 | 262.741967 | 593.9466492 | 2.260570156 | 1.176686692 | 0.014052469 | 1 |
| Pak3 | 1453.175941 | 2088.94849 | 1241.251758 | 0.594199313 | -0.750981157 | 0.014133127 | 1 |
| Il6ra | 1311.573815 | 1883.1506 | 1121.04822 | 0.595304603 | -0.748300046 | 0.014234892 | 1 |
| Arl6ip4 | 248.3668594 | 97.90385081 | 298.5211956 | 3.04912619 | 1.608395858 | 0.01423705 | 1 |
| Odf2 | 604.7560908 | 940.0767715 | 492.9825306 | 0.524406671 | -0.931242056 | 0.014665467 | 1 |
| Cd93 | 39.77321847 | 0.999018886 | 52.69795167 | 52.74970516 | 5.721091125 | 0.014691258 | 1 |
| Capg | 8.241905808 | 32.96762323 | 0 | 0 | #NAME? | 0.014866189 | 1 |
| Ptprk | 42.49711273 | 117.8842285 | 17.36807413 | 0.147331618 | -2.762861022 | 0.014894166 | 1 |
| Spin4 | 52.11335849 | 132.8695118 | 25.19464071 | 0.189619427 | -2.398821314 | 0.015285803 | 1 |
| Ndufa5 | 113.7351011 | 17.98233994 | 145.6526881 | 8.099762799 | 3.017879659 | 0.015306297 | 1 |
| Nkrf | 234.2204936 | 92.90875638 | 281.3244406 | 3.027964392 | 1.59834824 | 0.015617042 | 1 |
| Mtap1a | 82.48288773 | 187.8155505 | 47.37200013 | 0.252226187 | -1.987210027 | 0.015769673 | 1 |
| Cep290 | 947.7852289 | 1400.624478 | 796.8388126 | 0.568916812 | -0.813710381 | 0.015778122 | 1 |
| Banp | 272.0150785 | 473.5349519 | 204.8417873 | 0.43258008 | -1.208960863 | 0.016068764 | 1 |
| Hibch | 206.3062244 | 381.6252144 | 147.8665611 | 0.387465385 | -1.36786006 | 0.016076633 | 1 |
| 2810407C02Rik | 4228.601729 | 2910.142014 | 4668.0883 | 1.604075773 | 0.681742293 | 0.016268856 | 1 |
| Dock3 | 153.7289053 | 46.95388763 | 189.3205779 | 4.032053306 | 2.011514712 | 0.016461182 | 1 |
| Gpr119 | 94.23999086 | 225.7782682 | 50.39389842 | 0.223200837 | -2.163585658 | 0.016539453 | 1 |
| Pla2g16 | 110.447192 | 229.7743437 | 70.67147471 | 0.307569042 | -1.701017799 | 0.016629251 | 1 |
| Cnn3 | 422.1118975 | 210.7929849 | 492.551535 | 2.336625995 | 1.224447824 | 0.016638581 | 1 |
| 9330162B11Rik | 9.763248096 | 37.96271766 | 0.363424908 | 0.009573206 | -6.706782164 | 0.016728787 | 1 |
| Fgfbp1 | 7.992151086 | 31.96860435 | 0 | 0 | #NAME? | 0.016756337 | 1 |
| Pdgfrb | 7.992151086 | 31.96860435 | 0 | 0 | #NAME? | 0.016756337 | 1 |
| Zbtb34 | 361.2109228 | 596.4142748 | 282.8098055 | 0.474183495 | -1.076482646 | 0.016821389 | 1 |
| Syne1 | 1014.715628 | 1474.551875 | 861.4368793 | 0.584202491 | -0.775459584 | 0.016840019 | 1 |
| D4Ertd22e | 322.8578862 | 146.8557762 | 381.5252563 | 2.597958801 | 1.377378552 | 0.016931136 | 1 |
| Epdr1 | 39.62283772 | 109.8920774 | 16.19975781 | 0.147415157 | -2.76204323 | 0.016941233 | 1 |
| Rfxank | 60.27130093 | 148.853814 | 30.74379657 | 0.206550885 | -2.275525495 | 0.016955392 | 1 |
| D930020B18Rik | 9.714482465 | 37.96271766 | 0.298404067 | 0.007860451 | -6.991172267 | 0.016966585 | 1 |
| Aasdh | 131.4892047 | 261.7429481 | 88.07129019 | 0.336480088 | -1.571406963 | 0.017045033 | 1 |
| Baiap2 | 82.92154062 | 188.8454694 | 47.62386435 | 0.25222558 | -1.987213496 | 0.017220534 | 1 |
| Iqgap2 | 1283.687248 | 809.2052975 | 1441.847898 | 1.78180729 | 0.833341321 | 0.017360371 | 1 |
| Glce | 1752.844627 | 1143.876624 | 1955.833962 | 1.70982947 | 0.773852445 | 0.01739395 | 1 |
| Bmyc | 334.4996982 | 559.450576 | 259.5160723 | 0.463876674 | -1.108186794 | 0.017396077 | 1 |
| Copz2 | 557.0892452 | 867.1483929 | 453.736196 | 0.523250922 | -0.934425147 | 0.017820698 | 1 |
| Ube3c | 1279.887696 | 808.2062786 | 1437.114835 | 1.778153515 | 0.830379883 | 0.017940742 | 1 |
| Dad1 | 1659.430627 | 1076.942359 | 1853.593383 | 1.721163039 | 0.783383764 | 0.01797145 | 1 |
| Dusp10 | 553.8401637 | 254.7498159 | 653.5369463 | 2.565406943 | 1.359187694 | 0.017972515 | 1 |
| Snx32 | 181.9506436 | 335.6703456 | 130.7107429 | 0.389402116 | -1.360667371 | 0.018027568 | 1 |
| Marcksl1-ps4 | 91.3628106 | 17.98233994 | 115.8229675 | 6.440928591 | 2.687268697 | 0.018069794 | 1 |
| Rnaseh2a | 54.90515919 | 4.995094429 | 71.54184745 | 14.32242142 | 3.840203517 | 0.018086716 | 1 |
| Memo1 | 418.0341871 | 211.7920038 | 486.7815815 | 2.298394523 | 1.20062646 | 0.018152736 | 1 |
| Tapbp | 1501.738693 | 976.0414514 | 1676.971107 | 1.718135131 | 0.780843509 | 0.018667325 | 1 |
| 1500032L24Rik | 528.5438465 | 288.716458 | 608.4863094 | 2.107556714 | 1.075571454 | 0.018712234 | 1 |
| Tal2 | 7.742396365 | 30.96958546 | 0 | 0 | #NAME? | 0.018884459 | 1 |
| Adora2a | 41.43438415 | 0 | 55.24584553 | Inf | Inf | 0.018964243 | 1 |
| Bmpr1b | 47.48659278 | 123.8783418 | 22.02267642 | 0.177776648 | -2.491862261 | 0.018975736 | 1 |
| Bcl9 | 908.3311787 | 1327.696099 | 768.5428719 | 0.578854508 | -0.788727316 | 0.018978064 | 1 |
| Pygb | 69.71760726 | 162.8400784 | 38.67678356 | 0.237513909 | -2.073916904 | 0.019118353 | 1 |
| Znhit6 | 230.5982163 | 408.5987243 | 171.2647136 | 0.419151366 | -1.254456763 | 0.019301745 | 1 |
| 5930403L14Rik | 14.5240762 | 51.94898206 | 2.049107573 | 0.039444615 | -4.66402785 | 0.019336696 | 1 |
| Smap2 | 1861.735094 | 1227.794211 | 2073.048722 | 1.688433375 | 0.755685252 | 0.019465447 | 1 |
| Itgb2l | 26.79894609 | 80.92052975 | 8.758418207 | 0.108234815 | -3.207763521 | 0.019515285 | 1 |
| Vipr2 | 44.55664112 | 117.8842285 | 20.11411198 | 0.17062598 | -2.551090765 | 0.019581177 | 1 |
| Ret | 820.0320619 | 1206.814814 | 691.1044779 | 0.572668209 | -0.804228579 | 0.019785268 | 1 |
| Cox8a | 1367.305127 | 877.1385817 | 1530.693976 | 1.745099358 | 0.803309179 | 0.019916456 | 1 |
| Ndufaf4 | 250.6262618 | 106.8950208 | 298.5366754 | 2.792802445 | 1.481713525 | 0.01995474 | 1 |
| 6430550D23Rik | 26.55144243 | 80.92052975 | 8.428413325 | 0.104156675 | -3.263172795 | 0.020009078 | 1 |
| Ccdc14 | 30.50015492 | 90.91071861 | 10.36330036 | 0.113994263 | -3.132966876 | 0.02006723 | 1 |
| Zfp398 | 426.7795099 | 676.3357857 | 343.5940846 | 0.508022926 | -0.977034492 | 0.020073849 | 1 |
| Map4k3 | 685.0945005 | 1018.999264 | 573.7929128 | 0.563094531 | -0.828550955 | 0.020333643 | 1 |
| Alox8 | 66.75013396 | 153.8489084 | 37.71720914 | 0.24515747 | -2.028219374 | 0.020444607 | 1 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Ssx2ip | 347.0500948 | 167.8351728 | 406.7884022 | 2.4237375 | 1.277233458 | 0.020455457 | 1 |
| Mysm1 | 1401.573355 | 1975.060337 | 1210.411028 | 0.61284762 | -0.706399691 | 0.020733276 | 1 |
| Sdhd | 975.6134685 | 589.4211426 | 1104.344244 | 1.873608128 | 0.90581924 | 0.021091553 | 1 |
| B3galt5 | 266.8893354 | 456.5516308 | 203.6685703 | 0.446101945 | -1.164554658 | 0.021099703 | 1 |
| Elovl2 | 788.391855 | 469.5388763 | 894.6761812 | 1.905435793 | 0.930120995 | 0.021135918 | 1 |
| Gm15441 | 7.492641643 | 29.97056657 | 0 | 0 | #NAME? | 0.02127996 | 1 |
| Cth | 75.89145944 | 2.997056657 | 100.1895937 | 33.42932923 | 5.063042502 | 0.021294003 | 1 |
| Dcx | 1426.898542 | 924.0924694 | 1594.500566 | 1.725477286 | 0.786995483 | 0.021627857 | 1 |
| Slbp | 156.4603153 | 296.7086091 | 109.710884 | 0.369759692 | -1.43534013 | 0.021715085 | 1 |
| Gdap10 | 185.2931442 | 337.6683834 | 134.5013977 | 0.398323931 | -1.327985938 | 0.021958042 | 1 |
| Tfb1m | 72.62239557 | 162.8400784 | 42.54983463 | 0.261298294 | -1.936230391 | 0.022036294 | 1 |
| 1110059E24Rik | 418.1061239 | 209.793966 | 487.5435099 | 2.323915788 | 1.216557791 | 0.022037973 | 1 |
| Plekhb1 | 107.348896 | 227.776306 | 67.20642604 | 0.295054509 | -1.760946591 | 0.022066734 | 1 |
| 2310061I04Rik | 261.1635838 | 114.8871719 | 309.9223878 | 2.697623962 | 1.431689257 | 0.022137274 | 1 |
| Zfp579 | 66.13002312 | 151.8508706 | 37.55640728 | 0.24732428 | -2.015524217 | 0.022141795 | 1 |
| B3gnt3 | 247.637691 | 425.5820453 | 188.3229062 | 0.442506699 | -1.176228798 | 0.022143372 | 1 |
| Immp1l | 520.4829057 | 288.716458 | 597.7383883 | 2.070330152 | 1.04986085 | 0.022144122 | 1 |
| Ptpn3 | 126.2489432 | 250.7537403 | 84.74734422 | 0.337970409 | -1.565031157 | 0.022226921 | 1 |
| C130083M11Rik | 63.14303411 | 151.8508706 | 33.57375527 | 0.22109689 | -2.177249362 | 0.022231796 | 1 |
| Setd2 | 1946.923343 | 2674.373557 | 1704.439903 | 0.637323306 | -0.649903233 | 0.022252345 | 1 |
| Myadm | 890.5377794 | 1288.734363 | 757.805585 | 0.588023108 | -0.766055245 | 0.022304872 | 1 |
| Ccdc15 | 126.8734966 | 252.7517781 | 84.91406941 | 0.335958346 | -1.573645723 | 0.022370481 | 1 |
| Solh | 150.3518724 | 285.7194013 | 105.2293628 | 0.368296175 | -1.441061679 | 0.022444392 | 1 |
| Slc4a10 | 1431.823019 | 2000.035809 | 1242.418756 | 0.621198255 | -0.686874317 | 0.022526013 | 1 |
| Lamtor2 | 157.2458949 | 53.94701983 | 191.6788533 | 3.553094386 | 1.829076013 | 0.022616951 | 1 |
| Tmem14c | 224.1378358 | 92.90875638 | 267.8808623 | 2.883268195 | 1.527705039 | 0.022711628 | 1 |
| Tmem59l | 84.48357577 | 181.8214372 | 52.03762196 | 0.286201796 | -1.804895367 | 0.02297123 | 1 |
| Fastkd1 | 138.5876809 | 42.95781209 | 170.4643038 | 3.968477241 | 1.988477241 | 0.023069975 | 1 |
| Bmf | 75.63764245 | 170.8322295 | 43.90611344 | 0.257013056 | -1.960086444 | 0.023102674 | 1 |
| Sox5 | 72.00388398 | 166.8361539 | 40.39312733 | 0.242112554 | -2.046250207 | 0.023103723 | 1 |
| Tomm7 | 163.8590756 | 51.94898206 | 201.16244 | 3.872307638 | 1.953193573 | 0.023156681 | 1 |
| Eral1 | 155.2795384 | 292.7125335 | 109.4685401 | 0.373979681 | -1.418968205 | 0.02319876 | 1 |
| Pitrm1 | 801.5865022 | 1173.847191 | 677.4996059 | 0.577161671 | -0.792952601 | 0.023217157 | 1 |
| Ndufa7 | 320.6824502 | 154.8479273 | 375.9606245 | 2.427934497 | 1.2797295 | 0.023217328 | 1 |
| Eif4e3 | 434.0089226 | 680.3318612 | 351.9012764 | 0.517249443 | -0.951067908 | 0.023217663 | 1 |
| Lrrcc1 | 406.9579795 | 646.3652191 | 327.1555663 | 0.506146613 | -0.982372752 | 0.023226367 | 1 |
| Ap1m2 | 213.9275801 | 86.91464306 | 256.2652257 | 2.948467093 | 1.559966561 | 0.023230587 | 1 |
| Ttc14 | 1455.658675 | 2026.0103 | 1265.541467 | 0.624647104 | -0.678886729 | 0.02327008 | 1 |
| Dagla | 832.5529908 | 1205.815795 | 708.1320561 | 0.587263875 | -0.767919201 | 0.023343629 | 1 |
| Dennd2d | 271.998636 | 458.5496686 | 209.8149585 | 0.45756212 | -1.127960473 | 0.023475251 | 1 |
| Ssfa2 | 698.0331979 | 1030.98749 | 587.0484338 | 0.569404032 | -0.812475386 | 0.023502307 | 1 |
| C85492 | 121.5672368 | 243.7606081 | 80.83611299 | 0.331620903 | -1.592393148 | 0.023506791 | 1 |
| Prr22 | 32.22595806 | 90.91071861 | 12.66437122 | 0.139305589 | -2.843674953 | 0.023549884 | 1 |
| Plac8 | 7.242886922 | 28.97154769 | 0 | 0 | #NAME? | 0.02397574 | 1 |
| Pcdhac2 | 29.79267968 | 86.91464306 | 10.75202521 | 0.123707868 | -3.014990831 | 0.02420802 | 1 |
| Ica1l | 339.6830231 | 553.4564627 | 268.4252099 | 0.484997878 | -1.04394966 | 0.024415935 | 1 |
| Kcnab1 | 37.79784248 | 101.8999264 | 16.43048119 | 0.161241345 | -2.632706371 | 0.024555687 | 1 |
| Pfdn4 | 111.4133587 | 29.97056657 | 138.5609561 | 4.623234458 | 2.208902528 | 0.024566917 | 1 |
| Rtkn2 | 299.1525382 | 141.8606818 | 351.583017 | 2.478369289 | 1.309391172 | 0.024646379 | 1 |
| Herpud1 | 2138.228711 | 1459.566592 | 2364.449417 | 1.619966797 | 0.695964244 | 0.024736279 | 1 |
| Zfyve16 | 566.5830139 | 861.1542796 | 468.392592 | 0.543912517 | -0.878553467 | 0.024737945 | 1 |
| Ift172 | 546.1697799 | 829.1856752 | 451.8311482 | 0.544909496 | -0.875911463 | 0.024775454 | 1 |
| Cep192 | 490.5600482 | 753.2602399 | 402.9933123 | 0.534989781 | -0.902392483 | 0.025040339 | 1 |
| A630089N07Rik | 40.00943649 | 107.8940397 | 17.38123543 | 0.161095418 | -2.634012634 | 0.025077324 | 1 |
| Dock1 | 36.99080138 | 100.9009075 | 15.68743268 | 0.155473653 | -2.685257976 | 0.025156386 | 1 |
| Parp3 | 28.02734574 | 82.91856752 | 9.730271812 | 0.117347322 | -3.091143181 | 0.025293984 | 1 |
| Gm2447 | 17.26274624 | 57.94309538 | 3.702629866 | 0.06390114 | -3.968014514 | 0.025321564 | 1 |
| Pfdn2 | 149.1519423 | 49.95094429 | 182.2189088 | 3.64795792 | 1.867089048 | 0.025427446 | 1 |
| Gca | 572.4603531 | 881.1346573 | 469.5689184 | 0.532913913 | -0.908025595 | 0.025460495 | 1 |
| Aff2 | 1624.552151 | 2394.648269 | 1367.853445 | 0.571212676 | -0.8079001 | 0.025638213 | 1 |
| Dcp1a | 727.8656801 | 1063.955113 | 615.835869 | 0.578817528 | -0.788819483 | 0.02570339 | 1 |
| Mettl2 | 45.67435005 | 116.8852096 | 21.93739605 | 0.187692375 | -2.413628139 | 0.025791204 | 1 |
| Ggt7 | 241.5319897 | 412.5947998 | 184.511053 | 0.447196749 | -1.161018396 | 0.025850659 | 1 |
| Synj2 | 155.6621914 | 301.7037035 | 106.9816873 | 0.354591893 | -1.495768543 | 0.025893939 | 1 |
| Ovol2 | 96.96239052 | 22.97743437 | 121.6240426 | 5.293195079 | 2.404138825 | 0.02592148 | 1 |
| Msln | 22.04430074 | 68.93230312 | 6.414666607 | 0.093061545 | -3.425666558 | 0.026166599 | 1 |
| Dstyk | 267.1632343 | 450.5575175 | 206.0318066 | 0.45728192 | -1.128844216 | 0.026268885 | 1 |
| Itsn2 | 858.7273155 | 1234.787343 | 733.373973 | 0.593927349 | -0.751641628 | 0.026298917 | 1 |
| Pcdhb19 | 41.82605036 | 107.8940397 | 19.80338725 | 0.183544775 | -2.445796048 | 0.026480725 | 1 |
| Wrnip1 | 262.8043506 | 453.5545742 | 199.2209091 | 0.439243539 | -1.186907031 | 0.026562434 | 1 |
| Zfp608 | 548.6504977 | 827.1876374 | 455.8047845 | 0.551029493 | -0.859798556 | 0.026615913 | 1 |
| Sowahb | 170.238797 | 62.93818981 | 206.005666 | 3.273142534 | 1.710676428 | 0.02670498 | 1 |
| Fam188b | 66.02052471 | 152.8498895 | 37.07740311 | 0.242573961 | -2.043503403 | 0.026778779 | 1 |
| Cckar | 6.993132201 | 27.9725288 | 0 | 0 | #NAME? | 0.027008581 | 1 |
| Yod1 | 256.1502226 | 431.5761587 | 197.6749106 | 0.458030191 | -1.126485397 | 0.027013217 | 1 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Tkt | 315.2427625 | 153.8489084 | 369.0407139 | 2.398721692 | 1.262265781 | 0.027014901 | 1 |
| Rab25 | 426.8763696 | 229.7743437 | 492.5770449 | 2.143742582 | 1.100131679 | 0.027268315 | 1 |
| Large | 34.35443361 | 95.90581304 | 13.83730714 | 0.144280171 | -2.793055054 | 0.027492468 | 1 |
| Akr1c13 | 636.4737264 | 357.6487611 | 729.4153814 | 2.039474089 | 1.028197179 | 0.02752572 | 1 |
| Gm15708 | 21.76937559 | 67.93328423 | 6.381406042 | 0.093936369 | -3.412172364 | 0.027893013 | 1 |
| Rasd2 | 295.4985845 | 139.862644 | 347.3772313 | 2.483702734 | 1.312492512 | 0.027978198 | 1 |
| Rtl1 | 412.9101585 | 836.1788074 | 271.8206089 | 0.325074741 | -1.621156637 | 0.028036621 | 1 |
| Sh3bgrl | 928.3369581 | 1321.701986 | 797.2152822 | 0.60317325 | -0.729355647 | 0.028074381 | 1 |
| Rpl14 | 719.7073424 | 418.5889131 | 820.0801521 | 1.95915402 | 0.970230821 | 0.028192572 | 1 |
| H2-T23 | 395.3397492 | 80.92052975 | 500.1461557 | 6.180707878 | 2.62777208 | 0.028241097 | 1 |
| Tmem132b | 644.3293757 | 1097.921755 | 493.1319157 | 0.449150327 | -1.15472971 | 0.028242648 | 1 |
| Tsc22d3 | 148.4601677 | 50.94996318 | 180.9635692 | 3.55178999 | 1.828546281 | 0.02824553 | 1 |
| Wapal | 1783.682518 | 2434.609025 | 1566.707016 | 0.643514831 | -0.635954696 | 0.028248159 | 1 |
| Zbtb40 | 236.4597414 | 398.6085354 | 182.4101434 | 0.457617254 | -1.127786646 | 0.028249357 | 1 |
| Srsf9 | 220.4653512 | 93.90777526 | 262.6512099 | 2.796905892 | 1.483831712 | 0.02852641 | 1 |
| Krt19 | 67.78111902 | 0 | 90.37482536 | Inf | Inf | 0.028557019 | 1 |
| Thnsl2 | 28.78678948 | 81.91954864 | 11.07586976 | 0.135204233 | -2.886787771 | 0.028643527 | 1 |
| Dpp6 | 96.82691703 | 14.98528329 | 124.1074616 | 8.281956319 | 3.049971594 | 0.02882012 | 1 |
| 2410002I01Rik | 60.90539575 | 142.8597007 | 33.58729411 | 0.235106849 | -2.088611526 | 0.028865017 | 1 |
| Stk38l | 392.1372441 | 206.7949094 | 453.9173557 | 2.194919044 | 1.134215027 | 0.028876988 | 1 |
| Tmem63a | 825.3331167 | 1188.832474 | 704.1666643 | 0.592317824 | -0.755556594 | 0.02889527 | 1 |
| A930012L18Rik | 44.49184722 | 111.8901152 | 22.02575789 | 0.196851687 | -2.344819022 | 0.028922733 | 1 |
| Slc2a5 | 1521.912328 | 1024.993377 | 1687.551978 | 1.646402812 | 0.719317352 | 0.029177951 | 1 |
| 1190007F08Rik | 134.9711639 | 21.97841549 | 172.6354133 | 7.85477067 | 2.973569155 | 0.029325225 | 1 |
| Caml | 174.9386334 | 65.93524646 | 211.2730958 | 3.204251248 | 1.679987275 | 0.029372569 | 1 |
| Tnfrsf11a | 354.1594337 | 565.4446894 | 283.7310152 | 0.501783853 | -0.994862047 | 0.029662032 | 1 |
| BC018242 | 236.6350391 | 400.6065732 | 181.9778611 | 0.454255804 | -1.138423146 | 0.029738824 | 1 |
| Arhgap12 | 707.9075024 | 1036.981603 | 598.2161354 | 0.57768211 | -0.793651571 | 0.02995507 | 1 |
| Dclk2 | 52.16636091 | 126.8753985 | 27.26334839 | 0.214882859 | -2.218377689 | 0.030022336 | 1 |
| Commd6 | 423.2479066 | 228.7753248 | 488.0721005 | 2.133412337 | 1.093162831 | 0.030087306 | 1 |
| Itgal | 13.8046027 | 48.9519254 | 2.088828469 | 0.042671018 | -4.550599675 | 0.030090052 | 1 |
| Rhou | 405.9221835 | 213.7900416 | 469.9662308 | 2.198260627 | 1.136362443 | 0.030096161 | 1 |
| Anln | 38.92398305 | 1.998037772 | 51.23263147 | 25.64147295 | 4.680407233 | 0.030273602 | 1 |
| Ptch2 | 17.23784472 | 56.94407649 | 4.002434126 | 0.070287102 | -3.830596212 | 0.030378232 | 1 |
| Glt25d1 | 243.3967555 | 411.5957809 | 187.3304137 | 0.455132007 | -1.135643049 | 0.030443736 | 1 |
| Nr1d1 | 616.3618841 | 1195.825606 | 423.20731 | 0.35390387 | -1.498570557 | 0.030488026 | 1 |
| Ermp1 | 418.6148837 | 652.3593324 | 340.7000675 | 0.522258287 | -0.937164615 | 0.030535576 | 1 |
| Hdac10 | 81.66601894 | 174.828305 | 50.61192359 | 0.28949502 | -1.788389566 | 0.030666006 | 1 |
| Alg2 | 1949.894421 | 2632.414764 | 1722.38764 | 0.654299491 | -0.611976946 | 0.030709216 | 1 |
| Sh3pxd2a | 1779.440319 | 2424.618836 | 1564.380814 | 0.645206904 | -0.632166218 | 0.030796904 | 1 |
| Has3 | 34.04248491 | 92.90875628 | 14.42039448 | 0.155210283 | -2.687703948 | 0.030826702 | 1 |
| Nrcam | 961.1015519 | 610.4005392 | 1078.001889 | 1.766056581 | 0.820531565 | 0.030885609 | 1 |
| Trappc3 | 593.7421697 | 285.7194013 | 696.4164258 | 2.437413849 | 1.285351227 | 0.03090873 | 1 |
| Mipep | 146.5737872 | 50.94996318 | 178.4483953 | 3.502424421 | 1.808353919 | 0.030956174 | 1 |
| Lancl3 | 15.96268705 | 52.94800095 | 3.634642901 | 0.068630679 | -3.86484701 | 0.031151145 | 1 |
| Evi2a | 19.38828216 | 62.93818981 | 4.871646285 | 0.077403661 | -3.691454393 | 0.031161183 | 1 |
| Nalcn | 447.88373 | 694.3181256 | 365.7389314 | 0.526759878 | -0.924782631 | 0.031538617 | 1 |
| Bclaf1 | 3199.986761 | 4210.864604 | 2863.027481 | 0.6799144 | -0.55657497 | 0.031545426 | 1 |
| Mlxipl | 3852.496031 | 6052.05641 | 3119.309237 | 0.515253114 | -0.956169851 | 0.031551185 | 1 |
| Tmem192 | 172.1285733 | 65.93524646 | 207.5263489 | 3.147426604 | 1.654172736 | 0.031670356 | 1 |
| Brd1 | 549.1344206 | 317.6880057 | 626.2832255 | 1.971378253 | 0.979204616 | 0.031826872 | 1 |
| Mrpl51 | 221.125411 | 96.90483192 | 262.5322707 | 2.709176266 | 1.437854262 | 0.031860927 | 1 |
| Arpc5l | 743.0002587 | 457.5506497 | 838.1501283 | 1.831819338 | 0.873277226 | 0.031881238 | 1 |
| B2m | 5682.826718 | 2994.059601 | 6579.082424 | 2.197378577 | 1.135783447 | 0.031911501 | 1 |
| Pard6b | 117.4158451 | 34.965661 | 144.8992398 | 4.144044062 | 2.051039343 | 0.032123969 | 1 |
| Sc4mol | 682.8242991 | 415.5918565 | 771.90178 | 1.857355403 | 0.8932499 | 0.03216798 | 1 |
| Gnai3 | 1826.282195 | 1251.770664 | 2017.786039 | 1.61194546 | 0.688802932 | 0.032249902 | 1 |
| E2f1 | 46.15162445 | 3.996075543 | 60.20347408 | 15.06564964 | 3.913190979 | 0.032263735 | 1 |
| Gga3 | 339.2905317 | 534.4751039 | 274.2290076 | 0.513080975 | -0.962741562 | 0.032270123 | 1 |
| Hspa1a | 33.81245367 | 0.999018886 | 44.75026526 | 44.7942135 | 5.485240472 | 0.032284916 | 1 |
| Exoc4 | 765.3837048 | 1098.920774 | 654.2046815 | 0.595315601 | -0.748273392 | 0.032318314 | 1 |
| 4930402H24Rik | 616.7516914 | 910.106205 | 518.9668535 | 0.570226695 | -0.810392514 | 0.03239363 | 1 |
| Cnih | 392.3348983 | 210.7929849 | 452.8488695 | 2.148310911 | 1.1032028 | 0.032409997 | 1 |
| Cerkl | 230.5959702 | 388.6183466 | 177.9218447 | 0.45783182 | -1.127110361 | 0.032466749 | 1 |
| Atp6v1g2 | 50.5544457 | 120.8812852 | 27.11216587 | 0.224287538 | -2.156578631 | 0.032501943 | 1 |
| Ppt2 | 30.04331394 | 83.91758641 | 12.07162312 | 0.143850957 | -2.797353514 | 0.032503681 | 1 |
| D730039F16Rik | 62.77939741 | 4.995094429 | 82.04083173 | 16.42428044 | 4.037758261 | 0.032520251 | 1 |
| Ung | 101.1233926 | 26.97350992 | 125.8400202 | 4.665318699 | 2.221975639 | 0.032719314 | 1 |
| Rapgef6 | 913.0266584 | 1289.733382 | 787.4577507 | 0.610558556 | -0.711798431 | 0.03280829 | 1 |
| Lpl | 1984.053266 | 2691.356878 | 1748.285396 | 0.649592557 | -0.622392993 | 0.032845209 | 1 |
| Alkbh5 | 1211.417307 | 802.2121653 | 1347.81902 | 1.680127875 | 0.748571041 | 0.032927002 | 1 |
| Tmem188 | 525.5916088 | 300.7046846 | 600.5539168 | 1.997155174 | 0.997946431 | 0.032967932 | 1 |
| Zfp182 | 361.5518692 | 568.441746 | 292.5885769 | 0.514720425 | -0.958139063 | 0.033167456 | 1 |
| Prom1 | 1821.978073 | 3339.720135 | 1316.064053 | 0.394064173 | -1.343497505 | 0.0331934 | 1 |
| Cacna1b | 24.90148461 | 72.92837866 | 8.89251993 | 0.121934974 | -3.035816113 | 0.033319288 | 1 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Cobra1 | 378.0698209 | 598.4123126 | 304.6223237 | 0.509050896 | -0.974118189 | 0.033416803 | 1 |
| Cadps | 2814.514829 | 3727.339463 | 2510.239952 | 0.673466953 | -0.57032094 | 0.033430775 | 1 |
| Ccdc19 | 21.95060847 | 67.93328423 | 6.623049887 | 0.097490445 | -3.358550973 | 0.033438865 | 1 |
| Inha | 285.7623448 | 497.5114051 | 215.1793246 | 0.43251134 | -1.209190135 | 0.033452024 | 1 |
| Oxa1l | 303.1103817 | 150.8518518 | 353.863225 | 2.345766531 | 1.230059432 | 0.033485152 | 1 |
| Lrrc27 | 210.8203696 | 392.6144221 | 150.2223521 | 0.382620565 | -1.386013677 | 0.033511554 | 1 |
| Agrn | 135.7166843 | 252.7517781 | 96.70498641 | 0.382608531 | -1.386059055 | 0.033542895 | 1 |
| Calca | 11.13515578 | 40.95977432 | 1.193616268 | 0.029141183 | -5.100796758 | 0.033579798 | 1 |
| D430042O09Rik | 289.4284907 | 474.5339708 | 227.726664 | 0.479895388 | -1.059208147 | 0.033708755 | 1 |
| Cdyl | 99.48693763 | 198.8047583 | 66.38099742 | 0.333900446 | -1.582510075 | 0.033755761 | 1 |
| Ripk2 | 352.9073756 | 134.8675496 | 425.5873175 | 3.155594647 | 1.657911895 | 0.033757085 | 1 |
| Psmb10 | 199.4034123 | 52.94800095 | 248.2218827 | 4.688031243 | 2.228982185 | 0.033790506 | 1 |
| 1700016K19Rik | 53.7693116 | 125.8763796 | 29.73362227 | 0.236212881 | -2.081840457 | 0.033876797 | 1 |
| Fgl2 | 618.6196473 | 369.6369877 | 701.6138671 | 1.898115964 | 0.924568135 | 0.033909888 | 1 |
| Ocrl | 1252.952063 | 829.1856752 | 1394.207526 | 1.681417767 | 0.749678222 | 0.033930018 | 1 |
| Bid | 42.01933958 | 105.8960019 | 20.7271188 | 0.195730845 | -2.353056629 | 0.034110874 | 1 |
| Gatsl2 | 1141.572364 | 1590.438066 | 991.9504629 | 0.623696379 | -0.681084212 | 0.034194451 | 1 |
| C130021I20Rik | 20.80197877 | 64.93622758 | 6.090562498 | 0.093792983 | -3.414376194 | 0.034254065 | 1 |
| Acsf2 | 6.493622758 | 25.97449103 | 0 | 0 | #NAME? | 0.034254505 | 1 |
| 4930480K15Rik | 81.30357862 | 170.8322295 | 51.46069501 | 0.301235283 | -1.731037335 | 0.034323662 | 1 |
| Dync2h1 | 1295.078004 | 1768.263428 | 1137.34953 | 0.64320141 | -0.636657526 | 0.034375352 | 1 |
| Gp5 | 12.67826188 | 44.95584986 | 1.919065891 | 0.04268779 | -4.550032706 | 0.034458043 | 1 |
| Pafah2 | 87.70866508 | 180.8224183 | 56.67074733 | 0.313405538 | -1.673897421 | 0.034608395 | 1 |
| Mrpl40 | 128.7491532 | 41.9587932 | 157.6792733 | 3.757955394 | 1.909947943 | 0.034674305 | 1 |
| Hes1 | 65.1935205 | 10.98920774 | 83.26162476 | 7.576672195 | 2.921564331 | 0.034770781 | 1 |
| A2ld1 | 181.8912083 | 73.92739755 | 217.8791452 | 2.947204317 | 1.55934708 | 0.035052855 | 1 |
| Bcl11a | 85.9760757 | 177.8253617 | 55.35964705 | 0.311314688 | -1.683554448 | 0.035114355 | 1 |
| Itpr1 | 328.7101682 | 592.4181993 | 240.8074912 | 0.406482225 | -1.298735688 | 0.035143064 | 1 |
| Star | 754.0175236 | 467.5408386 | 849.509752 | 1.816974437 | 0.861538123 | 0.035164396 | 1 |
| Pcbd1 | 1649.467277 | 1029.988471 | 1855.960212 | 1.801923288 | 0.849537593 | 0.035275485 | 1 |
| 1500016L03Rik | 81.02638404 | 166.8361539 | 52.42312741 | 0.314219228 | -1.670156631 | 0.035326321 | 1 |
| Vapa | 633.6795854 | 384.622271 | 716.6986902 | 1.863383231 | 0.897924415 | 0.035348524 | 1 |
| Gm3414 | 209.6468415 | 357.6487611 | 160.3128683 | 0.448241084 | -1.157653209 | 0.035404818 | 1 |
| Crip1 | 134.8524397 | 45.95486875 | 164.4849633 | 3.579271747 | 1.839666081 | 0.035514852 | 1 |
| Tmem9 | 424.0414256 | 655.3563891 | 346.9364378 | 0.529385909 | -0.9176083 | 0.03561348 | 1 |
| 4930420K17Rik | 240.8600804 | 398.6085354 | 188.277262 | 0.472336253 | -1.082113825 | 0.035785087 | 1 |
| Gtdc1 | 232.7612614 | 387.6193277 | 181.4458918 | 0.468103314 | -1.095101116 | 0.035793743 | 1 |
| Dph1 | 32.9602313 | 0.999018886 | 43.61396877 | 43.65680108 | 5.448134517 | 0.036122306 | 1 |
| Rit2 | 86.8842696 | 180.8224183 | 55.57155336 | 0.307326679 | -1.702155081 | 0.036205907 | 1 |
| Cpox | 594.6332651 | 875.140544 | 501.1308388 | 0.572628982 | -0.804327405 | 0.036347645 | 1 |
| Fbxl21 | 57.03708368 | 131.8704929 | 32.09261393 | 0.243364632 | -2.03880858 | 0.036536019 | 1 |
| Gm15910 | 18.18958051 | 58.94211426 | 4.60540259 | 0.07813433 | -3.677899628 | 0.036651517 | 1 |
| Fgfr1 | 191.6973399 | 333.6723079 | 144.3723506 | 0.432677052 | -1.208637487 | 0.036669769 | 1 |
| Rpl29 | 175.4051724 | 413.5938187 | 96.00895697 | 0.232133443 | -2.106973714 | 0.036809129 | 1 |
| Fyco1 | 1037.000701 | 1430.595044 | 905.8109987 | 0.633170393 | -0.659333387 | 0.037022356 | 1 |
| Bccip | 904.2765193 | 582.4280104 | 1011.559356 | 1.736797231 | 0.796429331 | 0.037227595 | 1 |
| Eya3 | 640.1676353 | 929.0875638 | 543.8609925 | 0.585371082 | -0.772576618 | 0.037316446 | 1 |
| Itch | 1067.259551 | 1478.547951 | 930.1634177 | 0.629106021 | -0.668624926 | 0.037331564 | 1 |
| Dlgap3 | 16.43771463 | 53.94701983 | 3.934612898 | 0.072934729654 | -3.777249654 | 0.037453099 | 1 |
| Npat | 721.5221567 | 1033.984547 | 617.3680266 | 0.597076647 | -0.744011951 | 0.037490012 | 1 |
| Gadd45g | 386.5939077 | 209.793966 | 445.5272216 | 2.123641733 | 1.086540398 | 0.037501014 | 1 |
| Col6a6 | 1037.413981 | 1431.594063 | 906.0206201 | 0.632875368 | -0.660006676 | 0.0376085 | 1 |
| Mpp7 | 281.7987681 | 453.5545742 | 224.5468328 | 0.49506828 | -1.014259781 | 0.037672452 | 1 |
| Myeov2 | 172.9072993 | 58.94211426 | 210.8956943 | 3.578013733 | 1.839158925 | 0.037889192 | 1 |
| Ssr4 | 1518.537204 | 1037.980622 | 1678.722732 | 1.617296793 | 0.693584455 | 0.037941938 | 1 |
| Csnk1g3 | 475.8952089 | 718.2945789 | 395.0954189 | 0.5500465 | -0.862374509 | 0.037982856 | 1 |
| Ndufa3 | 197.8399194 | 84.91660529 | 235.4810242 | 2.773085704 | 1.471492204 | 0.038012431 | 1 |
| Slco1a6 | 290.5032127 | 466.5418197 | 231.8236771 | 0.496897484 | -1.008978484 | 0.0380167 | 1 |
| Fam125a | 165.735943 | 61.93917092 | 200.3348671 | 3.23438083 | 1.693489558 | 0.038030874 | 1 |
| Pgap2 | 82.54651485 | 173.8292861 | 52.11892443 | 0.299828214 | -1.737791946 | 0.038100274 | 1 |
| Fut1 | 116.3612426 | 225.7782682 | 79.8889007 | 0.353837866 | -1.498839647 | 0.038100393 | 1 |
| Lars2 | 34968.2868 | 11333.86926 | 42846.42598 | 3.780388233 | 1.918534402 | 0.03841367 | 1 |
| 1700008F21Rik | 6.243868036 | 24.97547214 | 0 | 0 | #NAME? | 0.038564458 | 1 |
| 1700111N16Rik | 6.243868036 | 24.97547214 | 0 | 0 | #NAME? | 0.038564458 | 1 |
| Rabl5 | 116.5071338 | 35.96467989 | 143.3546184 | 3.985983438 | 1.994935716 | 0.038599525 | 1 |
| Cbx6 | 370.1692715 | 198.8047583 | 427.2907759 | 2.149229835 | 1.103865886 | 0.038608303 | 1 |
| Runx1t1 | 1464.918492 | 1991.044639 | 1289.543109 | 0.647671621 | -0.626665564 | 0.038777165 | 1 |
| Scml4 | 198.6281158 | 83.91758641 | 236.8649589 | 2.822590223 | 1.497019697 | 0.038814046 | 1 |
| Lig3 | 557.3417161 | 814.2003919 | 471.7221575 | 0.57936862 | -0.787446548 | 0.038824344 | 1 |
| Slc41a2 | 83.6882076 | 171.8312484 | 54.30727401 | 0.316050046 | -1.661775068 | 0.038977361 | 1 |
| Xrcc4 | 144.6674702 | 51.94898206 | 175.573633 | 3.379731922 | 1.756908817 | 0.038984727 | 1 |
| Pak1 | 231.7750814 | 82.91856752 | 281.3939194 | 3.393617712 | 1.762824056 | 0.039401327 | 1 |
| Pcyt1b | 382.9908946 | 590.4201615 | 313.8478056 | 0.531566884 | -0.911676865 | 0.039416055 | 1 |
| Pdk1 | 225.2780886 | 380.6261955 | 173.4953863 | 0.455815675 | -1.133477556 | 0.03951726 | 1 |
| Gpr25 | 14.44134476 | 47.95290652 | 3.270824173 | 0.068209091 | -3.87389215 | 0.039679673 | 1 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Gm13003 | 19.72230329 | 60.94015203 | 5.983020375 | 0.098178626 | -3.348447218 | 0.039741345 | 1 |
| Ssh3 | 148.1395135 | 267.7370614 | 108.2736641 | 0.404402975 | -1.306134484 | 0.039762189 | 1 |
| Sestd1 | 325.6545684 | 512.4966884 | 263.3738617 | 0.513903539 | -0.960430508 | 0.039828053 | 1 |
| Aga | 492.929818 | 759.2543532 | 404.154973 | 0.532305111 | -0.909674675 | 0.039843085 | 1 |
| 1200011M11Rik | 150.047541 | 56.94407649 | 181.0820292 | 3.179997646 | 1.669025697 | 0.039997709 | 1 |
| Kcng3 | 75.9120461 | 162.8400784 | 46.93603533 | 0.288233927 | -1.794687933 | 0.040154196 | 1 |
| Swi5 | 603.5524478 | 330.6752512 | 694.5115133 | 2.100282712 | 1.070583537 | 0.040359929 | 1 |
| Alkbh7 | 94.82702799 | 25.97449103 | 117.7778736 | 4.534366949 | 2.180901148 | 0.040401824 | 1 |
| 1700034H15Rik | 26.89656089 | 75.92543532 | 10.55360275 | 0.138999568 | -2.846847691 | 0.040481069 | 1 |
| Arhgap44 | 556.8291563 | 813.201373 | 471.3717507 | 0.579649477 | -0.78674735 | 0.040828083 | 1 |
| Sobp | 291.885678 | 468.5398574 | 233.0009515 | 0.497291634 | -1.007835933 | 0.040831174 | 1 |
| Klhl20 | 276.1761088 | 453.5545742 | 217.0499537 | 0.478553114 | -1.063249039 | 0.041054093 | 1 |
| BC018507 | 904.719862 | 1260.761834 | 786.0392047 | 0.623463674 | -0.681622591 | 0.041181934 | 1 |
| Gtf2e2 | 251.973752 | 412.5947998 | 198.4334027 | 0.480940145 | -1.056070741 | 0.041205402 | 1 |
| Fnbp1 | 166.4321352 | 296.7086091 | 123.006644 | 0.414570525 | -1.270310546 | 0.041309189 | 1 |
| B430010I23Rik | 38.87539014 | 96.90483192 | 19.53224288 | 0.201561083 | -2.310710981 | 0.041504332 | 1 |
| Ttll4 | 174.5304066 | 303.7017413 | 131.4732951 | 0.432902671 | -1.207885392 | 0.041724952 | 1 |
| Rasgrf2 | 698.9043068 | 1006.012018 | 596.5350697 | 0.592970123 | -0.75396868 | 0.04174535 | 1 |
| Kif3c | 153.6858138 | 316.6889868 | 99.35142281 | 0.313719223 | -1.672454163 | 0.041970796 | 1 |
| Fam135b | 493.3356969 | 837.1778263 | 378.7216538 | 0.452378983 | -1.144396189 | 0.041999055 | 1 |
| 1700096K18Rik | 55.56817067 | 7.992151086 | 71.42684387 | 8.937123823 | 3.159810613 | 0.042049654 | 1 |
| Mycbp | 378.7954382 | 187.8155505 | 442.4554007 | 2.355797481 | 1.236215521 | 0.042160556 | 1 |
| Pcdha5 | 15.29633054 | 50.94996318 | 3.411786322 | 0.06696347 | -3.900481904 | 0.042320964 | 1 |
| Zfp239 | 49.86660699 | 116.6852096 | 27.52707277 | 0.235505184 | -2.086169279 | 0.042388394 | 1 |
| Vps36 | 129.2122279 | 44.95584986 | 157.2976873 | 3.498937019 | 1.806916696 | 0.042448637 | 1 |
| Mpzl3 | 31.62413353 | 0.999018886 | 41.83250508 | 41.87358786 | 5.387968633 | 0.042498392 | 1 |
| Bpgm | 325.2342884 | 172.8302672 | 376.0356287 | 2.175751011 | 1.121513467 | 0.042542248 | 1 |
| Gm13315 | 19.35404746 | 59.94113315 | 5.825020189 | 0.097178992 | -3.363211721 | 0.042748193 | 1 |
| Cib1 | 98.59785558 | 27.9725288 | 122.1396312 | 4.366413635 | 2.126448805 | 0.042816885 | 1 |
| Lss | 444.3737144 | 665.3465779 | 370.7160933 | 0.557177425 | -0.843791288 | 0.042846109 | 1 |
| Cgn | 341.2534966 | 161.8410595 | 401.0576423 | 2.478095753 | 1.309231934 | 0.043029662 | 1 |
| 6720401G13Rik | 708.2921565 | 1002.015942 | 610.3842278 | 0.609156204 | -0.715115874 | 0.043153154 | 1 |
| Cck | 23.46199983 | 68.93230312 | 8.305232069 | 0.120483891 | -3.053087832 | 0.043176819 | 1 |
| 4831426I19Rik | 5.994113315 | 23.97645326 | 0 | 0 | #NAME? | 0.043406197 | 1 |
| Naip5 | 5.994113315 | 23.97645326 | 0 | 0 | #NAME? | 0.043406197 | 1 |
| Slc19a1 | 117.2730291 | 35.96467989 | 144.3758122 | 4.014377792 | 2.005176395 | 0.04342534 | 1 |
| Tlcd2 | 19.80295988 | 60.94015203 | 6.090562498 | 0.099943343 | -3.322745719 | 0.043468713 | 1 |
| Tmem146 | 69.69604457 | 146.8557762 | 43.97613402 | 0.29945117 | -1.739607325 | 0.043651597 | 1 |
| Zfp599 | 38.48616447 | 95.90581304 | 19.34628161 | 0.201721679 | -2.309561958 | 0.04368355 | 1 |
| Cyp51 | 703.8108844 | 444.5634042 | 790.2267111 | 1.777534326 | 0.82987742 | 0.043703261 | 1 |
| Atp1b3 | 802.7466679 | 510.4986506 | 900.1626737 | 1.763630078 | 0.818278595 | 0.043853654 | 1 |
| Tanc1 | 280.0979358 | 448.5594797 | 223.9440878 | 0.499251711 | -1.002160723 | 0.043854075 | 1 |
| Mpnd | 164.6233829 | 65.93524646 | 197.5194284 | 2.995657694 | 1.58287278 | 0.043856981 | 1 |
| Bod1l | 1785.863717 | 2383.659062 | 1586.598602 | 0.665614738 | -0.587240717 | 0.043869134 | 1 |
| Nt5c3 | 1750.578747 | 1228.79323 | 1924.507252 | 1.566176641 | 0.647246936 | 0.043883072 | 1 |
| Tmem68 | 341.1179256 | 183.819475 | 393.5507424 | 2.14096326 | 1.098260039 | 0.043961585 | 1 |
| Snap23 | 1074.988393 | 1489.537159 | 936.8054707 | 0.628923868 | -0.669042708 | 0.043977628 | 1 |
| Myo1b | 356.8714936 | 192.810645 | 411.5584432 | 2.134521376 | 1.09391261 | 0.044240825 | 1 |
| Ralgds | 611.1018047 | 374.6320822 | 689.9250455 | 1.841606948 | 0.880965182 | 0.044280008 | 1 |
| Nfkb2 | 103.9989484 | 26.97350992 | 129.6740945 | 4.807460911 | 2.265275127 | 0.044428948 | 1 |
| Rai1 | 590.7922607 | 850.1650718 | 504.3346571 | 0.593219686 | -0.75336162 | 0.044470426 | 1 |
| Scaf1 | 218.0458849 | 364.6418933 | 169.1805488 | 0.463963554 | -1.107916614 | 0.044621603 | 1 |
| Ankrd11 | 2750.263139 | 3601.463083 | 2467.410523 | 0.685121334 | -0.545585348 | 0.044947955 | 1 |
| Abhd6 | 352.2892857 | 188.8145694 | 406.7808578 | 2.154393377 | 1.1072817 | 0.044967168 | 1 |
| Mrpl54 | 138.046439 | 49.95094429 | 167.4116039 | 3.351520302 | 1.744815673 | 0.045236104 | 1 |
| Atxn2l | 3583.795672 | 4697.386801 | 3212.598629 | 0.683911878 | -0.548117649 | 0.045346061 | 1 |
| Ctsz | 215.7447522 | 99.90188858 | 254.3590401 | 2.546084394 | 1.348282513 | 0.045424565 | 1 |
| Polr3a | 446.700437 | 663.3485402 | 374.4844026 | 0.564536409 | -0.824861467 | 0.045556353 | 1 |
| Rps18 | 325.3831979 | 174.828305 | 375.5681622 | 2.148211425 | 1.103135989 | 0.04588636 | 1 |
| Mob3b | 56.62923702 | 127.8744174 | 32.88084356 | 0.257133868 | -1.95940845 | 0.045965808 | 1 |
| She | 12.47491633 | 42.95781209 | 2.313951075 | 0.053865664 | -4.21449025 | 0.046093604 | 1 |
| Irak1bp1 | 220.6384159 | 365.6409122 | 172.3042505 | 0.47123898 | -1.085469214 | 0.046171027 | 1 |
| Pkd1 | 1134.637486 | 1544.483197 | 998.0222489 | 0.646185242 | -0.629980293 | 0.046217842 | 1 |
| Ano7 | 27.81179819 | 75.92543532 | 11.77391915 | 0.155072132 | -2.688988649 | 0.046283956 | 1 |
| Csf1 | 212.7565966 | 358.64778 | 164.1262021 | 0.457625033 | -1.127762123 | 0.046407393 | 1 |
| Ccdc39 | 13.84325391 | 45.95486875 | 3.139382297 | 0.068314466 | -3.871665089 | 0.046425822 | 1 |
| Kcnq1ot1 | 3601.321759 | 5102.988469 | 3100.76619 | 0.607637311 | -0.718717637 | 0.046496321 | 1 |
| Smad1 | 568.2360619 | 345.6605345 | 642.4279044 | 1.858551499 | 0.894178664 | 0.046607471 | 1 |
| Pitpnm2 | 689.733323 | 972.0453759 | 595.6293054 | 0.612758746 | -0.706608924 | 0.046757373 | 1 |
| Taf13 | 199.7815131 | 72.92837866 | 242.0658913 | 3.319227655 | 1.730847583 | 0.0469122 | 1 |
| Fam167a | 118.0057203 | 218.785136 | 84.4125818 | 0.385824117 | -1.373984771 | 0.046942003 | 1 |
| Nme2 | 652.8173891 | 333.6723079 | 759.1990829 | 2.275283459 | 1.18604629 | 0.047036827 | 1 |
| Jam3 | 75.74918314 | 158.8440028 | 48.05090991 | 0.302503771 | -1.724974966 | 0.047098099 | 1 |
| Srsf11 | 1719.835871 | 2270.769927 | 1536.191185 | 0.676506751 | -0.563823764 | 0.047169267 | 1 |
| Ogg1 | 39.73988531 | 98.90286969 | 20.01889052 | 0.202409602 | -2.304650362 | 0.047256778 | 1 |

TABLE 10-continued

List of differentially expressed transcripts in ALDH+ cells from wild-type and Foxo knockout mice

| Gene | baseMean_all | baseMean_WT ALDH+ | baseMean_Rip-Foxo KO ALDH+ | Fold-Change | log2 Fold-Change | p-value | Adjusted p-value |
|---|---|---|---|---|---|---|---|
| Cd16412 | 38.20558731 | 96.90483192 | 18.63917244 | 0.192345129 | −2.378230796 | 0.047258518 | 1 |
| Cryba2 | 53.81001578 | 121.8803041 | 31.11991969 | 0.255331819 | −1.969554762 | 0.047285347 | 1 |
| D3Ertd254e | 510.427111 | 748.2651455 | 431.1477662 | 0.576196511 | −0.79536717 | 0.047299613 | 1 |
| Cirbp | 514.7914101 | 303.7017413 | 585.154633 | 1.926741119 | 0.946162741 | 0.047542364 | 1 |
| Prkch | 11.60688216 | 40.95977432 | 1.822584774 | 0.044496944 | −4.490149941 | 0.047663063 | 1 |
| Rpap1 | 322.700142 | 499.5094429 | 263.7637083 | 0.52804549 | −0.921265876 | 0.047685407 | 1 |
| Btbd3 | 345.2249917 | 188.8145694 | 397.3617991 | 2.104508144 | 1.073483093 | 0.047694919 | 1 |
| Asb8 | 485.2959285 | 286.7184202 | 551.4884313 | 1.923449602 | 0.943696029 | 0.047756184 | 1 |
| Chaf1a | 27.79717458 | 76.92445421 | 11.42141471 | 0.148475733 | −2.751700942 | 0.04781994 | 1 |
| Ubqln4 | 360.5163351 | 551.458425 | 296.8689718 | 0.538334276 | −0.89342581 | 0.047822747 | 1 |
| Mga | 3051.20602 | 3969.102033 | 2745.240682 | 0.691652837 | −0.53188001 | 0.047893624 | 1 |
| Rgs7 | 671.0251807 | 418.5889131 | 755.1706032 | 1.80408649 | 0.851268505 | 0.047915687 | 1 |
| Sema3d | 7.24105553 | 27.9725288 | 0.330564439 | 0.011817467 | −6.40293534 | 0.047935971 | 1 |
| A930005I04Rik | 24.25730846 | 0 | 32.34307795 | Inf | Inf | 0.048090068 | 1 |
| Nfkbib | 211.3600686 | 96.90483192 | 249.5118142 | 2.57481293 | 1.364467619 | 0.048264453 | 1 |
| Lrch2 | 30.65251435 | 81.91954864 | 13.56350292 | 0.165571016 | −2.594477949 | 0.048266533 | 1 |
| Tshz2 | 1019.413196 | 1397.627421 | 893.3417874 | 0.639184502 | −0.645695666 | 0.048432881 | 1 |
| 3110040N11Rik | 151.2004415 | 58.94211426 | 181.9532172 | 3.086981515 | 1.626196844 | 0.048434727 | 1 |
| Nav1 | 2383.79572 | 3134.921264 | 2133.420538 | 0.68053401 | −0.555260832 | 0.04844276 | 1 |
| 2610044O15Rik | 83.85312195 | 172.8302672 | 54.19407352 | 0.313568187 | −1.673148897 | 0.048462428 | 1 |
| 4932415G12Rik | 328.2725082 | 510.4986506 | 267.5304608 | 0.524057136 | −0.932203983 | 0.0485336 | 1 |
| Dapl1 | 278.3141171 | 137.8646062 | 325.1306208 | 2.358332785 | 1.237767312 | 0.048738643 | 1 |
| 2410007B07Rik | 5.744358593 | 22.97743437 | 0 | 0 | #NAME? | 0.048842764 | 1 |
| Rgs2 | 346.7690603 | 157.844984 | 409.7437524 | 2.595861725 | 1.376213537 | 0.049010372 | 1 |
| Prpf39 | 619.0659424 | 881.1346573 | 531.7097041 | 0.603437511 | −0.728723715 | 0.049190275 | 1 |
| Hsf4 | 44.59043157 | 3.996075543 | 58.12188359 | 14.54474095 | 3.862425696 | 0.049457707 | 1 |
| Adcy7 | 22.1276535 | 65.93524646 | 7.525122515 | 0.114128981 | −3.131262906 | 0.049465555 | 1 |
| Lsm3 | 83.66690046 | 21.97841549 | 104.2297288 | 4.742367547 | 2.245607542 | 0.049537204 | 1 |
| Srp14 | 702.3585545 | 260.7439292 | 849.5634296 | 3.258228992 | 1.704088002 | 0.049796704 | 1 |
| Ascc1 | 121.8551864 | 225.7782682 | 87.21415909 | 0.386282346 | −1.372272351 | 0.049940491 | 1 |
| Serac1 | 270.499227 | 425.5820453 | 218.8049543 | 0.514131075 | −0.959791882 | 0.049965211 | 1 |

This table lists all genes differentially expressed between wild-type and triple Foxo-deficient ALDH+ cells, arranged by p-value

TABLE 11

Overview of differential changes in transcript profile of wild-type and Foxo knockout ALDH+ cells

| Change | Gene or network | Wild-type | Foxo KO |
|---|---|---|---|
| ↑↑↑ | ALDH1A3 | | |
| ↑ | Differentiation Factors | Bach2 | ↓ |
| | | Pax6 | |
| | | Rfx6 | |
| | | Rfx7 | |
| | | Hic2 | |
| | | NcoR | |
| | LncRNA | Malat1 | ↓ |
| | | Meg3 | |
| | | Peg3 | |
| | | Neat1 | |
| | | KcQ1ot1 | |
| | | Sngh11 | |
| ↓ | Gpcrs | Gipr | |
| | | Gpr116 | |
| | | Gpr137 | |
| | | Gpr98 | |
| | Cytochrome | Cyp27b1 | ↓↓↓ |
| | | Ndor | ↓↓ |
| | | | Cyb5r3 |
| | | | Elovl6 |
| | Ribosomes | 40S Subunit | |
| | | 60S Subunit | |
| | Mitochondria | Complex I | Complex III |
| | | Complex IV | |
| | | Complex V | |
| | Differentiation markers | Insulin | |
| | | IAPP | |
| | | Cpe | |
| | | ChgB | |
| | | Gcg | |
| | | Pyy | |
| | | Npy | |

Category list of principal genes altered in ALDH+ cells as a function of Foxo genotype. Upward arrows indicate genes with increased expression, downward arrows indicate genes with decreased expression. Arrows in the Foxo column indicate that the change is specific to Foxo knockout ALDH+ cells.

REFERENCES

Accili, D., and Arden, K. C. (2004). FOXOs at the crossroads of cellular metabolism, differentiation, and transformation. Cell 117, 421-426.

Al-Masri, M., Krishnamurthy, M., Li, J., Fellows, G. F., Dong, H. H., Goodyer, C. G., and Wang, R. (2010). Effect of forkhead box O1 (FOXO1) on beta cell development in the human fetal pancreas. Diabetologia 53, 699-711.

Atkinson, M. A., Bluestone, J. A., Eisenbarth, G. S., Hebrok, M., Herold, K. C., Accili, D., Pietropaolo, M., Arvan, P. R., Von Herrath, M., Markel, D. S., et al. (2011). How does type 1 diabetes develop? The notion of homicide or beta-cell suicide revisited. Diabetes 60, 1370-1379.

Bugliani, M., Liechti, R., Cheon, H., Suleiman, M., Marselli, L., Kirkpatrick, C., Filipponi, F., Boggi, U., Xenarios, I., Syed, F., et al. (2013). Microarray analysis of isolated human islet transcriptome in type 2 diabetes and the role of the ubiquitin-proteasome system in pancreatic beta cell dysfunction. Mol Cell Endocrinol 367, 1-10.

Butler, P. C., Meier, J. J., Butler, A. E., and Bhushan, A. (2007). The replication of beta cells in normal physiology, in disease and for therapy. Nat Clin Pract Endocrinol Metab 3, 758-768.

Defronzo, R. A., Tripathy, D., Schwenke, D. C., Banerji, M., Bray, G. A., Buchanan, T. A., Clement, S. C., Gastaldelli, A., Henry, R. R., Kitabchi, A. E., et al. (2013). Prevention of diabetes with pioglitazone in ACT NOW: physiologic correlates. Diabetes 62, 3920-3926. Dor, Y., and Glaser, B. (2013). beta-cell dedifferentiation and type 2 diabetes. N Engl J Med 368, 572-573.

Dunning, B. E., and Gerich, J. E. (2007). The role of alpha-cell dysregulation in fasting and postprandial hyperglycemia in type 2 diabetes and therapeutic implications. Endocr Rev 28, 253-283.

Ferrannini, E. (2010). The stunned beta cell: a brief history. Cell Metabolism 11, 349-352.

Greenwood, R. H., Mahler, R. F., and Hales, C. N. (1976). Improvement in insulin secretion in diabetes after diazoxide. Lancet 1, 444-447.

Guo, S., Dai, C., Guo, M., Taylor, B., Harmon, J. S., Sander, M., Robertson, R. P., Powers, A. C., and Stein, R. (2013). Inactivation of specific beta cell transcription factors in type 2 diabetes. J Clin Invest 123, 3305-3316.

Henquin, J. C., Accili, D., Ahren, B., Boitard, C., Seino, S., and Cerasi, E. (2011). Long in the shade, glucagon re-occupies centre court. Diabetes Obes Metab 13 Suppl 1, v-viii.

Kahn, S. E., Haffner, S. M., Heise, M. A., Herman, W. H., Holman, R. R., Jones, N. P., Kravitz, B. G., Lachin, J. M., O'Neill, M. C., Zinman, B., et al. (2006). Glycemic durability of rosiglitazone, metformin, or glyburide monotherapy. N Engl J Med 355, 2427-2443.

Kawamori, D. et al. (2006). The forkhead transcription factor Foxo1 bridges the JNK pathway and the transcription factor PDX-1 through its intracellular translocation. J Biol Chem 281 (2), 1091-1098.

Kitamura, T., Kitamura, Y. I., Kobayashi, M., Kikuchi, O., Sasaki, T., Depinho, R. A., and Accili, D. (2009). Regulation of pancreatic juxtaductal endocrine cell formation by FOXO1. Molecular and cellular biology 29, 4417-4430.

Kitamura, Y. I., Kitamura, T., Kruse, J. P., Raum, J. C., Stein, R., Gu, W., and Accili, D. (2005). FOXO1 protects against pancreatic beta cell failure through NeuroD and MafA induction. Cell metabolism 2, 153-163.

Leahy, J. L. (2008). Mary, Mary, quite contrary, how do your beta-cells fail? Diabetes 57, 2563-2564.

Levy, J., Atkinson, A. B., Bell, P. M., McCance, D. R., and Hadden, D. R. (1998). Beta-cell deterioration determines the onset and rate of progression of secondary dietary failure in type 2 diabetes mellitus: the 10-year follow-up of the Belfast Diet Study. Diabetic medicine: a journal of the British Diabetic Association 15, 290-296.

Lukinius, A., Stridsberg, M., and Wilander, E. (2003). Cellular expression and specific intragranular localization of chromogranin A, chromogranin B, and synaptophysin during ontogeny of pancreatic islet cells: an ultrastructural study. Pancreas 27, 38-46.

Marcato, P., Dean, C. A., Giacomantonio, C. A., and Lee, P. W. (2011). Aldehyde dehydrogenase: its role as a cancer stem cell marker comes down to the specific isoform. Cell cycle 10, 1378-1384.

Marchetti, P., Bugliani, M., Lupi, R., Marselli, L., Masini, M., Boggi, U., Filipponi, F., Weir, G. C., Eizirik, D. L., and Cnop, M. (2007). The endoplasmic reticulum in pancreatic beta cells of type 2 diabetes patients. Diabetologia 50, 2486-2494.

Marselli, L., Suleiman, M., Masini, M., Campani, D., Bugliani, M., Syed, F., Martino, L., Focosi, D., Scatena, F., Olimpico, F., et al. (2014). Are we overestimating the loss of beta cells in type 2 diabetes? Diabetologia 57, 362-365.

Nauck, M. A., Kleine, N., Orskov, C., Hoist, J. J., Willms, B., and Creutzfeldt, W. (1993). Normalization of fasting hyperglycaemia by exogenous glucagon-like peptide 1 (7-36 amide) in type 2 (non-insulin-dependent) diabetic patients. Diabetologia 36, 741-744.

Polonsky, K. S. (2012). The past 200 years in diabetes. N Engl J Med 367, 1332-1340.

Puri, S., Akiyama, H., and Hebrok, M. (2013). VHL-mediated disruption of Sox9 activity compromises beta-cell identity and results in diabetes mellitus. Genes Dev 27, 2563-2575.

Rahier, J., Guiot, Y., Goebbels, R. M., Sempoux, C., and Henquin, J. C. (2008). Pancreatic beta-cell mass in European subjects with type 2 diabetes. Diabetes Obes Metab 10 Suppl 4, 32-42.

Rovira, M., Scott, S. G., Liss, A. S., Jensen, J., Thayer, S. P., and Leach, S. D. (2010). Isolation and characterization of centroacinar/terminal ductal progenitor cells in adult mouse pancreas. Proc Natl Acad Sci USA 107, 75-80.

Savage, P. J., Bennion, L. J., Flock, E. V., Nagulesparan, M., Mott, D., Roth, J., Unger, R. H., and Bennett, P. H. (1979). Diet-induced improvement of abnormalities in insulin and glucagon secretion and in insulin receptor binding in diabetes mellitus. J Clin Endocrinol Metab 48, 999-1007.

Shimamura, M., Karasawa, H., Sakakibara, S., and Shinagawa, A. (2010). Raldh3 expression in diabetic islets reciprocally regulates secretion of insulin and glucagon from pancreatic islets. Biochem Biophys Res Commun 401, 79-84.

Spijker, H. S., Ravelli, R. B., Mommaas-Kienhuis, A. M., van Apeldoom, A. A., Engelse, M. A., Zaldumbide, A., Bonner-Weir, S., Rabelink, T. J., Hoeben, R. C., Clevers, H., et al. (2013). Conversion of mature human beta-cells into glucagon-producing alpha-cells. Diabetes 62, 2471-2480.

Suzuki, T., Kadoya, Y., Sato, Y., Handa, K., Takahashi, T., Kakita, A., and Yamashina, S. (2003). The expression of pancreatic endocrine markers in centroacinar cells of the normal and regenerating rat pancreas: their possible transformation to endocrine cells. Archives of histology and cytology 66, 347-358.

Talchai, C., Lin, H. V., Kitamura, T., and Accili, D. (2009). Genetic and biochemical pathways of beta-cell failure in type 2 diabetes. Diabetes Obes Metab 11 Suppl 4, 38-45.

Talchai, C., Xuan, S., Lin, H. V., Sussel, L., and Accili, D. (2012). Pancreatic beta Cell Dedifferentiation as a Mechanism of Diabetic beta Cell Failure. Cell 150, 1223-1234.

Taylor, B. L., Liu, F. F., and Sander, M. (2013). Nkx6.1 is essential for maintaining the functional state of pancreatic beta cells. Cell reports 4, 1262-1275.

U.K. Prospective Diabetes Study Group (1998). Effect of intensive blood-glucose control with metformin on complications in overweight patients with type 2 diabetes (UKPDS 34). UK Prospective Diabetes Study (UKPDS) Group. Lancet 352, 854-865.

Wajchenberg, B. L. (2007). beta-cell failure in diabetes and preservation by clinical treatment. Endocr Rev 28, 187-218.

Wang, J., Cortina, G., Wu, S. V., Tran, R., Cho, J. H., Tsai, M. J., Bailey, T. J., Jamrich, M., Ament, M. E., Treem, W. R., et al. (2006). Mutant neurogenin-3 in congenital malabsorptive diarrhea. N Engl J Med 355, 270-280.

Wang, X., Misawa, R., Zielinski, M. C., Cowen, P., Jo, J., Periwal, V., Ricordi, C., Khan, A., Szust, J., Shen, J., et al. (2013). Regional differences in islet distribution in the human pancreas—preferential beta-cell loss in the head region in patients with type 2 diabetes. PLoS One 8, e67454.

Wang, Z., York, N. W., Nichols, C. G., and Remedi, M. S. (2014). Pancreatic beta Cell Dedifferentiation in Diabetes and Redifferentiation following Insulin Therapy. Cell Metab in press.

Weng, J., Li, Y., Xu, W., Shi, L., Zhang, Q., Zhu, D., Hu, Y., Zhou, Z., Yan, X., Tian, H., et al. (2008). Effect of intensive insulin therapy on beta-cell function and glycaemic control in patients with newly diagnosed type 2 diabetes: a multicentre randomized parallel-group trial. Lancet 371, 1753-1760.

Weyer, C., Bogardus, C., Mott, D. M., and Pratley, R. E. (1999). The natural history of insulin secretory dysfunction and insulin resistance in the pathogenesis of type 2 diabetes mellitus. J Clin Invest 104, 787-794.

White, M. G., Marshall, H. L., Rigby, R., Huang, G. C., Amer, A., Booth, T., White, S., and Shaw, J. A. (2013). Expression of mesenchymal and alpha-cell phenotypic markers in islet beta-cells in recently diagnosed diabetes. Diabetes Care 36, 3818-3820.

Yoon, K. H., Ko, S. H., Cho, J. H., Lee, J. M., Ahn, Y. B., Song, K. H., Yoo, S. J., Kang, M. I., Cha, B. Y., Lee, K. W., et al. (2003). Selective beta-cell loss and alpha-cell expansion in patients with type 2 diabetes mellitus in Korea. J Clin Endocrinol Metab 88, 2300-2308.

What is claimed is:

1. A method, comprising
   a) obtaining a sample comprising beta cells from an isolated donor pancreas or isolated pancreatic islets,
   b) analyzing the sample using flow cytometry to determine the percentage of beta cells in the sample that express detectable levels of ALDH1A3, and
   c) (i) if the percentage of ALDH1A3-expressing beta cells in the sample is about 3% or lower, then determining that the pancreas or islets are healthy enough for implantation into a subject, and implanting the pancreas or islets into a subject in need, and
      (ii) and if the percentage of ALDH1A3-expressing cells is above about 5%, then determining that the pancreas or islets are not suitable for implantation into the subject and not implanting the pancreas or islets in the subject in need.

2. The method of claim 1, wherein the flow cytometry is fluorescent assisted cell sorting.

3. The method of claim 1, wherein the flow cytometry uses the reagent ALDEFLUOR™.

4. The method of claim 1, wherein the subject is human.

5. The method of claim 1, wherein the subject in need experiences one or more symptoms of diabetes.

6. A method comprising: obtaining a sample of beta cells from a pancreas or pancreatic islets, and isolating beta cells that express detectable levels of ALDH1A3 using flow cytometry.

7. ALDH1A3-expressing beta cells isolated by the method of claim 6.

8. A method, comprising
   a) contacting a population of ALDH1A3$^{hi}$ beta cells with a plurality of test agents in a high throughput screen for a time and under conditions that permit the test agent to affect ALDH1A3 expression or activity; and
   b) selecting a test agent if it caused a statistically significant reduction in the level of ALDH1A3 expression or activity compared to pre-contact levels.

9. The method of claim 8, further comprising;
   c) contacting a noninsulin-producing beta-cell population with the selected test agent of step b); and
   d) determining if the selected test agent caused at least a statistically significant increase in insulin production, insulin secretion or both after contact compared to respective pre-contact levels, and
   e) if the selected test agent significantly increases insulin production, insulin secretion or both after contact compared to respective pre-contact levels then selecting the test agent as a potential therapeutic agent.

10. The method of claim 9, wherein the noninsulin-producing beta-cell population comprises a whole pancreatic islet or an islet fragment.

11. The method of claim 10, wherein the noninsulin-producing beta-cell population is isolated from a mammalian diabetic pancreas.

12. The method of claim 11, wherein the diabetic pancreas is from a human.

13. The method of claim 9, wherein the significant increase is an increase of at least about 20% compared to precontact levels.

14. The method of claim 9, wherein the contacting is in vitro or in vivo.

15. The method of claim 8, wherein the ALDH1A3$^{hi}$ beta cells have no insulin production or impaired insulin production.

16. The method of claim 8, wherein the ALDH1A3$^{hi}$ beta cells are isolated from a human diabetic pancreas.

17. The method of claim 8, wherein the ALDH1A3$^{hi}$ beta cells are isolated from a diabetic pancreas using fluorescent-associated cell sorting.

18. The method of claim 8, wherein the level of ALDH1A3 expression is determined using either fluorescence of ALDH1A3 or a protein r mRNA assay.

19. The method of claim 8, wherein a reduction of ALDH1A3 correlates with an increase in insulin production or secretion or both.

20. The method of claim 8, wherein a significant reduction of ALDH1A3 expression or activity is reduction of about 2-, 10,-25-, 50- or 100-fold compared to precontact levels.

21. The method of claim 8, wherein a significant reduction in ALDH1A3 causes a delay in progression of dedifferentiation, cessation of dedifferentiation or a reversal of dedifferentiation of the beta cells.

22. The method of claim 8, wherein a significant increase in insulin production and/or secretion is about a 20% increase compared to precontact levels.

23. The method of claim 8 wherein the population of ALDH1A3$^{hi}$ beta cells is isolated from a mammalian diabetic pancreas.

24. Isolated noninsulin-producing or low-insulin-producing pancreatic beta cells that express a statistically significantly higher level of ALDH1A3 protein, mRNA encoding ALDH1A3 or ALDH1A3 enzyme activity than normal insulin-producing pancreatic cells.

25. The isolated cells of claim 24, wherein a significantly higher level of ALDH1A3 protein expression or enzyme activity is about 2-, 10,-25-, 50- or 100-fold higher than in normal insulin-producing pancreatic cells.

26. The isolated pancreatic cells of claim 24, wherein the cells are isolated by FACS based on elevated ALDH1A3 expression.

27. A method, comprising
   a) obtaining a sample comprising beta cells from an isolated donor pancreas or isolated pancreatic islets,
   b) analyzing the sample using to determine a percentage of beta cells in the sample that express detectable levels of ALDH1A3, and
   c) if the percentage of ALDH1A3-expressing beta cells in the sample is about 3% or lower, then determining that the pancreas or islets are healthy enough for implantation into a subject, and implanting the pancreas or islets into a subject in need.

28. The method of claim 27, wherein if the percentage of ALDH1A3-expressing cells is above about 5%, then determining that the pancreas or islets are not suitable for implantation into the subject and not implanting the pancreas or islets in the subject in need.

29. The method of claim 27, wherein the percentage is determined using flow cytometry.

\* \* \* \* \*